United States Patent
Liu et al.

(10) Patent No.: US 12,281,109 B2
(45) Date of Patent: Apr. 22, 2025

(54) INHIBITORS OF HISTONE DEACETYLASE-3 USEFUL FOR THE TREATMENT OF CANCER, INFLAMMATION, NEURODEGENERATION DISEASES AND DIABETES

(71) Applicant: Merck Sharp & Dohme LLC, Rahway, NJ (US)

(72) Inventors: Jian Liu, Edison, NJ (US); Younong Yu, East Brunswick, NJ (US); Joseph A. Kozlowski, Princeton, NJ (US); Deyou Sha, Yardley, PA (US); Wensheng Yu, Edison, NJ (US); Joseph M. Kelly, Parlin, NJ (US); Scott E. Wolkenberg, Wyndmoor, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 703 days.

(21) Appl. No.: 17/598,342

(22) PCT Filed: Mar. 30, 2020

(86) PCT No.: PCT/US2020/025631
§ 371 (c)(1),
(2) Date: Sep. 27, 2021

(87) PCT Pub. No.: WO2020/205688
PCT Pub. Date: Oct. 8, 2020

(65) Prior Publication Data
US 2022/0177465 A1    Jun. 9, 2022

Related U.S. Application Data

(60) Provisional application No. 62/829,159, filed on Apr. 4, 2019.

(51) Int. Cl.
| | |
|---|---|
| *A61P 25/28* | (2006.01) |
| *A61P 29/00* | (2006.01) |
| *A61P 31/18* | (2006.01) |
| *A61P 35/00* | (2006.01) |
| *C07D 401/14* | (2006.01) |
| *C07D 405/14* | (2006.01) |
| *C07D 417/12* | (2006.01) |
| *C07D 417/14* | (2006.01) |
| *C07D 487/04* | (2006.01) |

(52) U.S. Cl.
CPC ......... *C07D 417/12* (2013.01); *C07D 401/14* (2013.01); *C07D 405/14* (2013.01); *C07D 417/14* (2013.01); *C07D 487/04* (2013.01)

(58) Field of Classification Search
CPC .......... A61P 25/28; A61P 31/18; A61P 35/00; A61P 29/00; C07D 417/12; C07D 417/14; C07D 401/14; C07D 405/14; C07D 487/04
See application file for complete search history.

(56) References Cited

U.S. PATENT DOCUMENTS

| | | | |
|---|---|---|---|
| 2009/0156619 A1* | 6/2009 | Jones | A61P 11/06 514/400 |
| 2010/0324034 A1 | 12/2010 | Hazuda et al. | |

FOREIGN PATENT DOCUMENTS

WO    2014067985 A1    5/2014

OTHER PUBLICATIONS

Kinzel, Olaf et al., Discovery of a Potent Class I Selective Ketone Histone Deacetylase Inhibitor with Antitumor Activity in Vivo and Optimized Pharmacokinetic Properties, J. Med. Chem., 2009, 3453-3456, 52.

* cited by examiner

*Primary Examiner* — Sun Jae Yoo
(74) *Attorney, Agent, or Firm* — Eric Greenwald; John C. Todaro

(57) ABSTRACT

The present invention relates to Compounds of Formula I: and pharmaceutically acceptable salts or prodrug thereof, wherein $R^1$, $R^2$, $R^3$, A and B are as defined herein. The present invention also relates to compositions comprising at least one compound of Formula I, and methods of using the compounds of Formula I for treating or preventing cancer, inflammation, neurodegeneration disease and/or diabetes in a subject.

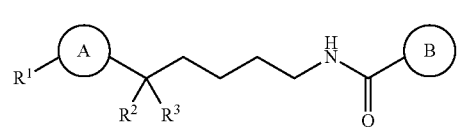

13 Claims, No Drawings

INHIBITORS OF HISTONE DEACETYLASE-3 USEFUL FOR THE TREATMENT OF CANCER, INFLAMMATION, NEURODEGENERATION DISEASES AND DIABETES

CROSS REFERENCE TO RELATED APPLICATIONS

This application is a U.S. National Phase application under 35 U.S.C. § 371 of PCT Application No. PCT/US2020/025631 filed Mar. 30, 2020, which claims priority to U.S. Ser. No. 62/829,159 filed Apr. 4, 2019.

FIELD OF THE INVENTION

The present invention relates to inhibitors of histone deacetylase, compositions comprising at least one inhibitor of histone deacetylase, and methods of using the inhibitors of histone deacetylase for the treatment or prevention of cancer, inflammation, neurodegeneration diseases and diabetes in a subject.

BACKGROUND OF THE INVENTION

DNA in the nucleus of the cell exists as a hierarchy of compacted chromatin structures. The basic repeating unit in chromatin is the nucleosome, which consists of a histone octamer of proteins in the nucleus of the cell around which DNA is wrapped twice. The orderly packaging of DNA in the nucleus plays an important role in the functional aspects of gene regulation. Covalent modifications of the histones have a key role in altering chromatin higher order structure and function, and ultimately, gene expression. The covalent modification of histones, such as acetylation, occurs by enzymatically mediated process.

Regulation of gene expression through the inhibition of the nuclear enzyme histone deacetylase (HDAC) is one of the several possible regulatory mechanisms whereby chromatin actively can be affected. The dynamic homeostasis of the nuclear acetylation of histone can be regulated by the opposing activity of the enzymes histone acetyl transferase (HAT) and histone deacetylase (HDAC). Transcriptionally silent chromatin can be characterized by nucleosomes with low levels of acetylated histones. Acetylation reduces the positive charge of histones, thereby expanding the structure of the nucleosome and facilitating the interaction of transcription factors with the DNA. Removal of the acetyl group restores the positive charge, condensing the structure of the nucleosome. While histone acetylation can activate DNA transcription, enhancing gene expression, histone deacetylase can reverse the process and can serve to repress gene expression. Inhibition of the histone deacetylase (HDAC inhibition) can also increase the activation of DNA transcription. See, for example, Grunstein, Nature, 389, 349-352 (1997); Pazin et al., Cell 89, 325-328 (1997); Wade et al., Trends Biochem Sci. 22, 128-132 (1997); and Wolffe, Science 272, 371-372 (1996).

Eleven members of the HDAC family have been identified in humans, which share a conserved catalytic domain and are grouped into two classes: class I (1,2,3,8), homologous to yeast Rpd3; and class IIa (4,5,7,9) and IIb (6, 10), homologous to yeast Hdal. HDAC 11 shares homology with both classes, but is at the same time distinct from all the other ten subtypes. The first generation of HDAC inhibitors (HDACi) are promising therapeutic agents against cancer and other diseases. In the whole family of HDACs, HDAC3 has gained more and more attention for its potential as a target for drug discovery. HDAC3 plays an important role in the initiation of leukemogenesis in acute promyelocytic leukemia (Mehdipour, P. etc. Leukemia (2017) 31, 995-997), which indicates HDAC3-selective inhibitors may be effective for the treatment of APL and possibly other hematological malignancies. In addition, HDAC3 has been reported to be associated with inflammation (Leus, G. J. Current Opinion in Chemical Biology 2016, 33:160-168). HDAC3 is identified as a negative regulator of long-term memory formation, and demonstrated HDAC3 inhibition was able to improve cognitive impairments (Wood, M. A. etc., J. Neurosci. 2013, 33, 6623-6632). Accordingly, HDAC3 may be useful in the treatment of neurodegeneration diseases, such as Alzheimer's disease and Huntington's disease. Knocking down HDAC3 also protects pancreatic b-cells from cytokine-induced apoptosis, and could restore glucose-stimulated insulin (Wagner, F. F. etc. ACS Chem. Biol. 2016, 11, 363-374). Treatment with a selective HDAC3 inhibitor also reduces hyperglycemia and increase insulin secreting in type-2 diabetes (Dirice, E etc. J. biol. Chem. 2017, 292, 17598-17608), thus HDAC3 may be a potential target for the treatment of diabetes.

SUMMARY OF THE INVENTION

In one aspect, the present invention provides Compounds of Formula I:

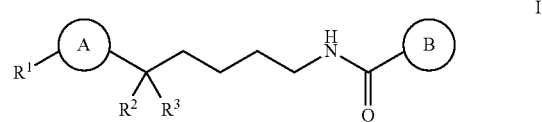

wherein

is a five-membered heteroaryl ring which is optionally substituted with halo, cyano or $C_{1-3}$ alkyl;

is phenyl or heteroaryl, which may be monocyclic or bicyclic, wherein said phenyl and heteroaryl groups are optionally substituted with one to three substituents independently selected from the group consisting of halo, oxo, cyano, $R^4$, $R^6$, $OR^4$, $NHR^4$, $NR^4R^5$, $NO_2$ and $SR^4$;

$R^1$ is naphthalenyl or quinolinyl wherein said naphthalenyl and quinolinyl groups are optionally substituted with one to two groups independently selected from the group consisting of halo, oxo, cyano, $R^4$ and $OR^4$;

$R^2$ is selected from the group consisting of $NH(C=O)R^6$, $NH(C=O)CH(CH_3)R^6$ and $NH(C=O)R^4$;

$R^3$ is hydrogen or $C_{1-6}$ alkyl;

or $R^2$ and $R^3$ can be taken together with the atoms to which they are attached to form a 5-membered heterocyclyl group which is optionally substituted with oxo;

each $R^4$ is independently hydrogen or $C_{1-6}$ alkyl, which is optionally substituted with one to three groups independently selected from the group consisting of halo, cyano and $OR^5$; each $R^5$ is independently hydrogen or $C_{1-6}$ alkyl;

$R^6$ is (a) heterocyclyl, which may be monocyclic or bicyclic,
(b) $C_{3-6}$ cycloalkyl,
(c) phenyl, or
(d) heteroaryl, which may be monocyclic or bicyclic, wherein said heterocyclyl, cycloalkyl, phenyl and heteroaryl groups are optionally substituted with one to two groups independently selected from the group consisting of oxo, $R^4$ and $OR^4$; or a pharmaceutically acceptable salt thereof.

The Compounds of Formula I and pharmaceutically acceptable salts or prodrugs thereof may be useful, for example, for the treatment of cancer, inflammation, neurodegeneration diseases and diabetes.

Accordingly, the present invention provides methods for treating or preventing cancer, inflammation, neurodegeneration diseases and diabetes in a subject, comprising administering to the subject an effective amount of at least one compound of Formula I.

The details of the invention are set forth in the accompanying detailed description below.

Although any methods and materials similar to those described herein may be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention includes inhibitors of histone deacetylase, compositions comprising at least one inhibitor of histone deacetylase, and methods of using the inhibitors of histone deacetylase for the treating or preventing cancer, inflammation, neurodegeneration diseases and/or diabetes in a subject.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of a Compound of Formula I and/or an additional therapeutic agent, or a composition thereof that is effective in treating cancer, inflammation, neurodegeneration diseases, such as Alzheimer's and Huntington's diseases, or diabetes. In the combination therapies of the present invention, an effective amount can refer to each individual agent or to the combination as a whole, wherein the amounts of all agents administered are together effective, but wherein the component agent of the combination may not be present individually in an effective amount.

As used herein, the terms "treatment" and "treating" refer to all processes in which there may be a slowing, interrupting, arresting, controlling, or stopping of the progression of a disease or disorder described herein. The terms do not necessarily indicate a total elimination of all disease or disorder symptoms.

The terms "preventing," or "prohylaxis," as used herein, refers to reducing the likelihood of contracting cancer, inflammation, neurodegeneration diseases and/or diabetes, or reducing the severity of cancer, inflammation, neurodegeneration diseases and/or diabetes.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

Unless otherwise indicated, an alkyl group is unsubstituted.

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on. Bicyclic cycloalkyl ring systems include fused ring systems, where two rings share two atoms, and spiro ring systems, where two rings share one atom.

The term "heteroaryl", as used herein, represents a stable monocyclic or bicyclic ring system of up to 10 atoms in each ring, wherein at least one ring is aromatic, and at least one ring contains from 1 to 4 heteroatoms selected from the group consisting of O, N and S. Bicyclic heteroaryl ring systems include fused ring systems, where two rings share two atoms, and spiro ring systems, where two rings share one atom. Heteroaryl groups within the scope of this definition include but are not limited to: azaindolyl, benzoimidazolyl, benzisoxazolyl, benzofuranyl, benzofurazanyl, benzopyrazolyl, benzotriazolyl, benzothiophenyl, benzoxazolyl, carbazolyl, carbolinyl, cinnolinyl, dihydroindenyl, furanyl, indolinyl, indolyl, indolazinyl, indazolyl, isobenzofuranyl, isoindolyl, isoquinolyl, isothiazolyl, isoxazolyl, naphthalenyl, naphthpyridinyl, oxadiazolyl, oxazolyl, oxazoline, isoxazoline, pyranyl, pyrazinyl, pyrazolyl, pyrazolopyrimidinyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, dihydrobenzodioxinyl, dihydropyrazoloxazinyl, dihydropyrazolyothiazinedioxidyl, methylenedioxybenzene, benzothiazolyl, benzothienyl, quinolinyl, isoquinolinyl, oxazolyl, tetra-hydroquinoline and 3-oxo-3, 4dihydro-2N-benzo[b][1,4]thiazine. If the heteroaryl contains nitrogen atoms, it is understood that the corresponding N-oxides thereof are also encompassed by this definition.

The term "heterocycle" or "heterocyclyl" as used herein is intended to mean a stable nonaromatic monocyclic or bicyclic ring system of up to 10 atoms in each ring, unless otherwise specified, containing from 1 to 4 heteroatoms selected from the group consisting of O, N, S, SO, or $SO_2$. Bicyclic heterocyclic ring systems include fused ring systems, where two rings share two atoms, and spiro ring systems, where two rings share one atom. "Heterocyclyl" therefore includes, but is not limited to the following: azaspirononanyl, azaspirooctanyl, azetidinyl, dioxanyl, oxadiazaspirodecenyl, oxaspirooctanyl, oxazolidinonyl, piperazinyl, piperidinyl, pyrrolidinyl, morpholinyl, thiomorpholinyl, tetrahydrofumayl, tetrahydropyranyl, dihydropiperidinyl, tetrahydrothiophenyl and the like. If the heterocycle contains a nitrogen, it is understood that the corresponding N-oxides thereof are also encompassed by this definition.

"Celite®" (Fluka) diatomite is diatomaceous earth, and can be referred to as "celite".

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., $R^4$) occurs more than one time in any constituent or in Formula I, its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a compound of Formula I or a pharmaceutically acceptable salt of the compound. The transformation may occur by various mechanisms (e.g., by metabolic or chemical processes), such as, for example, through hydrolysis in blood. For example, if a compound of Formula I or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl, and the like.

Similarly, if a compound of Formula I contains an alcohol functional group, a prodrug can be formed by the replacement of one or more of the hydrogen atoms of the alcohol groups with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkyl, α-amino$(C_1-C_4)$alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a compound of Formula I incorporates an amine functional group, a prodrug can be formed by the replacement of a hydrogen atom in the amine group with a group such as, for example, R-carbonyl-, RO-carbonyl-, NRR'-carbonyl- wherein R and R' are each independently $(C_1-C_{10})$ alkyl, $(C_3-C_7)$ cycloalkyl, benzyl, a natural α-aminoacyl, —C(OH)C(O)O$Y^1$ wherein $Y^1$ is H, $(C_1-C_6)$alkyl or benzyl, —C(O$Y^2$)$Y^3$ wherein $Y^2$ is $(C_1-C_4)$ alkyl and $Y^3$ is $(C_1-C_6)$ alkyl; carboxy $(C_1-C_6)$alkyl; amino$(C_1-C_4)$alkyl or mono-N— or di-N,N—$(C_1-C_6)$alkylaminoalkyl; —C($Y^4$)$Y^5$ wherein $Y^4$ is H or methyl and $Y^5$ is mono-N— or di-N,N—$(C_1-C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aryl (e.g., benzyl), aryloxyalkyl (for example, phenoxymethyl), aryl (e.g., phenyl optionally substituted with, for example, halogen, $C_{1-4}$alkyl, —O— ($C_{1-4}$alkyl) or amino); (2) sulfonate esters, such as alkyl- or arylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3, 601-611 (2004) describe the preparation of the solvates of the antifungal fluconazole in ethyl acetate as well as from water. Similar preparations of solvates, hemisolvates, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The compound of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), arylalkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the compound of Formula I may be atropisomers (e.g., substituted biaryls) and are considered as part of this invention. Enantiomers can also be directly separated using chiral chromatographic techniques.

It is also possible that the compound of Formula I may exist in different tautomeric forms, and all such forms are embraced within the scope of the invention. For example, all keto-enol and imine-enamine forms of the compounds are included in the invention.

Unless otherwise indicated, all stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a compound of Formula I incorporates a double bond or a fused ring, both the cis- and trans-forms, as well as mixtures, are embraced within the scope of the invention.

When a substituent on a chiral carbon atom is depicted without specific stereochemistry (by using a straight line bond to a chiral center), it is to be understood that both the alpha and beta configurations of said substituent group are to be considered part of the present invention. For example, the compound of the present invention, which is drawn as follows:

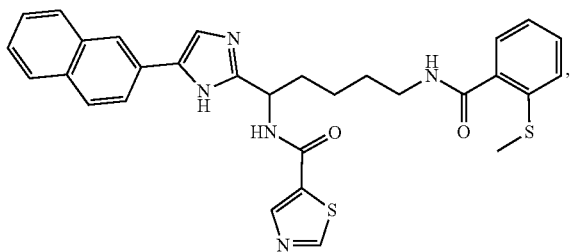 [SMILES: CSc1ccccc1C(=O)NCCCCC(NC(=O)c1cncs1)c1ncc(-c2ccc3ccccc3c2)[nH]1]

is understood to encompass both stereoisomers at the indicated chiral center, the structures of which are as follows:

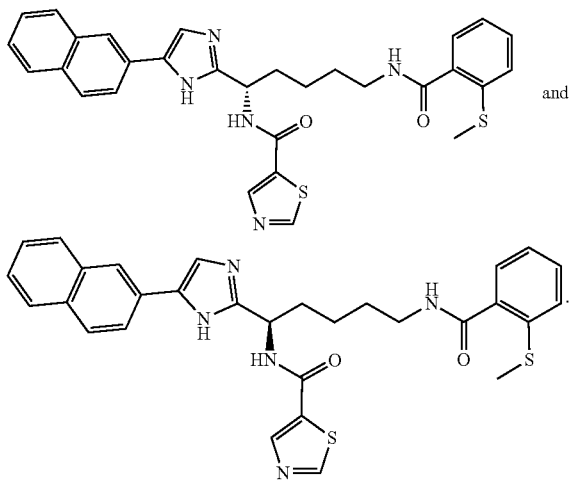

In the Examples section below, compounds of the present invention that have been purified as individual stereoisomers are sometimes depicted in non-stereospecific form but identified using one or more of the terms: "diastereomer 1," "diastereomer 2," "isomer 1," "isomer 2," "enantiomer A" and "enantiomer B." In this instance, the absolute stereochemistry of each isolated diastereomer and enantiomeric center has not been determined and the terms used above are used to represent each individual purified stereochemically pure compound.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include proton ($^1$H) and deuterium ($^2$H). Proton is the predominant hydrogen isotope found in nature. Enriching for deuterium may provide certain therapeutic advantages, such as increasing in vivo half-life or reducing dosage requirements, or may provide a compound useful as a standard for characterization of biological samples. Isotopically-enriched Compounds of Formula I can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula I has one or more of its hydrogen atoms replaced with deuterium.

The compounds of Formula I may be useful in human and veterinary medicine for treating or preventing cancer, inflammation, neurodegeneration diseases and/or diabetes in a subject. In one embodiment, the compounds of Formula I may be useful in human and veterinary medicine for treating or preventing cancer in a subject. In another embodiment, the compounds of Formula I may be useful in human and veterinary medicine for treating or preventing inflammation in a subject. In another embodiment, the compounds of Formula I may be useful in human and veterinary medicine for treating or preventing neurodegeneration diseases in a subject. In another embodiment, the compounds of Formula I may be useful in human and veterinary medicine for treating or preventing diabetes in a subject.

Accordingly, in one embodiment, the invention provides methods for treating cancer in a subject comprising administering to the subject an effective amount of at least one compound of Formula I or a pharmaceutically acceptable salt thereof. In another embodiment, the invention provides methods for treating inflammation in a subject comprising administering to the subject an effective amount of at least one compound of Formula I or a pharmaceutically acceptable salt thereof. In another embodiment, the invention provides methods for treating neurodegeneration diseases in a subject comprising administering to the subject an effective amount of at least one compound of Formula I or a pharmaceutically acceptable salt thereof. In another embodiment, the invention provides methods for treating diabetes in a subject comprising administering to the subject an effective amount of at least one compound of Formula I or a pharmaceutically acceptable salt thereof.

The Compounds of Formula I

The present invention provides Compounds of Formula I:

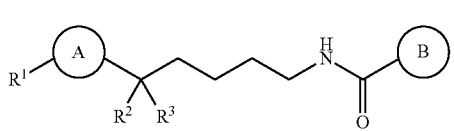

wherein

is a five-membered heteroaryl ring which is optionally substituted with halo, cyano or $C_{1-3}$ alkyl;

is phenyl or heteroaryl, which may be monocyclic or bicyclic, wherein said phenyl and heteroaryl groups are optionally substituted with one to three substituents independently selected from the group consisting of halo, oxo, cyano, $R^4$, $R^6$, $OR^4$, $NHR^4$, $NR^4R^5$, $NO_2$ and $SR^4$; $R^1$ is naphthalenyl or quinolinyl wherein said naphthalenyl and quinolinyl groups are optionally substituted with one to two groups independently selected from the group consisting of halo, oxo, cyano, $R^4$ and $OR^4$;
$R^2$ is selected from the group consisting of $NH(C=O)R^6$, $NH(C=O)CH(CH_3)R^6$ and $NH(C=O)R^4$;
$R^3$ is hydrogen or $C_{1-6}$ alkyl;
or $R^2$ and $R^3$ can be taken together with the atoms to which they are attached to form a 5-membered heterocyclyl group which is optionally substituted with oxo;
each $R^4$ is independently hydrogen or $C_{1-6}$ alkyl, which is optionally substituted with one to three groups independently selected from the group consisting of halo, cyano and $OR^5$;
each $R^5$ is independently hydrogen or $C_{1-6}$ alkyl;
$R^6$ is
(a) heterocyclyl, which may be monocyclic or bicyclic,
(b) $C_{3-6}$ cycloalkyl,
(c) phenyl, or
(d) heteroaryl, which may be monocyclic or bicyclic,
wherein said heterocyclyl, cycloalkyl, phenyl and heteroaryl groups are optionally substituted with one to two groups independently selected from the group consisting of oxo, $R^4$ and $OR^4$; or a pharmaceutically acceptable salt thereof.

In an embodiment of the invention,  is imidazolyl.
In an embodiment of the invention,

is phenyl, pyridinyl, pyrazolyl, pyrazolopyrimidinyl, oxadiazolyl, thiadiazolyl, isothiazolyl, or dihydroindenyl, wherein said groups are optionally substituted with one to three substituents independently selected from the group consisting of halo, oxo, cyano, $R^4$, $R^6$, $OR^4$, $NHR^4$, $NR^4R^5$, $NO_2$ and $SR^4$. In a class of the embodiment,

is phenyl. In another class of the embodiment,

is pyridinyl. In another class of the embodiment,

is pyrazolyl. In another class of the embodiment,

is pyrazolopyrimidinyl. In another class of the embodiment,

is oxadiazolyl. In another class of the embodiment,

is thiadiazolyl. In another class of the embodiment,

is isothiazolyl. In another class of the embodiment, is dihydroindenyl.

In an embodiment of the invention, $R^1$ is naphthalenyl or quinolinyl wherein said quinolinyl group is optionally substituted with $OR^4$. In a class of the embodiment, $R^1$ is naphthalenyl. In another class of the embodiment, $R^1$ is quinolinyl which is substituted with $OR^4$.

In an embodiment of the invention, $R^2$ is $NH(C=O)R^6$ or $NH(C=O)C(CH_3)R^6$, and $R^6$ is selected from the group consisting of azetidinyl, piperidinyl, pyrazolyl, tetrahydropyranyl and thiazolyl. In a class of the embodiment, $R^2$ is $NH(C=O)$thiazolyl.

In an embodiment of the invention, $R^3$ is hydrogen.

In another embodiment, the Compounds of Formula I are in substantially purified form.

It is to be understood that any of the aforementioned embodiments may be combined with one or more separate embodiments.

Other embodiments of the present invention include the following:

(a) A pharmaceutical composition comprising an effective amount of a Compound of Formula I, and a pharmaceutically acceptable carrier.

(b) The pharmaceutical composition of (a), further comprising a second therapeutic agent selected from the group consisting of anti-cancer agents, immunomodulators, anti-infective agents, vaccines, and antibodies.

(c) A pharmaceutical combination that is (i) a Compound of Formula I and (ii) a second therapeutic agent selected from the group consisting of anti-cancer agents, immunomodulators, anti-infective agents, vaccines, and antibodies; wherein the Compound of Formula I and the second therapeutic agent are each employed in an amount that renders the combination effective for treating cancer.

(d) A method of treating cancer in a subject in need thereof which comprises administering to the subject an effective amount of a Compound of Formula I.

(e) The method of (d), wherein the Compound of Formula I is administered in combination with an effective amount of at least one second therapeutic agent selected from the group consisting of anti-cancer agents, immunomodulators, and anti-infective agents.

(f) A method of treating cancer in a subject in need thereof which comprises administering to the subject the pharmaceutical composition of (a) or (b) or the combination of (c).

Additional embodiments of the present invention include the following:

(g) A pharmaceutical composition comprising an effective amount of a pharmaceutically acceptable salt of a Compound of Formula I, and a pharmaceutically acceptable carrier.

(h) The pharmaceutical composition of (g), further comprising a second therapeutic agent selected from the group consisting of anti-inflammatory agents, immunomodulators, anti-infective agents, vaccines and antibodies.

(i) A pharmaceutical combination that is (i) a pharmaceutically acceptable salt of a Compound of Formula I and (ii) a second therapeutic agent selected from the group consisting of anti-inflammatory agents, immunomodulators, and anti-infective agents; wherein the pharmaceutically acceptable salt of the Compound of Formula I and the second therapeutic agent are each employed in an amount that renders the combination effective for treating inflammation and/or reducing the likelihood or severity inflammation.

(j) A method of treating inflammation and/or reducing the likelihood or severity of inflammation in a subject in need thereof which comprises administering to the subject an effective amount of a pharmaceutically acceptable salt of a Compound of Formula I.

(k) The method of (j), wherein the pharmaceutically acceptable salt of the Compound of Formula I is administered in combination with an effective amount of at least one second therapeutic agent selected from the group consisting of anti-inflammatory agents, immunomodulators, and anti-infective agents.

(l) A method of treating inflammation in a subject in need thereof which comprises administering to the subject the pharmaceutical composition of (g) or (h) or the combination of (i).

(m) A method of treating inflammation and/or reducing the likelihood or severity of inflammation in a subject in need thereof which comprises administering to the subject the pharmaceutical composition of (g) or (h) or the combination of (i).

Further embodiments of the present invention include the following:

(n) A pharmaceutical composition comprising an effective amount of a Compound of Formula I or a pharmaceutically acceptable salt thereof, and a pharmaceutically acceptable carrier.

(o) The pharmaceutical composition of (n), further comprising a second therapeutic agent selected from the group consisting of neuroprotective agents and immunomodulators.

(p) A pharmaceutical combination that is (i) a Compound of Formula I and (ii) or a pharmaceutically acceptable salt thereof, a second therapeutic agent selected from the group consisting of neuroprotective agents and immunomodulators; wherein the Compound of Formula I and the second therapeutic agent are each employed in an amount that renders the combination effective for treating neurodegeneration diseases and/or reducing the likelihood or severity of symptoms of neurodegeneration diseases.

(q) A method of treating neurodegeneration diseases in a subject in need thereof which comprises administering to the subject an effective amount of a Compound of Formula I or a pharmaceutically acceptable salt thereof.

(r) A method of treating neurodegeneration diseases and/or reducing the likelihood or severity of symptoms of neurodegeneration diseases in a subject in need thereof which comprises administering to the subject an effective amount of a Compound of Formula I or a pharmaceutically acceptable salt thereof.

(s) The method of (r), wherein the Compound of Formula I or pharmaceutically acceptable salt thereof, is administered in combination with an effective amount of at least one second therapeutic agent selected from the group consisting of neuroprotective agents and immunomodulators.

(t) A method of treating neurodegeneration diseases in a subject in need thereof which comprises administering to the subject the pharmaceutical composition of (n) or (o) or the combination of (p).

(u) A method of treating neurodegeneration diseases and/or reducing the likelihood or severity of neurodegeneration diseases in a subject in need thereof which comprises administering to the subject the pharmaceutical composition of (n) or (o) or the combination of (p).

Further embodiments of the present invention include the following:

(v) A pharmaceutical composition comprising an effective amount of a Compound of Formula I or a pharmaceutically acceptable salt thereof, and a pharmaceutically acceptable carrier.

(w) The pharmaceutical composition of (v), further comprising a second therapeutic agent selected from the group consisting of anti-diabetes agents.

(x) A pharmaceutical combination that is (i) a Compound of Formula I and (ii) or a pharmaceutically acceptable salt thereof, a second therapeutic agent selected from the group consisting of anti-diabetes agents; wherein the Compound of Formula I and the second therapeutic agent are each employed in an amount that renders the combination effective for treating diabetes and/or reducing the likelihood or severity of symptoms of diabetes.

(y) A method of treating diabetes in a subject in need thereof which comprises administering to the subject an effective amount of a Compound of Formula I or a pharmaceutically acceptable salt thereof.

(z) A method of treating diabetes and/or reducing the likelihood or severity of symptoms of diabetes in a subject in need thereof which comprises administering to the subject an effective amount of a Compound of Formula I or a pharmaceutically acceptable salt thereof.

(aa) The method of (z), wherein the Compound of Formula I or pharmaceutically acceptable salt thereof, is administered in combination with an effective amount of at least one second therapeutic agent selected from the group consisting of neuroprotective agents and immunomodulators.

(bb) A method of treating diabetes in a subject in need thereof which comprises administering to the subject the pharmaceutical composition of (v) or (w) or the combination of (x).

(cc) A method of treating diabetes and/or reducing the likelihood or severity of diabetes in a subject in need thereof which comprises administering to the subject the pharmaceutical composition of (v) or (w) or the combination of (x).

The present invention also includes a compound of the present invention for (i) use in, (ii) as a medicament for, or (iii) in the preparation of a medicament for: (a) medicine; (b) treating cancer, inflammation, neurodegeneration diseases and/or diabetes in a subject or (c) treating or preventing cancer, inflammation, neurodegeneration diseases and/or diabetes in a subject. In these uses, the compounds of the present invention can optionally be employed in combination with one or more second therapeutic agents.

Additional embodiments of the invention include the pharmaceutical compositions, combinations and methods set forth in (a)-(cc) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (cc) above are understood to include all embodiments of the compounds, including such embodiments as result from combinations of embodiments.

Non-limiting examples of the Compounds of Formula I include compounds 1-63 as set forth in the Examples below, and pharmaceutically acceptable salts thereof.

Methods for Making the Compounds of Formula I

The Compounds of Formula I may be prepared from known or readily prepared starting materials, following methods known to one skilled in the art of organic synthesis. Methods useful for making the Compounds of Formula I are set forth in the Examples below and generalized in the Schemes below. Alternative synthetic pathways and analogous structures will be apparent to those skilled in the art of organic synthesis.

General List of Abbreviations

Abbreviations and acronyms employed herein include the following:

| | |
|---|---|
| Ac | Acetyl |
| Aq | Aqueous |
| ACN | Acetonitrile |
| AIBN | Azobisisobutyronitrile |
| AUC | Area under the curve |
| BAST | Bis(2-methoxyethyl)aminosulfur trifluoride |
| BOC | tert-butyloxycarbonyl |
| Bu | Butyl |
| Bz | Benzoyl |
| CDI | Carbonyldiimidazole |
| DBDMH | 1,3-Dibromo-5,5-dimethylhydantoin |
| DCM | Dichloromethane |
| DCE | 1,2-Dichloroethane |
| DHP | 3,4-dihydro-2H-pyran |
| DIBAL-H | Diisobutylaluminium hydride |
| DIEA, DIPEA or Hünig's base | N,N-diisopropylethylamine |
| DMAP, 4-DMAP | 4-dimethylaminopyridine |
| DME | dimethyoxyethane |
| DMF | dimethylformamide |
| DMP | Dess-Martin periodinane |
| Dppf | 1,1'-Bis(diphenylphosphino)ferrocene |
| DMSO | dimethyl sulfoxide |
| DTBPF | 1,1-bis(di-tert-butylphosphino)ferrocene |
| EA | Ethyl Acetate |
| EDC | 1-Ethyl-3-(3-dimethylaminopropyl)carbodiimide |
| EDCI | N-ethyl-N'(3-dimethylaminopropyl)carbodiimide hydrochloride |
| Et | Ethyl |
| EtOH | Ethanol |
| EtOAc | ethyl acetate |
| G | Grams |
| GI | Gastrointenstinal |
| H | Hour |
| HATU | 1-[Bis(dimethylamino)methylene]-1H-1,2,3-triazolo[4,5-b]pyridinium 3-oxide hexafluorophosphate |
| HIV | human immunodeficiency virus |
| HOBT, HOBt | 1-Hydroxybenzotriazole hydrate |
| HPBCD | hydroxypropyl β-cyclodextrin |
| HPLC | high-performance liquid chromatography |
| mCPBA, CPBA | meta-Chloroperoxybenzoic |
| Hz | Hertz |
| IPA | Isopropanol |
| IV | Intravenous |
| iPr | Isopropyl |
| $Ir[dF(CF_3)ppy]_2$ (dtbpy)$PF_6$ | [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate |
| L | Liter |
| LC | liquid chromatography |
| LC/MS | liquid chromatography mass spectrometry |
| LED | light-emitting diode |
| LiHMDS | lithium bis(trimethylsilyl)amide |
| Me | Methyl |
| MeOH | Methanol |
| Mg | Milligrams |
| MHz | Megahertz |
| Min | Minute |
| μL | Microliters |
| mL | Milliliters |
| Mmol | Millimoles |
| MOM-Cl | chloromethyl methyl ether |
| MPLC | medium pressure liquid chromatography |
| MS | mass spectrometry |
| NBS | N-Bromosuccinimide |
| NCS | N-Chlorosuccinimide |
| NHS | normal human serum |
| NIS | N-Iodosuccinimide |
| NMO | 4-methylmorpholine N-oxide |
| NMR | nuclear magnetic resonance spectroscopy |
| PBMC | peripheral blood mononuclear cell |
| $Pd_2(dba)_3$ | Tris(dibenzylideneacetone)dipalladium(0) |
| Ph | Phenyl |
| P.O. | Oral |
| PPTS | Pyridinium p-toluenesulfonate |
| PTSA | para-toluenesulfonic acid |
| Pr | Propyl |
| Rpm | revolutions per minute |
| RT or rt | room temperature (ambient, about 25° C.) |
| sat or sat'd | Saturated |
| SEMCl | 2-Chloromethoxyethyl)trimethylsilane |
| SFC | supercritical fluid chromatography |
| T3P, $T_3P$ | 1-Propanephosphonic anhydride solution |
| TBAF | Tetra-n-butylammonium fluoride |

| | |
|---|---|
| TBDPSCl | tert-Butyldiphenylchlorosilane |
| TBSCl | tert-Butyldimethylsilyl chloride |
| tBu | tert-butyl |
| TEA | triethylamine ($Et_3N$) |
| TEMED | Tetramethylethylenediamine |
| TFA | trifluoroacetic acid |
| TFV | Tenofovir |
| TFV-MP | Tenofovir monophosphoate |
| TFV-DP | Tenofovir diphosphate |
| THF | Tetrahydrofuran |
| TMS | Tetramethylsilane |
| TosMIC | Toluenesulfonylmethyl isocyanide |
| TPAP | Tetrapropylammonium perruthenate |
| Ts | Tosyl |
| UPLC | ultrahigh pressure liquid chromatography |
| UV | Ultraviolet |
| UV/VIS | ultraviolet/visible |
| W | Watt |
| XPhos | 2-Dicyclohexylphosphino-2',4',6'-triisopropylbiphenyl |

General Procedures

Starting materials and intermediates are purchased or are made using known procedures, or as otherwise illustrated. The general route applied to the synthesis of compounds of Formula I is described in the Schemes that follows. In some cases the order of carrying out the reaction steps in the schemes may be varied to facilitate the reaction or to avoid unwanted reaction products.

Reactions sensitive to moisture or air were performed under nitrogen or argon using anhydrous solvents and reagents. The progress of reactions was determined by either analytical thin layer chromatography (TLC) usually performed with F. Merck pre-coated TLC plates, silica gel 60F7-254, layer thickness 0.25 mm or liquid chromatography-mass spectrometry (LC/MS).

Typically the analytical LC-MS system used consisted of a Waters ZQ™ platform with electrospray ionization in positive ion detection mode with an Agilent 1100 series HPLC with autosampler. The column was commonly a Waters Xterra MS C18, 3.0×50 mm, 5 µm or a Waters Acquity UPLC® BEH C18 1.0×50 mm, 1.7 µm. The flow rate was 1 mL/mM, and the injection volume was 10 µL. UV detection was in the range 210-400 nm. The mobile phase consisted of solvent A (water plus 0.05% TFA) and solvent B (MeCN plus 0.05% TFA) with a gradient of 100% solvent A for 0.7 min changing to 100% solvent B over 3.75 min, maintained for 1.1 min, then reverting to 100% solvent A over 0.2 min. Alternatively, the column was commonly a Waters Acquity UPLC© BEH C18 1.0×50 mm, 1.7 µm. The flow rate was 0.3 mL/min, and the injection volume was 0.5 µL. UV detection was 215 or 254 nm. Either the mobile phase consisted of solvent A (water plus 0.05% TFA) and solvent B (MeCN plus 0.05% TFA) with a gradient of 90% solvent A changing to 99% solvent B over 1.6 min, maintained for 0.4 min, then reverting to 90% solvent A over 0.1 min or the mobile phase consisted of solvent A (water plus 0.05% TFA) and solvent B (MeCN plus 0.05% TFA) with a gradient of 97% solvent A changing to 4% then 50% solvent B over 0.5 min and 0.9 min, 50%-99% solvent B over 0.2 min, maintained for 0.4 min, then reverting to 90% solvent A over 0.1 min.

Preparative HPLC purifications were usually performed using either a mass spectrometry directed system or a non-mass guided system. Usually they were performed on a Waters Chromatography Workstation configured with LC-MS System consisting of: Waters ZQ™ single quad MS system with Electrospray Ionization, Waters 2525 Gradient Pump, Waters 2767 Injecto/Collector, Waters 996 PDA Detector, the MS Conditions of: 150-750 amu, Positive Electrospray, Collection Triggered by MS, and a Waters SUNFIRE™ C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 µL, and the UV detection range was 210-400 nm. An alternate preparative HPLC system used was a Gilson Workstation consisting of: Gilson GX-281 Injector/Collector, Gilson UV/VIS-155 Detector, Gilson 322, 333, and 334 Pumps, and a Phenomenex Gemini-NX C-18 5 micron, 50 mm (id)×250 mm column, a Waters XBridge™ C-18 5 micron OBD™, 30 mm (id)×250 mm column, or a Waters SUNFIRE™ C-18 OBD™ 10 micron, 30 mm (id)×150 mm column. The mobile phases consisted of mixtures of acetonitrile (0-90%) in water containing 0.1% or 0.05% TFA. Flow rates were maintained at 50 mL/min for the Waters Xbridge™ column, 90 mL/min for the Phenomenex Gemini column, and 30 mL/min for the Waters SUNFIRE™ column. The injection volume ranged from 1000-8000 µL, and the UV detection range was 210-400 nm. Mobile phase gradients were optimized for the individual compounds. Reactions performed using microwave irradiation were normally carried out using an Emrys Optimizer manufactured by Personal Chemistry, or an Initiator manufactured by Biotage. Reactions performed using photon irradiation were normally carried out using either a second generation Merck photoreactor or a Kessil 34 W blue LED lamp. Concentration of solutions was carried out on a rotary evaporator under reduced pressure. Flash chromatography was usually performed using either a Biotage® Flash Chromatography apparatus (Dyax Corp.), an ISCO CombiFlash® Rf apparatus, or an ISCO CombiFlash® Companion XL on silica gel (32-63 microns, 60 Å pore size) in pre-packed cartridges of the size noted. $^1$H NMR spectra were acquired at 500 MHz spectrometers in $CDCl_3$ solutions unless otherwise noted. Chemical shifts were reported in parts per million (ppm). Tetramethylsilane (TMS) was used as internal reference in $CDCl_3$ solutions, and residual $CH_3OH$ peak or TMS was used as internal reference in $CD_3OD$ solutions. Coupling constants (J) were reported in hertz (Hz). Chiral analytical chromatography was most commonly performed on one of CHIRALPAK© AS, CHIRALPAK®AD, CHIRALCEL© OD, CHIRALCEL©IA, or CHIRALCEL® OJ columns (250×4.6 mm) (Daicel Chemical Industries, Ltd.) with noted percentage of ethanol in hexane (% EtOH/Hex), isopropanol in heptane (% IPA/Hep), ethanol in carbon dioxide (% EtOH/$CO_2$), or isopropanol in carbon dioxide (% IPA/$CO_2$) as isocratic solvent systems. Chiral preparative chromatography was conducted on one of CHIRALPAK AS, of CHIRALPAK AD, CHIRALCEL® OD, CHIRALCEL®IA, CHIRALCEL® OJ columns (20×250 mm) (Daicel Chemical Industries, Ltd.) with desired isocratic solvent systems identified on chiral analytical chromatography or by supercritical fluid (SFC) conditions.

Several catalysts are used in the following procedures. "UMICORE M71 SIPR" is also known as Umicore Hoveyda Grubbs Catalyst M71 SIPr" and [1,3-Bis(2,6-diisopropylphenyl)-2-imidazolidinylidene]dichloro[(2-isopropoxy)(5-trifluoroacetamido)benzylidene]ruthenium(II). It is available from Umicore Precious Metals Chemistry USA, LLC, 1305 Main Parkway Catoosa, Okla. 74015.

Several methods for preparing the compounds of this invention are also described in the Examples. Starting materials and intermediates were purchased commercially from

Intermediate 1

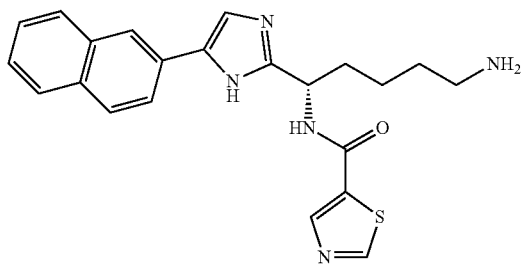 [SMILES: NCCCC[C@H](NC(=O)c1cncs1)c1ncc(-c2ccc3ccccc3c2)[nH]1]

(S)-N-(5-amino-1-(5-(naphthalen-2-yl)-1H-imidazol-2-yl)pentyl)thiazole-5-carboxamide Step 1: (S)-2-(naphthalen-2-yl)-2-oxoethyl 6-(((benzyloxy)carbonyl)amino)-2-((tert-butoxycarbonyl)amino)hexanoate A 250 mL one neck round bottom flask was charged with (S)-6-(((benzyloxy)carbonyl)amino)-2-((tert-butoxycarbonyl)amino)hexanoic acid (1000 mg, 2.63 mmol) along with cesium carbonate (514 mg, 1.577 mmol) in DMF (6 mL). The mixture was stirred while a solution of 2-bromo-1-(naphthalen-2-yl)ethanone (720 mg, 2.89 mmol) in DMF (6 mL) was added via syringe in 5 min. The resulting reaction mixture was then stirred at room temperature for 1 hr. The mixture was then diluted with ethyl acetate (20 mL) and the solid was filtered and washed with ethyl acetate. The filtrate was then concentrated and the residue was purified by MPLC (40 g silica gel, 0 to 40% ethyl acetate 18CV) to afford the product (S)-2-(naphthalen-2-yl)-2-oxoethyl 6-(((benzyloxy)carbonyl)amino)-2-((tert-butoxycarbonyl)amino)hexanoate.

Step 2: (S)-benzyl tert-butyl (1-(5-(naphthalen-2-yl)-1H-imidazol-2-yl)pentane-1,5-diyl)dicarbamate A 5 mL micro reaction vial was charged with (S)-2-(naphthalen-2-yl)-2-oxoethyl 6-(((benzyloxy)carbonyl)amino)-2-((tert-butoxycarbonyl)amino)hexanoate (264 mg, 0.481 mmol) along with ammonium acetate (148 mg, 1.925 mmol) in t-butanol (5 ml). The vial was sealed and stirred in an oil bath of 90° C. for 45 min. The mixture was cooled to room temperature and diluted with ethyl acetate (20 ml), washed with NaHCO₃ (sat, 20 mL), water, brine, dried over MgSO4, filtered and concentrated. The crude was purified by MPLC (24 g silica gel, 0 to 60% ethyl acetate in hexanes, 18 CV) to afford the product (S)-benzyl tert-butyl (1-(5-(naphthalen-2-yl)-1H-imidazol-2-yl)pentane-1,5-diyl)dicarbamate. MS (ESI) m/z: 529.3[M+H+].

$^1$H NMR (400 MHz, CD$_3$OD) δ 8.15 (br s, 1H), 7.75-7.92 (m, 4H), 7.39-7.51 (m, 3H), 7.20-7.36 (m, 5H), 4.96-5.09 (m, 2H), 4.76 (br s, 1H), 3.12 (t, J=6.8 Hz, 2H), 1.82-1.99 (m, 2H), 1.50-1.61 (m, 2H), 1.45 (br s, 9H), 1.36 (br d, J=5.6 Hz, 2H).

Step 3: (S)-benzyl (5-amino-5-(5-(naphthalen-2-yl)-1H-imidazol-2-yl)pentyl)carbamate To a stirred solution of (S)-benzyl tert-butyl (1-(5-(naphthalen-2-yl)-1H-imidazol-2-yl)pentane-1,5-diyl)dicarbamate (800 mg, 1.513 mmol) in DCM (10 mL) was added TFA (3 mL) at 23° C., and after the addition was finished, the reaction was stirred at 23° C. The reaction was monitored by LC-MS. After stirring at 23° C. for 2 h, the reaction was finished. The solvent was removed by concentration in vacuo to give crude (S)-benzyl (5-amino-5-(5-(naphthalen-2-yl)-1H-imidazol-2-yl)pentyl)carbamate, which was used directly in the next step without further purification.
MS (ESI) m/z: 429.36[M+H+].

Step 4: (S)-benzyl (5-(5-(naphthalen-2-yl)-1H-imidazol-2-yl)-5-(thiazole-5-carboxamido)pentyl)carbamate To a stirred solution of (S)-benzyl (5-amino-5-(5-(naphthalen-2-yl)-1H-imidazol-2-yl)pentyl)carbamate (650 mg, 1.517 mmol) and thiazole-5-carboxylic acid (235 mg, 1.820 mmol) in DCM (10 mL) was added DIEA (1.060 mL, 6.07 mmol) and HATU (692 mg, 1.820 mmol) at 23° C. After the addition was finished, the reaction was stirred at 23° C. The reaction was monitored by LC-MS, and after it was stirred at 23° C. for 16 h, the reaction was finished. After it was cooled to room temperature, water (20 mL) was added, it was extracted by ethyl acetate (20 mL×3), and the organic layers were collected, washed with brine, dried over Na₂SO₄, filtered, and the filtrate was concentrated in vacuo. The residue was purified by flash silica gel chromatography (ISCO; 12 g Agela Silica Flash Column, Eluent of 5% ethyl acetate/petroleum ether gradient @ 30 mL/min) to give (S)-benzyl (5-(5-(naphthalen-2-yl)-1H-imidazol-2-yl)-5-(thiazole-5-carboxamido)pentyl)carbamate.
MS (ESI) m/z: 540.2[M+H+].

Step 5: (S)-N-(5-amino-1-(5-(naphthalen-2-yl)-1H-imidazol-2-yl)pentyl)thiazole-5-carboxamide A solution of (S)-benzyl (5-(5-(naphthalen-2-yl)-1H-imidazol-2-yl)-5-(thiazole-5-carboxamido)pentyl)carbamate (400 mg, 0.741 mmol) in HBr (1 mL, 0.741 mmol) (30% in AcOH) was stirred at 20° C. The reaction was monitored by LC-MS, and after it was stirred at 20° C. for 16 h, the reaction was finished. The solvent was removed by concentration in vacuo. The residue was purified by reversed phase HPLC on a GILSON 281 instrument fitted with a Waters XSELECT C18 150*30 mm*5 um using water (0.1% TFA)-CH3CN as eluents, followed by lyophilization to give (S)-N-(5-amino-1-(5-(naphthalen-2-yl)-1H-imidazol-2-yl)pentyl)thiazole-5-carboxamide.
MS (ESI) m/z: 406.3[M+H+]

Example 1

(S)-N-(5-(2-(methylthio)benzamido)-1-(5-(naphthalen-2-yl)-1H-imidazol-2-yl)pentyl)thiazole-5-carboxamide

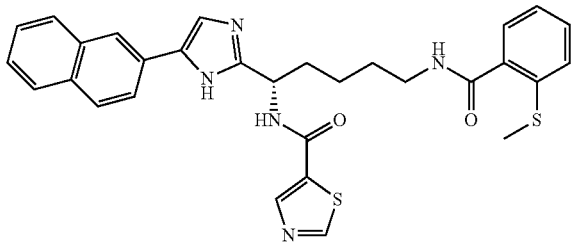 [SMILES: CSc1ccccc1C(=O)NCCCC[C@H](NC(=O)c1cncs1)c1ncc(-c2ccc3ccccc3c2)[nH]1]

To a stirred solution of (S)-N-(5-amino-1-(5-(naphthalen-2-yl)-1H-imidazol-2-yl)pentyl)thiazole-5-carboxamide (150 mg, 0.370 mmol) and 2-(methylthio)benzoic acid (63 mg, 0.375 mmol) in DMF (0.5 mL) was added TEA (0.16 mL, 1.148 mmol) and HATU (145 mg, 0.381 mmol) at 20° C. After the addition was finished, the reaction was stirred at 20° C. The reaction was monitored by LC-MS, and after it was stirred at 20° C. for 16 h, the reaction was finished. The reaction mixture was purified by reversed phase HPLC on a GILSON 281 instrument fitted with a Waters XSELECT C18 150*30 mm*5 um using water (0.1% TFA)-CH$_3$CN as eluents, extracted by DCM (20 mL×3), the organic layers was concentrated in vacuo to (S)-N-(5-(2-(methylthio)benzamido)-1-(5-(naphthalen-2-yl)-1H-imidazol-2-yl)pentyl)thiazole-5-carboxamide.

MS (ESI) m/z: 556.2 [M+H+].

1H NMR (500 MHz, CD$_3$OD) δ 9.17 (s, 1H), 8.60 (d, J=0.5 Hz, 1H), 8.24 (d, J=1.0 Hz, 1H), 7.99 (d, J=8.5 Hz, 1H), 7.89-7.95 (m, 3H), 7.78 (dd, J=8.5, 2.0 Hz, 1H), 7.53-7.60 (m, 2H), 7.32-7.38 (m, 1H), 7.26-7.31 (m, 2H), 7.11 (td, J=7.5, 1.5 Hz, 1H), 5.34-5.42 (m, 1H), 3.44 (t, J=6.5 Hz, 2H), 2.35 (s, 3H), 2.24-2.33 (m, 2H), 1.73-1.80 (m, 2H), 1.55-1.72 (m, 2H).

Example 2

(S)-N-(5-(2-(methylamino)benzamido)-1-(5-(naphthalen-2-yl)-1H-imidazol-2-yl) pentyl)thiazole-5-carboxamide

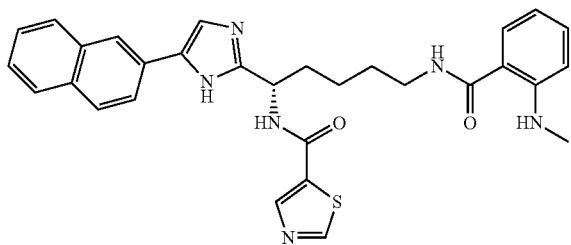 [SMILES: CNc1ccccc1C(=O)NCCCC[C@H](NC(=O)c1cncs1)c1ncc(-c2ccc3ccccc3c2)[nH]1]

To a stirred solution of (S)-N-(5-amino-1-(5-(naphthalen-2-yl)-1H-imidazol-2-yl)pentyl)thiazole-5-carboxamide (150 mg, 0.370 mmol) and 2-(methylamino)benzoic acid (56 mg, 0.370 mmol) in DMF (0.5 mL) was added TEA (016 mL, 115 mmol) and HATU (145 mg, 0.381 mmol) at 20° C. After the addition was finished, the reaction was stirred at 20° C. The reaction was monitored by LC-MS, and after it was stirred at 20° C. for 16 h, the reaction was finished. The reaction mixture was purified by reverse phase HPLC on a GILSON 281 instrument equipped with a Waters XSELECT C18 150*30 mm*5 um using water (0.04% NH3H2O+10 mM NH4HCO3)-MeCN as eluents, extracted by DCM (20 mL×3), and the organic layers were concentrated in vacuo to give (S)-N-(5-(2-(methylamino)benzamido)-1-(5-(naphthalen-2-yl)-1H-imidazol-2-yl)pentyl)thiazole-5-carboxamide.

MS (ESI) m/z: 539.3[M+H+]

$^1$H NMR (500 MHz, CD$_3$OD) δ 9.13 (s, 1H), 8.53 (s, 1H), 8.02-8.26 (m, 1H), 7.72-7.94 (m, 4H), 7.33-7.53 (m, 4H), 7.25 (ddd, J=8.5, 7.0, 1.5 Hz, 1H), 6.65 (d, J=8.0 Hz, 1H), 6.51 (t, J=7.5 Hz, 1H), 5.29 (t, J=7.5 Hz, 1H), 3.34-3.39 (m, 2H), 2.80 (s, 3H), 2.07-2.26 (m, 2H), 1.71 (quin, J=7.0 Hz, 2H), 1.50-1.59 (m, 2H).

Example 3

(S)-N-(5-(2-methoxybenzamido)-1-(5-(naphthalen-2-yl)-1H-imidazol-2-yl) pentyl)thiazole-5-carboxamide

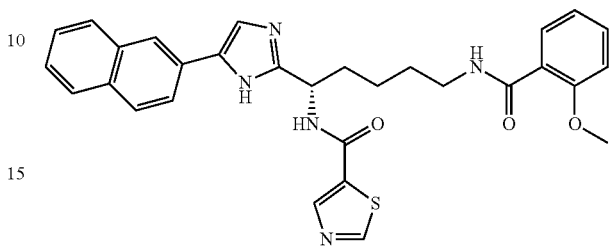

To a stirred solution of (S)-N-(5-amino-1-(5-(naphthalen-2-yl)-1H-imidazol-2-yl)pentyl)thiazole-5-carboxamide (150 mg, 0.370 mmol) and 2-methoxybenzoic acid (56.3 mg, 0.370 mmol) in DMF (1.5 mL) was added TEA (0.16 mL, 1.148 mmol) and HATU (141 mg, 0.370 mmol) at 20° C. After the addition was finished, the reaction was stirred at 20° C. for 16 h.

The reaction was monitored by LC-MS, and after it was stirred at 20° C. for 16 h, the reaction was finished. The reaction mixture was purified by reversed phase HPLC on a GILSON 281 instrument fitted with a Waters XSELECT C18 150*30 mm*5 um using water (0.1% TFA)-CH$_3$CN as eluents, extracted by DCM (20 mL×3), and the organic layers were concentrated in vacuo to give (S)-N-(5-(2-methoxybenzamido)-1-(5-(naphthalen-2-yl)-1H-imidazol-2-yl)pentyl)thiazole-5-carboxamide.

MS (ESI) m/z: 540.3 [M+H+]

$^1$H NMR (400 MHz, CD$_3$OD) δ 9.10-9.21 (m, 1H), 8.59 (s, 1H), 8.22 (d, J=1.2 Hz, 1H), 7.99 (d, J=8.4 Hz, 1H), 7.88-7.94 (m, 3H), 7.78 (ddd, J=8.0, 6.0, 1.6 Hz, 2H), 7.52-7.61 (m, 2H), 7.41 (ddd, J=8.8, 7.2, 2.0 Hz, 1H), 7.03 (d, J=8.0 Hz, 1H), 6.90-6.98 (m, 1H), 5.31-5.42 (m, 1H), 3.79-3.91 (m, 3H), 3.48 (t, J=6.4 Hz, 2H), 2.27 (q, J=7.6 Hz, 2H), 1.76 (quin, J=6.8 Hz, 2H), 1.50-1.70 (m, 2H).

Example 4

(S)-N-(5-(2-mercaptobenzamido)-1-(5-(naphthalen-2-yl)-1H-imidazol-2-yl)pentyl)thiazole-5-carboxamide

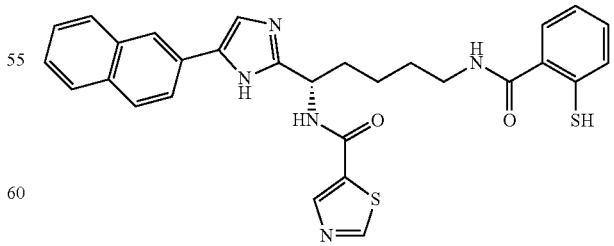

A 20 mL sample vial was charged with 2-mercaptobenzoic acid (25.9 mg, 0.168 mmol) along with N-ethyl-N-isopropylpropan-2-amine (59.3 mg, 0.459 mmol) in DMF (2 ml) and followed by HATU (63.9 mg, 0.168 mmol). The mixture was stirred for 5 min and then transferred to a mixture of (S)-N-(5-amino-1-(5-(naphthalen-2-yl)-1H-imidazol-2-yl)pentyl)thiazole-5-carboxamide, intermediate 1 (62 mg, 0.153 mmol). The resulting reaction mixture was then stirred at room temperature for 2 hrs. The mixture was then diluted with ethyl acetate (20 mL), washed with NaHCO$_3$ (sat, 5 mL), brine, dried over MgSO4, filtered and concentrated. The residue was purified by MPLC (12 g silica gel, 0 to 10% methanol in methylene chloride, 28 CV) to afford the product (S)-N-(5-(2-mercaptobenzamido)-1-(5-(naphthalen-2-yl)-1H-imidazol-2-yl)pentyl)thiazole-5-carboxamide. LCMS (ESI) calc'd for $C_{29}H_{27}N_5O_2S_2$ [M+H]$^+$: 542.2, found: 542.3.

$^1$H NMR (500 MHz, CD$_3$OD) δ 9.11 (s, 1H), 8.53 (s, 1H), 8.16 (s, 1H), 7.78-7.96 (m, 4H), 7.49 (s, 1H), 7.41-7.47 (m, 2H), 7.36 (dd, J=7.5, 1.0 Hz, 1H), 7.30 (d, 8.0 Hz, 1H), 7.18 (td, J=8.0, 1.5 Hz, 1H), 7.03 (td, J=7.5, 1.0 Hz, 1H), 5.30 (t, J=5.5 Hz, H), 3.37 (td, 6.0, 3.0 Hz, 2H), 2.10-2.20 9m, 2H), 1.68-1.72 (m, 2H), 1.50-1.59 (m, 2H) ppm.

Using similar methodology as described in Examples 1-4, the following examples were prepared using the appropriate acidic starting materials to provide the final amide coupling products:

| Example | Structure | Name | Exact Mass [M + H]$^+$ |
|---|---|---|---|
| 5 | 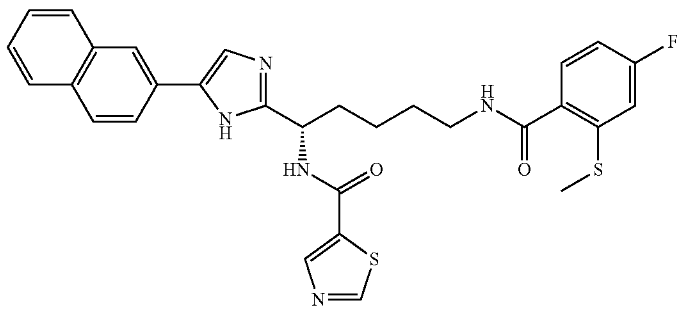 [SMILES: CSc1cc(F)ccc1C(=O)NCCCC[C@H](NC(=O)c1cncs1)c1ncc(-c2ccc3ccccc3c2)[nH]1] | (S)-N-(5-(4-fluoro-2-(methylthio)benzamido)-1-(5-(naphthalen-2-yl)-1H-imidazol-2-yl)pentyl)thiazole-5-carboxamide | 574.2 |
| 6 | 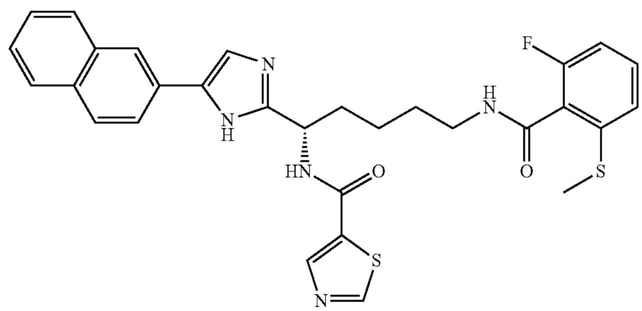 [SMILES: CSc1cccc(F)c1C(=O)NCCCC[C@H](NC(=O)c1cncs1)c1ncc(-c2ccc3ccccc3c2)[nH]1] | (S)-N-(5-(2-fluoro-6-(methylthio)benzamido)-1-(5-(naphthalen-2-yl)-1H-imidazol-2-yl)pentyl)thiazole-5-carboxamide | 574.2 |
| 7 | 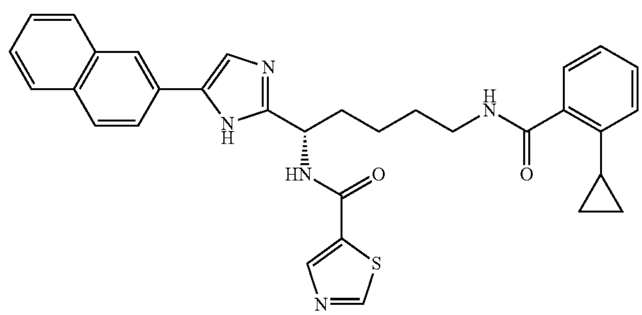 [SMILES: O=C(N[C@@H](CCCCNC(=O)c1ccccc1C1CC1)c1ncc(-c2ccc3ccccc3c2)[nH]1)c1cncs1] | (S)-N-(5-(4-cyclopropylbenzamido)-1-(5-(naphthalen-2-yl)-1H-imidazol-2-yl)pentyl)thiazole-5-carboxamide | 550.2 |
| 8 | 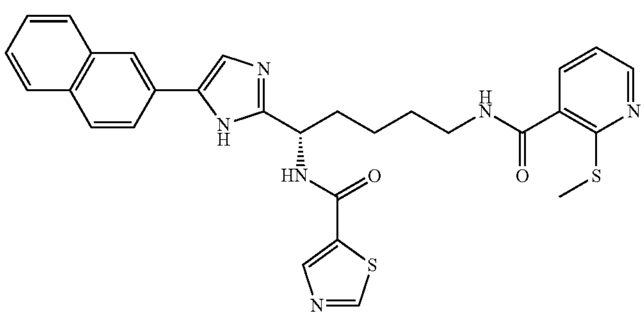 [SMILES: CSc1ncccc1C(=O)NCCCC[C@H](NC(=O)c1cncs1)c1ncc(-c2ccc3ccccc3c2)[nH]1] | (S)-N-(5-(2-(methylthio)nicotinamido)-1-(5-(naphthalen-1-yl)-1H-imidazol-2-yl)pentyl)thiazole-5-carboxamide | 557.2 |

-continued

| Example | Structure | Name | Exact Mass [M + H]⁺ |
|---|---|---|---|
| 9 | 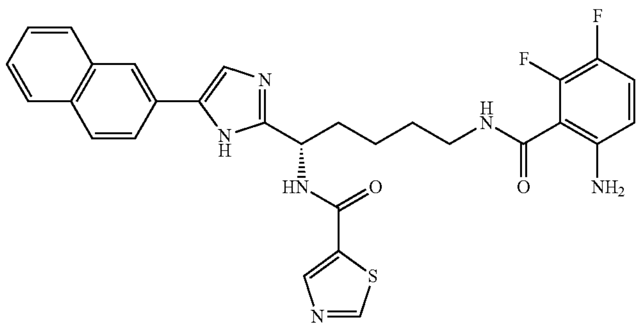 [SMILES: Nc1ccc(F)c(F)c1C(=O)NCCCC[C@H](NC(=O)c1cncs1)c1ncc(-c2ccc3ccccc3c2)[nH]1] | (S)-N-(5-(6-amino-2,3-difluorobenzamido)-1-(5-(naphthalen-2-yl)-1H-imidazol-2-yl)pntyl)thiazole-5-carboxamide | 561.2 |
| 10 | 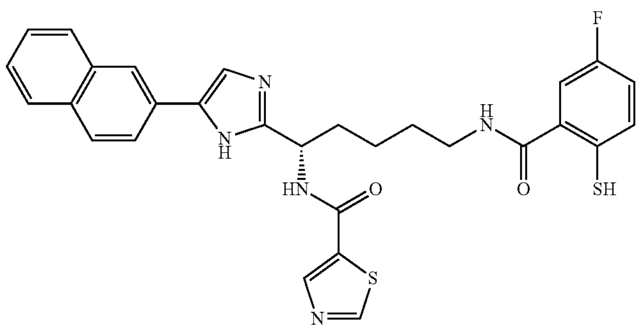 [SMILES: O=C(N[C@@H](CCCCNC(=O)c1cc(F)ccc1S)c1ncc(-c2ccc3ccccc3c2)[nH]1)c1cncs1] | (S)-N-(5-(5-fluoro-2-mercaptobenzamido)-1-(5-(naphthalen-2-yl)-1H-imidazol-2-yl)pentyl)thiazole-5-carboxamide | 559.2 |
| 11 | 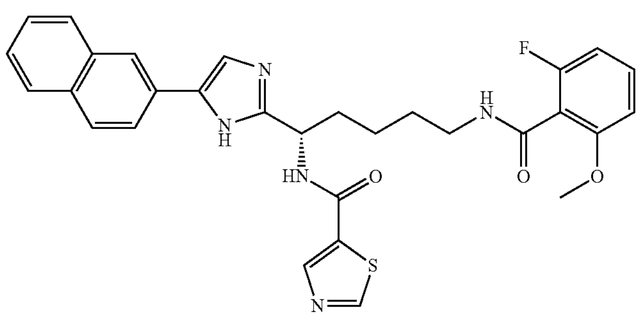 [SMILES: COc1cccc(F)c1C(=O)NCCCC[C@H](NC(=O)c1cncs1)c1ncc(-c2ccc3ccccc3c2)[nH]1] | (S)-N-(5-(2-fluoro-6-methoxybenzamido)-1-(5-(naphthalen-2-yl)-1H-imidazol-2-yl)pentyl)thiazole-5-carboxamide | 558.2 |
| 12 | 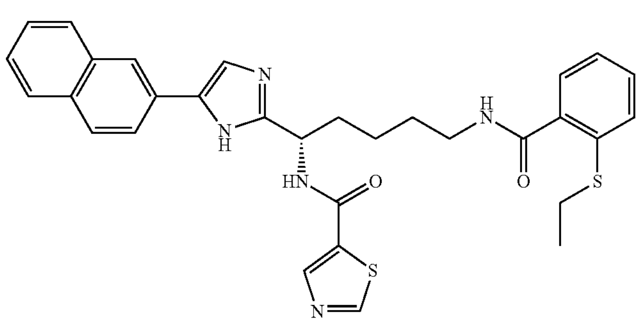 [SMILES: CCSc1ccccc1C(=O)NCCCC[C@H](NC(=O)c1cncs1)c1ncc(-c2ccc3ccccc3c2)[nH]1] | (S)-N-(5-(2-(ethylthio)benzamido)-1-(5-(naphthalen-2-yl)-1H-imidazol-2-yl)pentyl)thiazole-5-carboxamide | 570.2 |

-continued

| Example | Structure | Name | Exact Mass [M + H]+ |
|---|---|---|---|
| 13 | 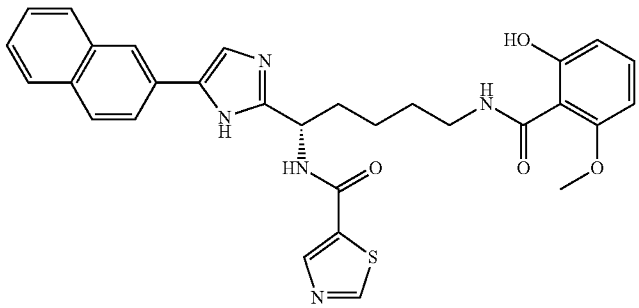 [SMILES: COc1cccc(O)c1C(=O)NCCCC[C@H](NC(=O)c1cncs1)c1ncc(-c2ccc3ccccc3c2)[nH]1] | (S)-N-(5-(2-hydroxy-6-methoxybenzamido)-1-(5-(naphthalen-2-yl)-1H-imidazol-2-yl)pentyl)thiazole-5-carboxamide | 556.2 |
| 14 | 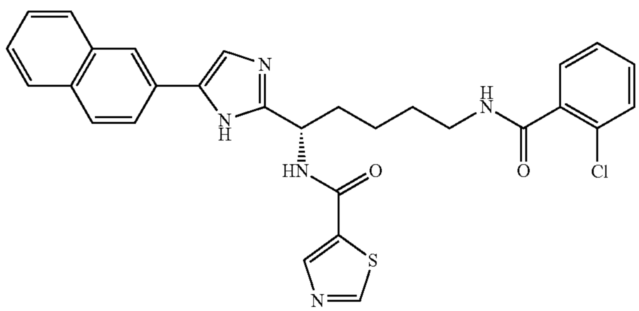 [SMILES: O=C(N[C@@H](CCCCNC(=O)c1ccccc1Cl)c1ncc(-c2ccc3ccccc3c2)[nH]1)c1cncs1] | (S)-N-(5-(2-chlorobenzamido)-1-(5-(naphthalen-2-yl)-1H-imidazol-2-yl)pentyl)thiazole-5-carboxamide | 546.1 |
| 15 | 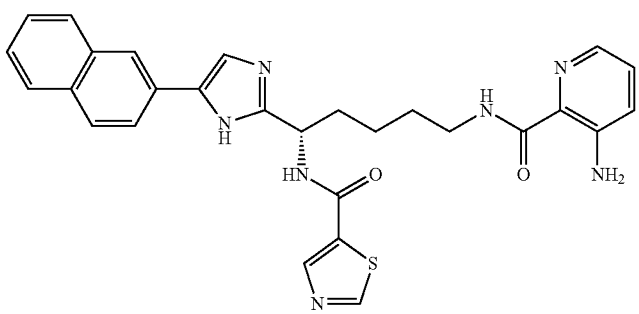 [SMILES: Nc1cccnc1C(=O)NCCCC[C@H](NC(=O)c1cncs1)c1ncc(-c2ccc3ccccc3c2)[nH]1] | (S)-N-(5-(3-aminopicolinamido)-1-(5-(naphthalen-2-yl)-1H-imidazol-2-yl)pentyl)thiazole-5-carboxamide | 527.2 |
| 16 | 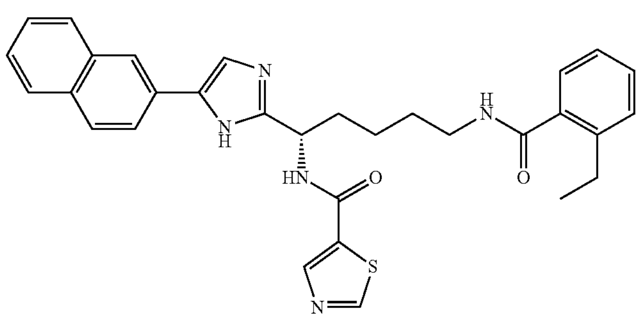 [SMILES: CCc1ccccc1C(=O)NCCCC[C@H](NC(=O)c1cncs1)c1ncc(-c2ccc3ccccc3c2)[nH]1] | (S)-N-(5-(2-ethylbenzamido)-1-(5-(naphthalen-2-yl)-1H-imidazol-2-yl)pentyl)thiazole-5-carboxamide | 539.2 |
| 17 | 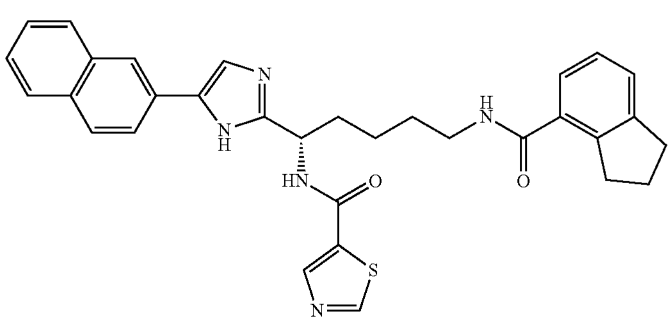 [SMILES: O=C(N[C@@H](CCCCNC(=O)c1cccc2c1CCC2)c1ncc(-c2ccc3ccccc3c2)[nH]1)c1cncs1] | (S)-N-(5-(2,3-dihydro-1H-indene-4-carboxamido)-1-(5-(naphthalen-2-yl)-1H-imidazol-2-yl)pentyl)thiazole-5-carboxamide | 551.2 |

-continued

| Example | Structure | Name | Exact Mass [M + H]+ |
|---|---|---|---|
| 18 | 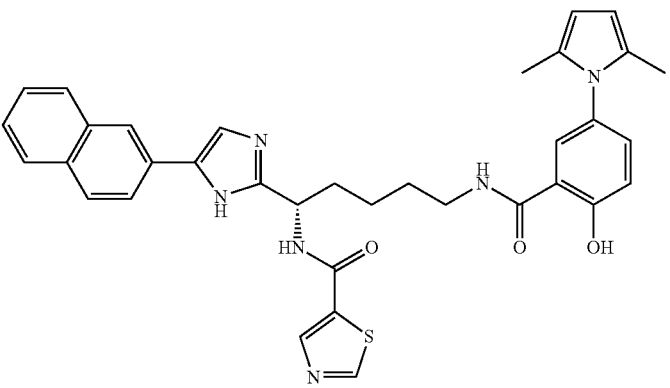 [SMILES: Cc1ccc(C)n1-c1ccc(O)c(C(=O)NCCCC[C@H](NC(=O)c2cncs2)c2ncc(-c3ccc4ccccc4c3)[nH]2)c1] | (S)-N-(5-(5-(2,5-dimethyl-1H-pyrrol-1-yl)-2-hydroxybenzamido)-1-(5-(naphthalen-2-yl)-1H-imidazol-2-yl)pentyl)thiazole-5-carboxamide | 620.2 |
| 19 | 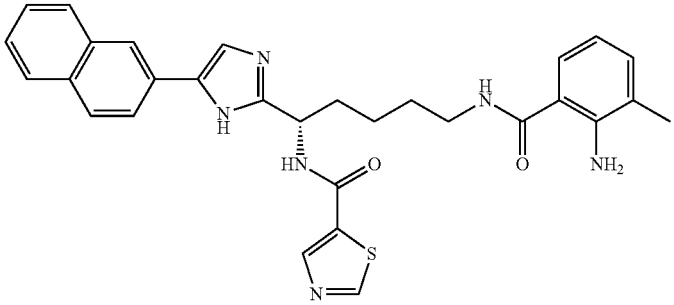 [SMILES: Cc1cccc(C(=O)NCCCC[C@H](NC(=O)c2cncs2)c2ncc(-c3ccc4ccccc4c3)[nH]2)c1N] | (S)-N-(5-(2-amino-3-methylbenzamido)-1-(5-(naphthalen-2-yl)-1H-imidazol-2-yl)pentyl)thiazole-5-carboxamide | 539.1 |
| 20 | 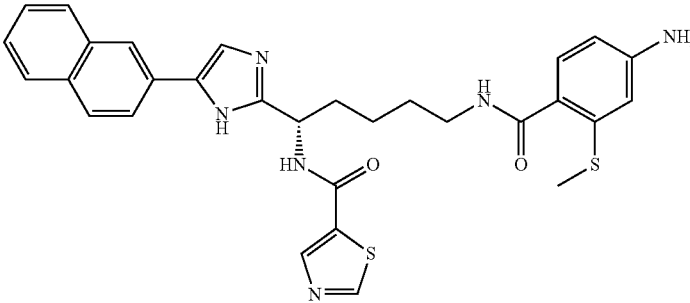 | (S)-N-(5-(4-amino-2-(methylthio)benzamido)-1-(5-(naphthalen-2-yl)-1H-imidazol-2-yl)pentyl)thiazole-5-carboxamide | 572.2 |
| 21 | 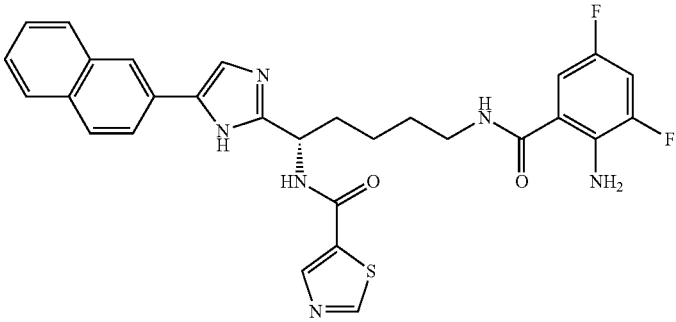 [SMILES: Nc1c(F)cc(F)cc1C(=O)NCCCC[C@H](NC(=O)c1cncs1)c1ncc(-c2ccc3ccccc3c2)[nH]1] | (S)-N-(5-(2-amino-3,5-difluorobenzamido)-1-(5-(naphthalen-2-yl)-1H-imidazol-2-yl)pentyl)thiazole-5-carboxamide | 561.1 |

-continued

| Example | Structure | Name | Exact Mass [M + H]+ |
|---|---|---|---|
| 22 | 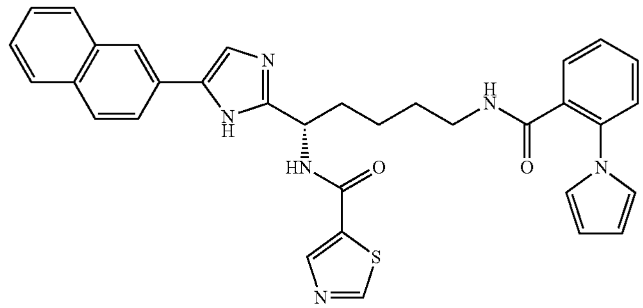 [SMILES: O=C(N[C@@H](CCCCNC(=O)c1ccccc1-n1cccc1)c1ncc(-c2ccc3ccccc3c2)[nH]1)c1cncs1] | (S)-N-(5-(2-(1H-pyrrol-1-yl)benzamido)-1-(5-(naphthalen-2-yl)-1H-imidazol-2-yl)pentyl)thiazole-5-carboxamide | 575.2 |
| 23 | 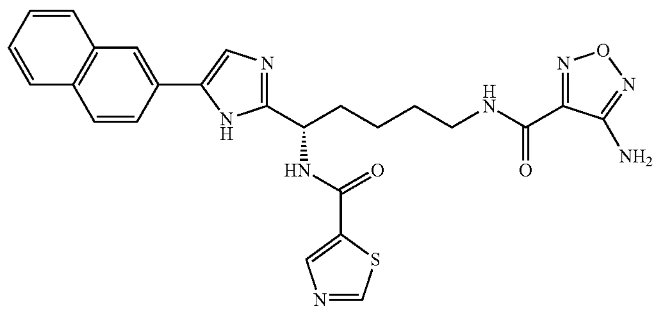 | (S)-4-amino-N-(5-(5-(naphthalen-2-yl)-1H-imidazol-2-yl)-5-(thiazole-5-carboxamido)pentyl)-1,2,5-oxadiazole-3-carboxamide | 518.2 |
| 24 | 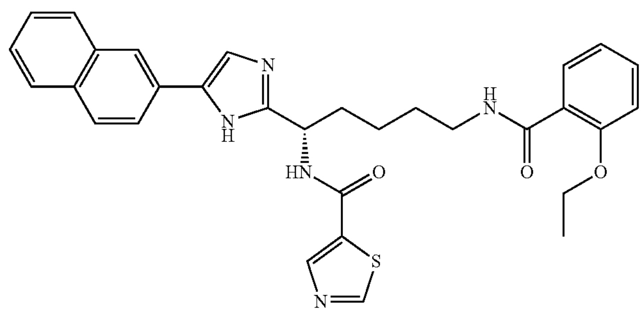 [SMILES: CCOc1ccccc1C(=O)NCCCC[C@H](NC(=O)c1cncs1)c1ncc(-c2ccc3ccccc3c2)[nH]1] | (S)-N-(5-(2-(methoxymethyl)benzamido)-1-(5-(naphthalen-2-yl)-1H-imidazol-2-yl)pentyl)thiazole-5-carboxamide | 555.2 |
| 25 | 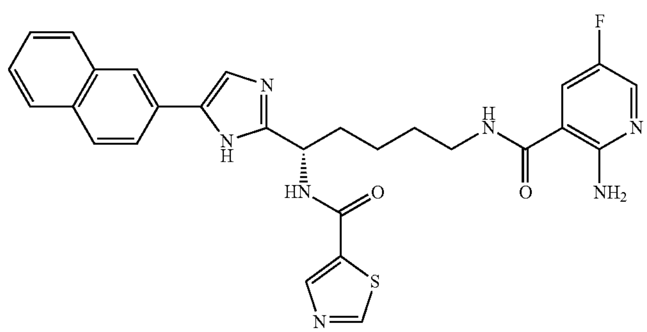 [SMILES: Nc1ncc(F)cc1C(=O)NCCCC[C@H](NC(=O)c1cncs1)c1ncc(-c2ccc3ccccc3c2)[nH]1] | (S)-N-(5-(2-amino-5-fluoronicotinamido)-1-(5-(naphthalen-2-yl)-1H-imidazol-2-yl)pentyl)thiazole-5-carboxamide | 544.2 |
| 26 | 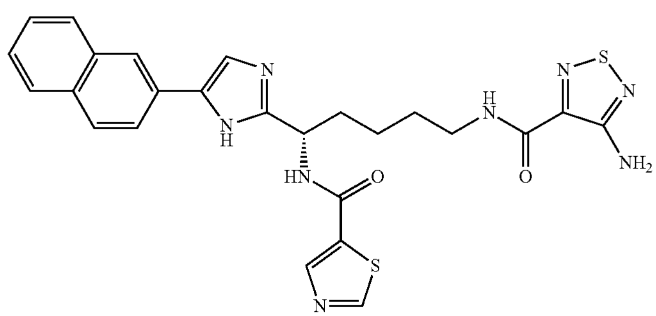 [SMILES: Nc1nsnc1C(=O)NCCCC[C@H](NC(=O)c1cncs1)c1ncc(-c2ccc3ccccc3c2)[nH]1] | (S)-4-amion-N-(5-(5-(naphthalen-2-yl)-1H-imidazol-2-yl)-5-(thiazole-5-carboxamido)pentyl)-1,2,5-thiadiazole-3-carboxamide | 534.2 |

-continued

| Example | Structure | Name | Exact Mass [M + H]⁺ |
|---|---|---|---|
| 27 | 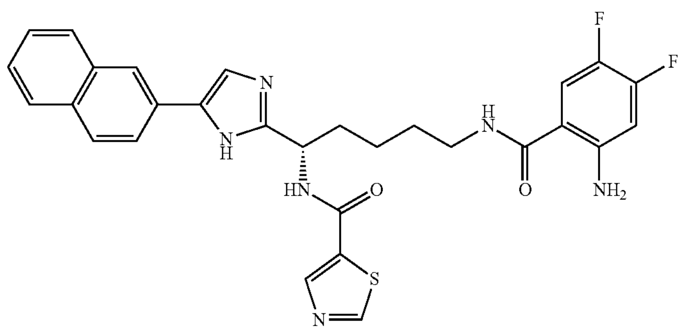 [SMILES: Nc1cc(F)c(F)cc1C(=O)NCCCC[C@H](NC(=O)c1cncs1)c1ncc(-c2ccc3ccccc3c2)[nH]1] | (S)-N-(5-(2-amino-4,5-difluorobenzamido)-1-(5-(naphthalen-2-yl)-1H-imidazol-2-yl)pentyl)thiazole-5-carboxamide | 561.2 |
| 28 | 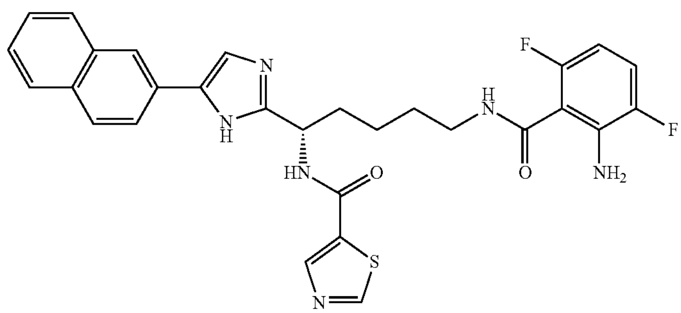 [SMILES: Nc1c(F)ccc(F)c1C(=O)NCCCC[C@H](NC(=O)c1cncs1)c1ncc(-c2ccc3ccccc3c2)[nH]1] | (S)-N-(5-(2-amino-3,6-difluorobenzamido)-1-(5-(naphthalen-2-yl)-1H-imidazol-2-yl)pentyl)thiazole-5-carboxamide | 561.2 |
| 29 | 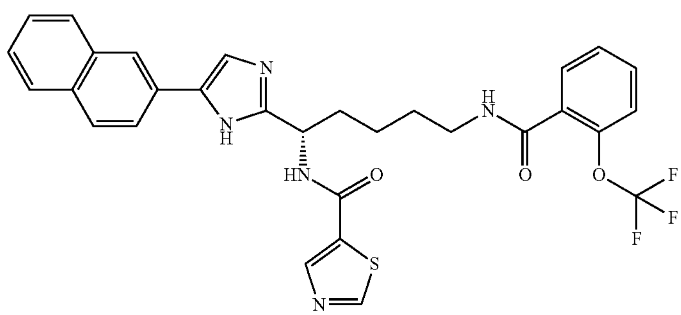 [SMILES: O=C(N[C@@H](CCCCNC(=O)c1ccccc1OC(F)(F)F)c1ncc(-c2ccc3ccccc3c2)[nH]1)c1cncs1] | (S)-N-(1-(5-(naphthalen-2-yl)-1H-imidazol-2-yl)-5-(2-(trifluoromethoxy)benzamido)pentyl)thiazole-5-carboxamide | 595.2 |
| 30 | 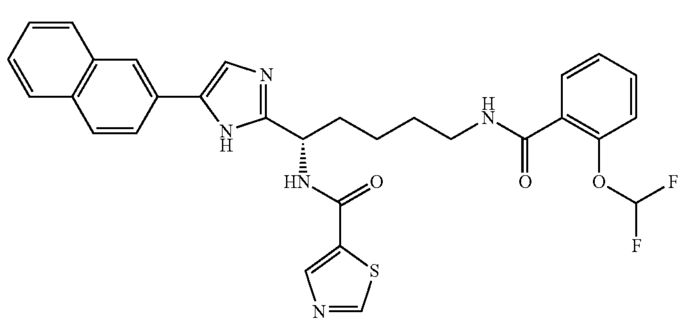 [SMILES: O=C(N[C@@H](CCCCNC(=O)c1ccccc1OC(F)F)c1ncc(-c2ccc3ccccc3c2)[nH]1)c1cncs1] | (S)-N-(5-(2-(difluoromethoxy)benzamido)-1-(5-(naphthalen-2-yl)-1H-imidazol-2-yl)pentyl)thiazole-5-carboxamide | 577.2 |

-continued

| Example | Structure | Name | Exact Mass [M + H]+ |
|---|---|---|---|
| 31 | 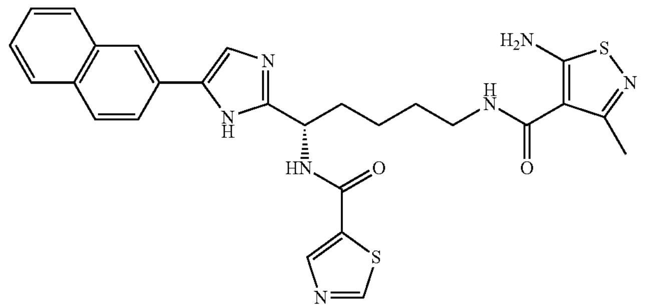 [SMILES: Cc1nsc(N)c1C(=O)NCCCC[C@H](NC(=O)c1cncs1)c1ncc(-c2ccc3ccccc3c2)[nH]1] | (S)-5-amino-3-methyl-N-(5-(5-(naphthalen-2-yl)-1H-imidazol-2-yl)-5-(thiazole-5-carboxamido)pentyl)isothiazole-4-carboxamide | 547.2 |
| 32 | 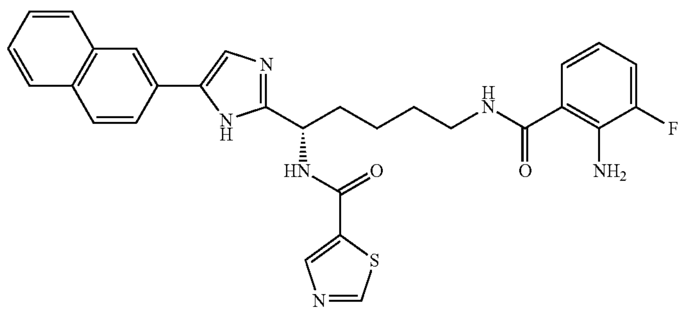 [SMILES: Nc1c(F)cccc1C(=O)NCCCC[C@H](NC(=O)c1cncs1)c1ncc(-c2ccc3ccccc3c2)[nH]1] | (S)-N-(5-(2-amino-3-fluorobenzamido)-1-(5-(naphthalen-2-yl)-1H-imidazol-2-yl)pentyl)thiazole-5-carboxamide | 543.2 |
| 33 | 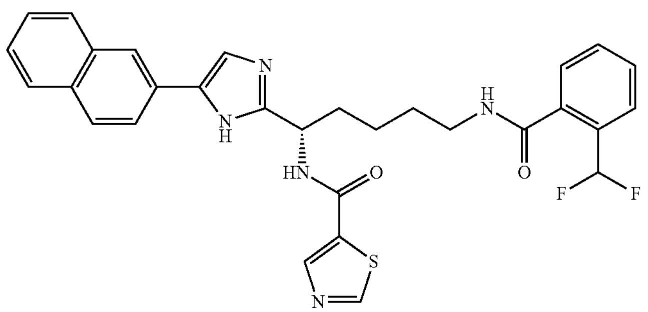 [SMILES: O=C(N[C@@H](CCCCNC(=O)c1ccccc1C(F)F)c1ncc(-c2ccc3ccccc3c2)[nH]1)c1cncs1] | (S)-N-(5-(2-(difluoromethyl)benzamido)-1-(5-(naphthalen-2-yl)-1H-imidazol-2-yl)pentyl)thiazole-5-carboxamide | 561.2 |
| 34 | 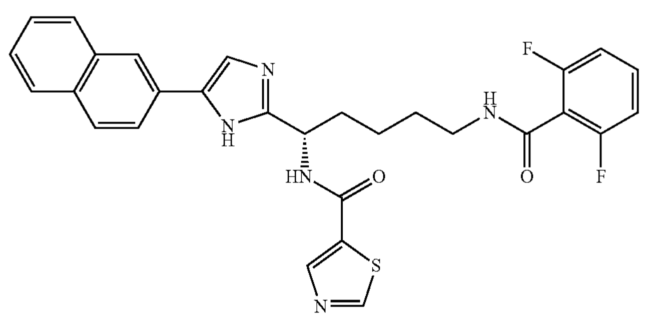 [SMILES: O=C(N[C@@H](CCCCNC(=O)c1c(F)cccc1F)c1ncc(-c2ccc3ccccc3c2)[nH]1)c1cncs1] | (S)-N-(5-(2,6-difluorobenzamido)-1-(5-(naphthalen-2-yl)-1H-imidazol-2-yl)pentyl)thiazole-5-carboxamide | 547.2 |
| 35 | 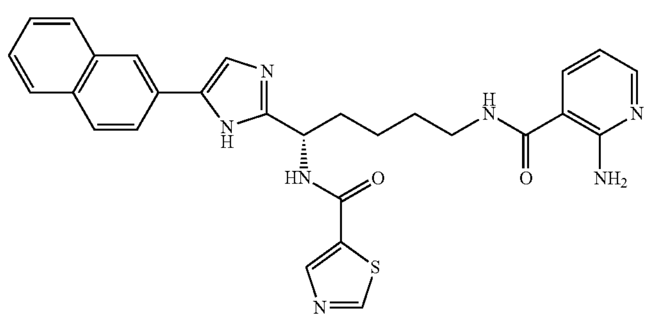 [SMILES: Nc1ncccc1C(=O)NCCCC[C@H](NC(=O)c1cncs1)c1ncc(-c2ccc3ccccc3c2)[nH]1] | (S)-N-(5-(2-aminonicotinamido)-1-(5-(naphthalen-2-yl)-1H-imidazol-2-yl)pentyl)thiazole-5-carboxamide | 527.1 |

| Example | Structure | Name | Exact Mass [M + H]+ |
|---|---|---|---|
| 36 | 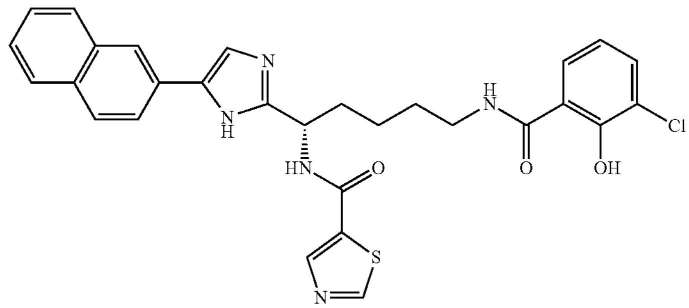 [SMILES: O=C(N[C@@H](CCCCNC(=O)c1cccc(Cl)c1O)c1ncc(-c2ccc3ccccc3c2)[nH]1)c1cncs1] | (S)-N-(5-(3-chloro-2-hydroxybenzamido)-1-(5-(naphthalen-2-yl)-1H-imidazol-2-yl)pentyl)thiazole-5-carboxamide | 561.2 |
| 37 | 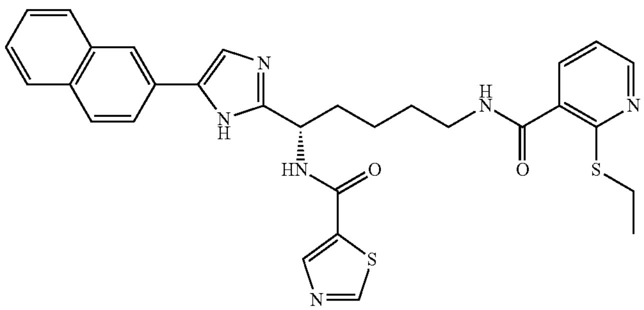 [SMILES: CCSc1ncccc1C(=O)NCCCC[C@H](NC(=O)c1cncs1)c1ncc(-c2ccc3ccccc3c2)[nH]1] | (S)-N-(5-(2-(ethylthio)nicotinamido)-1-(5-(naphthalen-2-yl)-1H-imidazol-2-yl)pentyl)thiazole-5-carboxamide | 572.2 |
| 38 | 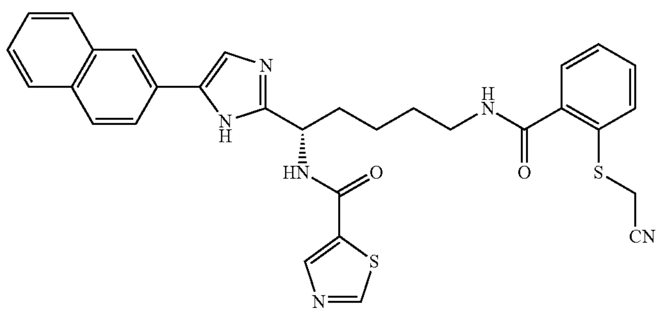 [SMILES: N#CCSc1ccccc1C(=O)NCCCC[C@H](NC(=O)c1cncs1)c1ncc(-c2ccc3ccccc3c2)[nH]1] | (S)-N-(5-(2-((cyanomethyl)thio)benzamido)-1-(5-(naphthalen-2-yl)-1H-imidazol-2-yl)pentyl)thiazole-5-carboxamide | 582.1 |
| 39 | 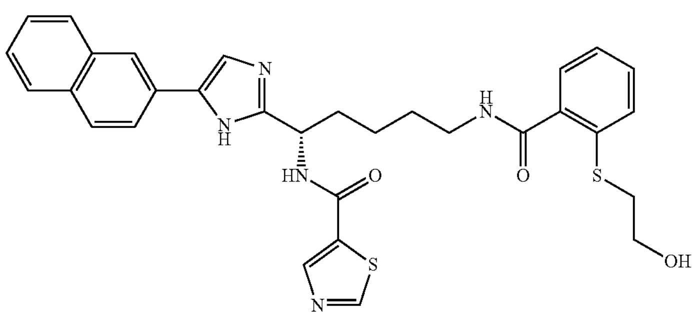 [SMILES: O=C(N[C@@H](CCCCNC(=O)c1ccccc1SCCO)c1ncc(-c2ccc3ccccc3c2)[nH]1)c1cncs1] | (S)-N-(5-(2-((2-hydroxyethyl)thio)benzamido)-1-(5-(naphthalen-2-yl)-1H-imidazol-2-yl)pentyl)thiazole-5-carboxamide | 587.2 |
| 40 | 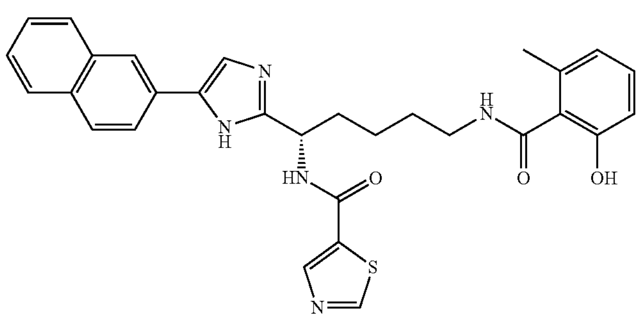 [SMILES: Cc1cccc(O)c1C(=O)NCCCC[C@H](NC(=O)c1cncs1)c1ncc(-c2ccc3ccccc3c2)[nH]1] | (S)-N-(5-(2-hydroxy-6-methylbenzamido)-1-(5-(naphthalen-2-yl)-1H-imidazol-2-yl)pentyl)thiazole-5-carboxamide | 539.2 |

-continued

| Example | Structure | Name | Exact Mass [M + H]+ |
|---|---|---|---|
| 41 | 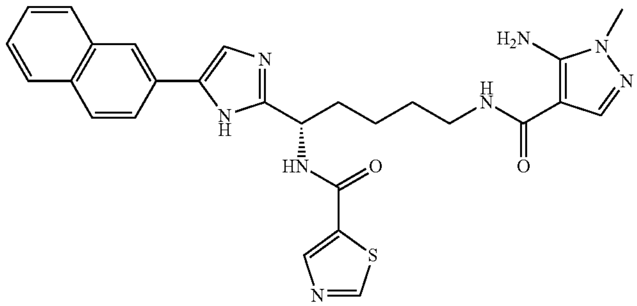 [SMILES: Cn1ncc(C(=O)NCCCC[C@H](NC(=O)c2cncs2)c2ncc(-c3ccc4ccccc4c3)[nH]2)c1N] | (S)-N-(5-(5-amino-1-methyl-1H-pyrazole-4-carboxamido)-1-(5-(naphthalen-2-yl)-1H-imidazol-2-yl)pentyl)thiazole-5-carboxamide | 529.2 |
| 42 | 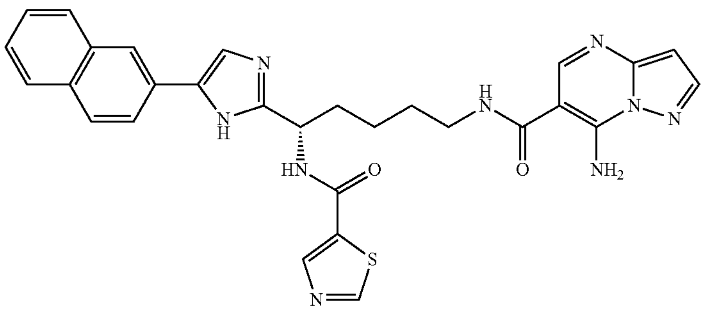 [SMILES: Nc1c(C(=O)NCCCC[C@H](NC(=O)c2cncs2)c2ncc(-c3ccc4ccccc4c3)[nH]2)cnc2ccnn12] | (S)-N-(5-(7-aminopyrazolo[1,5-a]pyrimidine-6-carboxamido)-1-(5-(naphthalen-2-yl)-1H-imidazol-2-yl)pentyl)thiazole-5-carboxamide | 566.2 |
| 43 | 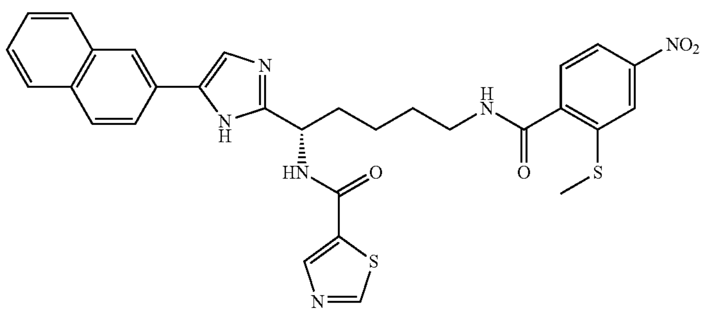 [SMILES: CSc1cc([N+](=O)[O-])ccc1C(=O)NCCCC[C@H](NC(=O)c1cncs1)c1ncc(-c2ccc3ccccc3c2)[nH]1] | (S)-N-(5-(2-(methylthio)-4-nitrobenzamido)-1-(5-(naphthalen-2-yl)-1H-imidazol-2-yl)pentyl)thiazole-5-carboxamide | 602.2 |
| 44 | 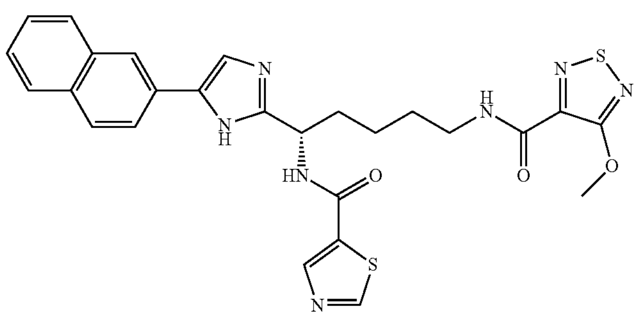 [SMILES: COc1nsnc1C(=O)NCCCC[C@H](NC(=O)c1cncs1)c1ncc(-c2ccc3ccccc3c2)[nH]1] | (S)-4-methoxy-N-(5-(5-(naphthalen-2-yl)-1H-imidazol-2-yl)-5-(thiazole-5-carboxamido)pentyl)-1,2,5-thiadiazole-3-carboxamide | 549.2 |
| 45 | 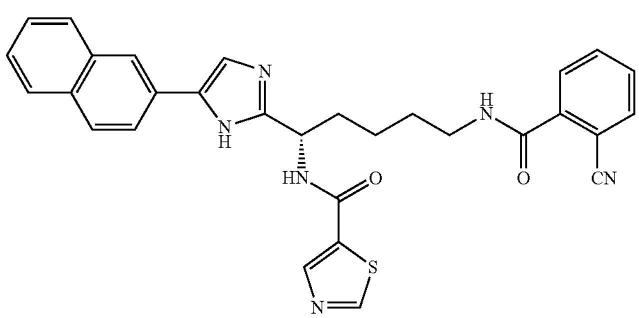 [SMILES: N#Cc1ccccc1C(=O)NCCCC[C@H](NC(=O)c1cncs1)c1ncc(-c2ccc3ccccc3c2)[nH]1] | (S)-N-(5-(2-cyanobenzamido)-1-(5-(naphthalen-2-yl)-1H-imidazol-2-yl)pentyl)thiazole-5-carboxamide | 536.2 |

-continued

| Example | Structure | Name | Exact Mass [M + H]+ |
|---|---|---|---|
| 46 | 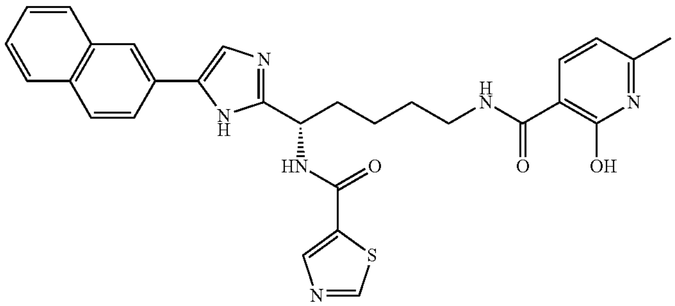 [SMILES: Cc1ccc(C(=O)NCCCC[C@H](NC(=O)c2cncs2)c2ncc(-c3ccc4ccccc4c3)[nH]2)c(O)n1] | (S)-N-(5-(2-hydroxy-6-methylnicotinamido)-1-(5-(naphthalen-2-yl)-1H-imidazol-2-yl)pentyl)thiazole-5-carboxamide | 540.2 |
| 47 | 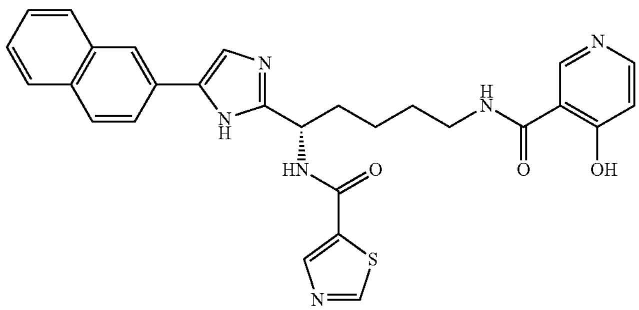 [SMILES: O=C(N[C@@H](CCCCNC(=O)c1cnccc1O)c1ncc(-c2ccc3ccccc3c2)[nH]1)c1cncs1] | (S)-N-(5-(4-hydroxynicotinamido)-1-(5-(naphthalen-2-yl)-1H-imidazol-2-yl)pentyl)thiazole-5-carboxamide | 526.2 |
| 48 | 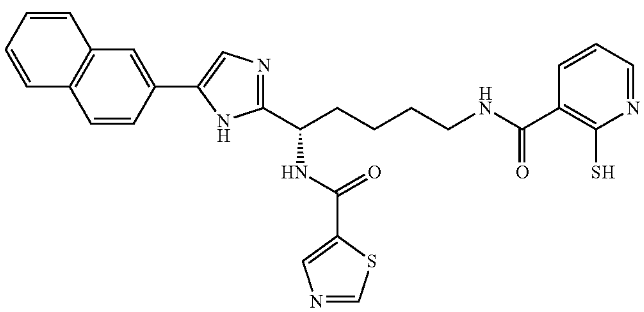 [SMILES: O=C(N[C@@H](CCCCNC(=O)c1cccnc1S)c1ncc(-c2ccc3ccccc3c2)[nH]1)c1cncs1] | (S)-N-(5-(2-mercaptonicotinamido)-1-(5-(naphthalen-2-yl)-1H-imidazol-2-yl)pentyl)thiazole-5-carboxamide | 544.2 |
| 49 | 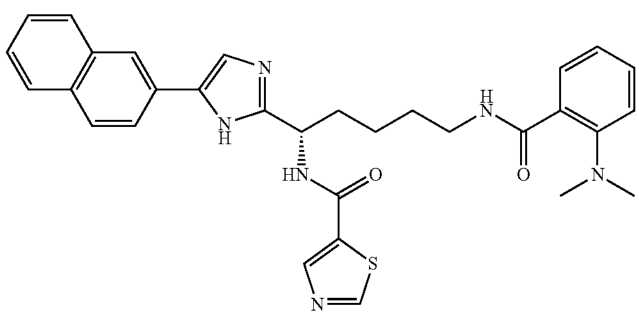 [SMILES: CN(C)c1ccccc1C(=O)NCCCC[C@H](NC(=O)c1cncs1)c1ncc(-c2ccc3ccccc3c2)[nH]1] | (S)-N-(5-(2-(dimethylamino)benzamido)-1-(5-(naphthalen-2-yl)-1H-imidazol-2-yl)pentyl)thiazole-5-carboxamide | 553.2 |
| 50 | 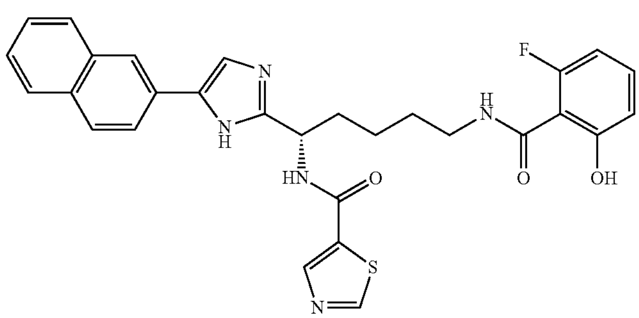 [SMILES: O=C(N[C@@H](CCCCNC(=O)c1c(O)cccc1F)c1ncc(-c2ccc3ccccc3c2)[nH]1)c1cncs1] | (S)-N-(5-(2-fluoro-6-hydroxybenzamido)-1-(5-(naphthalen-2-yl)-1H-imidazol-2-yl)pentyl)thiazole-5-carboxamide | 544.2 |

Example 51

(S)-N-(1-(5-(2-methoxyquinolin-3-yl)-1H-imidazol-2-yl)-5-(2-(methylthio)benzamido)pentyl)thiazole-5-carboxamide

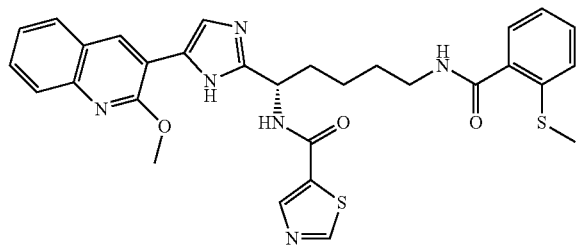 [SMILES: COc1nc2ccccc2cc1-c1cnc([C@H](CCCCNC(=O)c2ccccc2SC)NC(=O)c2cncs2)[nH]1]

Step 1: (S)-2-(2-methoxyquinolin-3-yl)-2-oxoethyl 2-(((benzyloxy)carbonyl)amino)-6-((tert-butoxycarbonyl)amino)hexanoate (S)-2-(((benzyloxy)carbonyl)amino)-6-((tert-butoxycarbonyl)amino)hexanoic acid (3503 mg, 9.21 mmol), EDC (2471 mg, 12.89 mmol), and HOBT (1742 mg, 12.89 mmol) were dissolved in DMF. After stirring for 5 min, 2-hydroxy-1-(2-methoxyquinolin-3-yl)ethanone (2000 mg, 9.21 mmol) and DMAP (337 mg, 2.76 mmol) were added. The reaction mixture was then allowed to stir at room temperature under constant flow of $N_2$ overnight. The solvent was then evaporated and crude partitioned between DCM and water. The organic phase was dried ($Na_2SO_4$), filtered and concentrated under vacuum/high vacuum to give a crude residue, which was column purified eluting with 30% EtOAc/Hexane to afford (S)-2-(2-methoxyquinolin-3-yl)-2-oxoethyl 2-(((benzyloxy)carbonyl)amino)-6-((tert-butoxycarbonyl)amino)hexanoate. LCMS (ESI) calc'd for $C_{31}H_{37}N_3O_8$ [M+H]$^+$: 580.1, found: 580.1.

Step 2: (S)-benzyl tert-butyl (1-(5-(2-methoxyquinolin-3-yl)-1H-imidazol-2-yl)pentane-1,5-diyl)dicarbamate A solution of (S)-2-(2-methoxyquinolin-3-yl)-2-oxoethyl 2-(((benzyloxy)carbonyl)amino)-6-((tert-butoxycarbonyl)amino)hexanoate (4.5 g, 7.76 mmol) and ammonium acetate (3.58 ml, 54.3 mmol) in toluene (40 ml) was stirred at 120° C. in a pressure vessel for 3 hours. The reaction mixture was cooled to room temperature and diluted with EtOAc (100 ml) and satd. $NaHCO_3$ (50 ml). The organic phase was separated and the aqueous phase was further extracted with EtOAc (2×50 mL). The combined organic phase was dried over anhydrous $Na_2SO_4$, filtered and the solvent was evaporated to afford the crude product, which was column purified eluting with 30-40% EtOAc/Hexanes to afford (S)-benzyl tert-butyl (1-(5-(2-methoxyquinolin-3-yl)-1H-imidazol-2-yl)pentane-1,5-diyl)dicarbamate. LCMS (ESI) calc'd for $C_{31}H_{37}N_5O_5$ [M+H]$^+$: 560.1, found: 560.2.

Step 3: (S)-tert-butyl (5-amino-5-(5-(2-methoxyquinolin-3-yl)-1H-imidazol-2-yl)pentyl)carbamate To a solution of (S)-benzyl tert-butyl (1-(5-(2-methoxyquinolin-3-yl)-1H-imidazol-2-yl)pentane-1,5-diyl)dicarbamate (1.3 g, 2.323 mmol) in methanol at ambient temperature was added Pd/C (0.494 g, 0.232 mmol). A balloon full of $H_2$ was added to the reaction vessel (vacuum purged 3×) and the mixture was allowed to stir for 6 hours. The resulting mixture was filtered and the filtrate was concentrated to obtain a crude residue (S)-tert-butyl (5-amino-5-(5-(2-methoxyquinolin-3-yl)-1H-imidazol-2-yl)pentyl)carbamate, which was used as it is without further purification. LCMS (ESI) calc'd for $C_{23}H_{31}N_5O_3$ [M+H]$^+$: 426.1, found: 426.1.

Step 4: (S)-tert-butyl (5-(5-(2-methoxyquinolin-3-yl)-1H-imidazol-2-yl)-5-(thiazole-5-carboxamido)pentyl)carbamate To (S)-tert-butyl (5-amino-5-(5-(2-methoxyquinolin-3-yl)-1H-imidazol-2-yl)pentyl)carbamate (950 mg, 2.233 mmol) in DMF was added thiazole-5-carboxylic acid (288 mg, 2.233 mmol), and the mixture was cooled to 0° C. in an ice bath. HATU (1104 mg, 2.90 mmol) was slowly added to the mixture, followed sequentially by triethylamine (0.935 ml, 6.70 mmol). The reaction was stirred at 25° C. for 30 minutes and then quenched with sat. $NaHCO_3$ (5 mL) and extracted with EtOAc (3×20 mL). The combined organic phase was washed with sat. NaCl (2×10 mL), dried over anhydrous $Na_2SO_4$ and concentrated to dryness under vacuum to give a crude residue. The desired product was isolated through column purification on silica gel eluting with (50-80% EtOAc/Hexanes) to afford (S)-tert-butyl (5-(5-(2-methoxyquinolin-3-yl)-1H-imidazol-2-yl)-5-(thiazole-5-carboxamido)pentyl)carbamate. LCMS (ESI) calc'd for $C_{27}H_{32}N_6O_4S$ [M+H]$^+$: 537.1, found: 537.1.

Step 5: (S)-N-(5-amino-1-(5-(2-methoxyquinolin-3-yl)-1H-imidazol-2-yl)pentyl)thiazole-5-carboxamide (S)-tert-butyl (5-(5-(2-methoxyquinolin-3-yl)-1H-imidazol-2-yl)-5-(thiazole-5-carboxamido) pentyl)carbamate (1.15 g, 2.143 mmol) was dissolved in DCM followed by slow addition of trifluoroacetic acid (4 ml, 2.143 mmol) at room temperature. The reaction mixture was stirred at room temperature for 2 hours and then concentrated under vacuum to give a crude residue, which was column purified eluting with (5% 2N $NH_3$, MeOH/DCM) to afford (S)-N-(5-amino-1-(5-(2-methoxyquinolin-3-yl)-1H-imidazol-2-yl)pentyl)thiazole-5-carboxamide. LCMS (ESI) calc'd for $C_{22}H_{24}N_6O_2S$ [M+H]$^+$: 437.1, found: 437.1.

Step 6: (S)-N-(1-(5-(2-methoxyquinolin-3-yl)-1H-imidazol-2-yl)-5-(2-(methylthio)benzamido) pentyl)thiazole-5-carboxamide To a solution of (S)-N-(5-amino-1-(5-(2-methoxyquinolin-3-yl)-1H-imidazol-2-yl)pentyl)thiazole-5-carboxamide (70 mg, 0.160 mmol) and 2-(methylthio)benzoic acid (28.3 mg, 0.168 mmol) in DMF was added 4-methylmorpholine (0.071 ml, 0.641 mmol) and the mixture was stirred for 5 minutes. 1-hydroxybenzotriazole hydrate (29.5 mg, 0.192 mmol) and 1-(3-dimethylaminopropyl)-2-ethylcarbodiimide hydrochloride (36.9 mg, 0.192 mmol) were then added and the mixture was allowed to stir for 2 hours under constant flow of $N_2$ gas. Upon completion the mixture was diluted with DMF (6 mL), filtered and purified using the mass directed reverse phase HPLC purification system (using $CH_3CN$:$H_2O$, TFA system) to isolate (S)-N-(1-(5-(2-methoxyquinolin-3-yl)-1H-imidazol-2-yl)-5-(2-(methylthio)benzamido)pentyl)thiazole-5-carboxamide. LCMS (ESI) calc'd for $C_{30}H_{30}N_6O_3S_2$ [M+H]$^+$: 587.2, found: 587.1.

$^1$H NMR (500 MHz, CD$_3$OD) δ 9.10 (s, 1H), 8.60 (s, 1H), 8.53 (s, 1H), 7.94 (s, 1H), 7.87 (d, J=7.5 Hz, 2H), 7.72 (t, J=5.5 Hz, 1H), 7.51 (t, J=5.6 Hz, 1H), 7.21-7.35 (m, 3H), 7.09 (t, 5.0 Hz, 1H), 5.39 (t, J=5.5 Hz, H), 4.19 (s, 3H), 3.43 (t, 6.0 Hz, 2H), 2.17 (s, 3H), 2.14-2.37 (m, 2H), 1.70-1.80 (m, 2H), 1.52-1.76 (m, 2H) ppm.

Using similar methodology as described in Example 51, the following examples were prepared using the appropriate starting materials:

| Example | Structure | Name | Exact Mass [M + H]$^+$ |
|---|---|---|---|
| 52 | 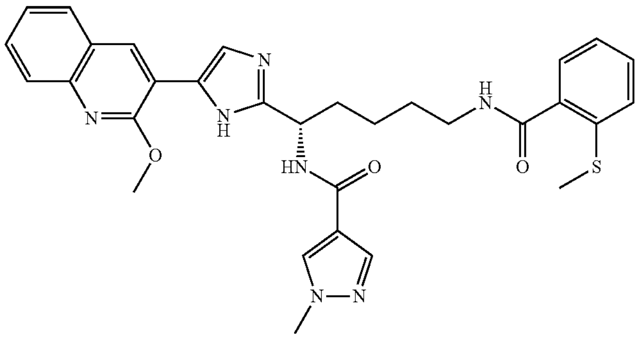 [SMILES: COc1nc2ccccc2cc1-c1cnc([C@H](CCCCNC(=O)c2ccccc2SC)NC(=O)c2cnn(C)c2)[nH]1] | (S)-N-(1-(5-(2-methoxyquinolin-3-yl)-1H-imidazol-2-yl)-5-(2-(methylthio)benzamido)pentyl)-1-methyl-1H-pyrazole-4-carboxamide | 584.3 |
| 53 | 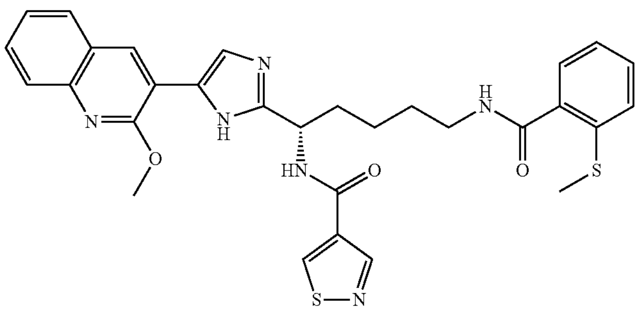 [SMILES: COc1nc2ccccc2cc1-c1cnc([C@H](CCCCNC(=O)c2ccccc2SC)NC(=O)c2cnsc2)[nH]1] | ((S)-N-(1-(5-(2-methoxyquinolin-3-yl)-1H-imidazol-2-yl)-5-(2-(methylthio)benzamido)pentyl)isothiazole-4-carboxamide | 587.4 |
| 54 | 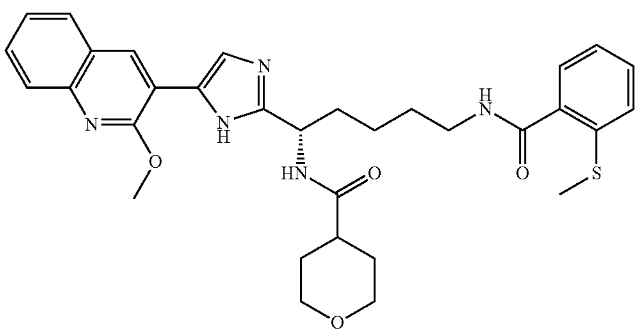 [SMILES: COc1nc2ccccc2cc1-c1cnc([C@H](CCCCNC(=O)c2ccccc2SC)NC(=O)C2CCOCC2)[nH]1] | (S)-N-(1-(5-(2-methoxyquinolin-3-yl)-1H-imidazol-2-yl)-5-(2-(methylthio)benzamido)pentyl)tetrahydro-2H-pyrazol-4-carboxamide | 588.3 |
| 55 | 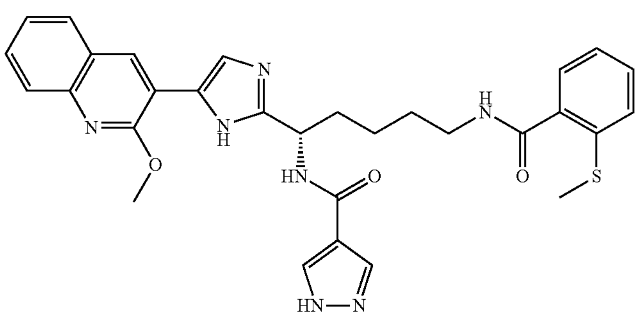 [SMILES: COc1nc2ccccc2cc1-c1cnc([C@H](CCCCNC(=O)c2ccccc2SC)NC(=O)c2cn[nH]c2)[nH]1] | (S)-N-(1-(5-(2-methoxyquinolin-3-yl)-1H-imidazol-2-yl)-5-(2-(methylthio)benzamido)pentyl)-1H-pyrazole-4-carboxamide | 570.1 |

| Example | Structure | Name | Exact Mass [M + H]+ |
|---|---|---|---|
| 56 | 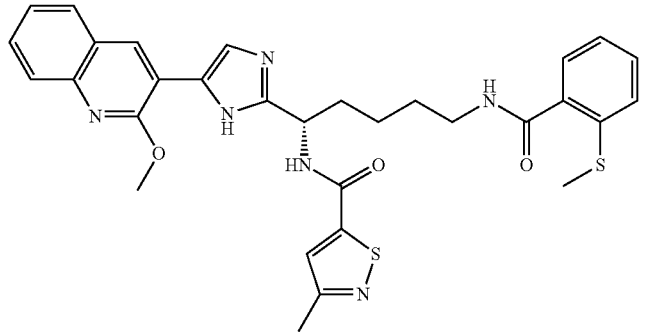 [SMILES: COc1nc2ccccc2cc1-c1cnc([C@H](CCCCNC(=O)c2ccccc2SC)NC(=O)c2cc(C)ns2)[nH]1] | (S)-N-(1-(5-(2-methoxyquinolin-3-yl)-1H-imidazol-2-yl)-5-(2-(methylthio)benzamido)pentyl)-3-methylisothiazole-5-carboxamide | 601.4 |
| 57 | 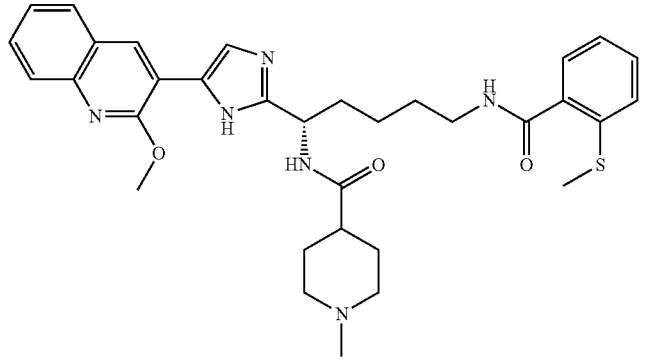 [SMILES: COc1nc2ccccc2cc1-c1cnc([C@H](CCCCNC(=O)c2ccccc2SC)NC(=O)C2CCN(C)CC2)[nH]1] | (S)-N-(1-(5-(2-methoxyquinolin-3-yl)-1H-imidazol-2-yl)-5-(2-(methylthio)benzamido)pentyl)-1-methylpiperidine-4-carboxamide | 601.4 |
| 58 | 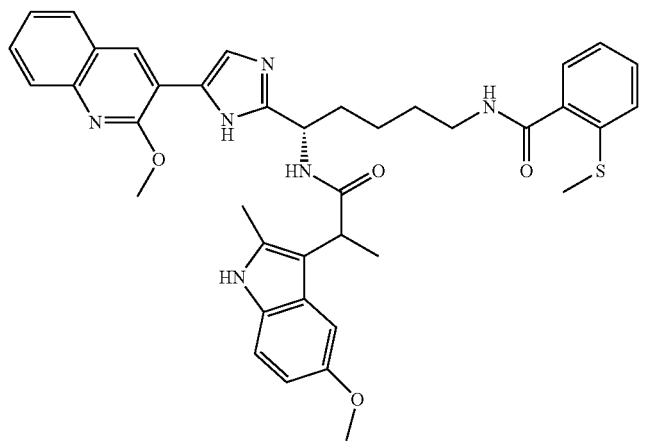 [SMILES: COc1ccc2[nH]c(C)c(C(C)C(=O)N[C@@H](CCCCNC(=O)c3ccccc3SC)c3ncc(-c4cc5ccccc5nc4OC)[nH]3)c2c1] | N-((5S)-5-(2-(5-methoxy-2-methyl-1H-indol-3-yl)propanamido)-5-(5-(2-methoxyquinolin-3-yl)-1H-imidazol-2-yl)pentyl)-2-(methylthio)benzamide | 691.5 |
| 59 | 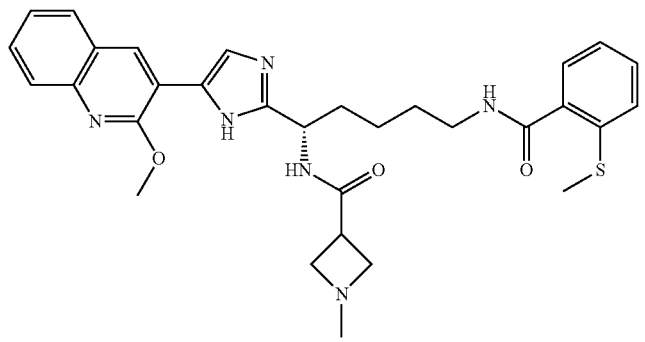 [SMILES: COc1nc2ccccc2cc1-c1cnc([C@H](CCCCNC(=O)c2ccccc2SC)NC(=O)C2CN(C)C2)[nH]1] | (S)-N-(1-(5-(2-methoxyquinolin-3-yl)-1H-imidazol-2-yl)-5-(2-(methylthio)benzamido)pentyl)-1-methylazetidine-3-carboxamide | 573.4 |

| Example | Structure | Name | Exact Mass [M + H]+ |
|---|---|---|---|
| 60 | 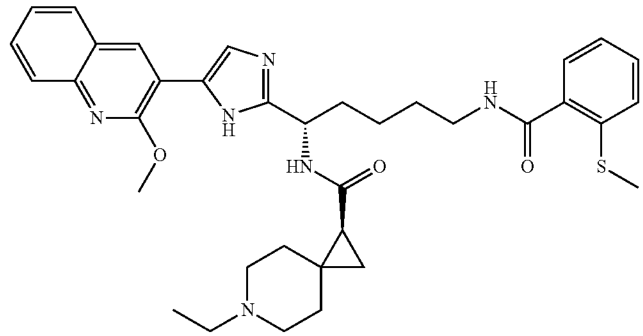 [SMILES: CCN1CCC2(CC1)C[C@@H]2C(=O)N[C@@H](CCCCNC(=O)c1ccccc1SC)c1ncc(-c2cc3ccccc3nc2OC)[nH]1] | (S)-6-ethyl-N-((S)-1-(5-(2-methoxyquinolin-3-yl)-1H-imidazol-2-yl)-5-(2-(methylthio)benzamido)pentyl)-6-azaspiro[2.5]octane-1-carboxamide | 641.2 |
| 61 | 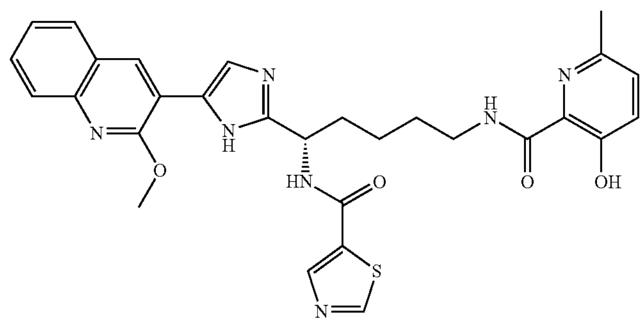 [SMILES: COc1nc2ccccc2cc1-c1cnc([C@H](CCCCNC(=O)c2nc(C)ccc2O)NC(=O)c2cncs2)[nH]1] | (S)-N-(5-(3-hydroxy-6-methylpicolinamido)-1-(5-(2-methoxyquinolin-3-yl)-1H-imidazol-2-yl)pentyl)thiazole-5-carboxamide | 573.4 |

Example 62

N-(4-(2-(5-(2-methoxyquinolin-3-yl)-1H-imidazol-2-yl)-5-oxopyrrolidin-2-yl)butyl)-2-(methylthio)benzamide

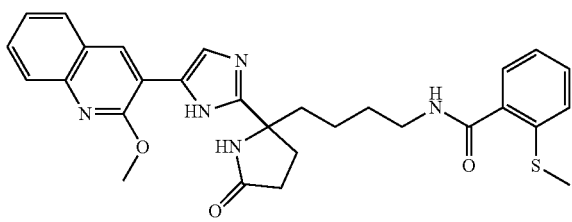 [SMILES: COc1nc2ccccc2cc1-c1cnc(C2(CCCCNC(=O)c3ccccc3SC)CCC(=O)N2)[nH]1]

Step 1: 2-(2-methoxyquinolin-3-yl)-2-oxoethyl 2-allyl-5-oxopyrrolidine-2-carboxylate In a 25 mL one neck round bottom flask, 1-(3-dimethylaminopropyl)-3-ethylcarbodiimide hydrochloride (250 mg, 1.304 mmol) and 1-hydroxybenzotriazole hydrate (200 mg, 1.306 mmol) were added to a solution of 2-allyl-5-oxopyrrolidine-2-carboxylic acid (200 mg, 1.182 mmol) in DMF (2 ml). The reaciton mixture was stirred for 5 minutes. Then, 2-hydroxy-1-(2-methoxyquinolin-3-yl)ethanone (270 mg, 1.243 mmol) was added, followed by 4-DMAP (10 mg, 0.082 mmol). The reaction mixture was then stirred for 2 hours at room temp. The reaction mixture was worked up with EtOAc (40 ml) and H$_2$O (15 ml). The organic layer was separated, dried over Na$_2$SO$_4$, filtered and concentrated to provide 2-(2-methoxyquinolin-3-yl)-2-oxoethyl 2-allyl-5-oxopyrrolidine-2-carboxylate which was used without further purification in the next step. LCMS (ESI) calc'd for C$_{20}$H$_{20}$N$_2$O$_5$ [M+H]+: 369.1, found: 369.2.

Step 2: 5-allyl-5-(5-(2-methoxyquinolin-3-yl)-1H-imidazol-2-yl)pyrrolidin-2-one To a 50 mL pressure vessel flask was added a solution of 2-(2-methoxyquinolin-3-yl)-2-oxoethyl 2-allyl-5-oxopyrrolidine-2-carboxylate (430 mg, 0.817 mmol) and ammonium acetate (800 mg, 10.38 mmol) in toluene (10 mL) at 100° C. for 3 hours. After it was cooled to room temp, the mixture was diluted with EtOAc (50 mL) and saturated NaHCO$_3$ (20 mL). The organic layer was separated, dried over Na$_2$SO$_4$, filtered and concentrated. The crude product was purified on Analogix (24 g Redisep column) eluting with 7% MeOH/MeCl$_2$/NH$_4$OH yielding 5-allyl-5-(5-(2-methoxyquinolin-3-yl)-1H-imidazol-2-yl)pyrrolidin-2-one. LCMS (ESI) calc'd for C$_{20}$H$_{20}$N$_4$O$_2$ [M+H]+: 349.1, found: 349.2.

Step 3: tert-butyl 2-(2-allyl-5-oxopyrrolidin-2-yl)-5-(2-methoxyquinolin-3-yl)-1H-imidazole-1-carboxylate To a 25 mL one-necked round bottom flask, a solution of di-tert-butyl dicarbonate (188 mg, 0.861 mmol) in DCM (2 ml) was added to a solution of 5-allyl-5-(5-(2-methoxyquinolin-3-yl)-1H-imidazol-2-yl)pyrrolidin-2-one (300 mg, 0.861 mmol) in DCM (3 ml), followed by DMAP (5 mg). The reaction mixture was stirred for 0.5 hour, then the mixture was chromatographed directly on Analogix (12 g RediSep column) eluting with 1/1 EtOAc-Hexanes yielding tert-butyl 2-(2-allyl-5-oxopyrrolidin-2-yl)-5-(2-methoxyquinolin-3-yl)-1H-imidazole-1-carboxylate. LCMS (ESI) calc'd for C$_{25}$H$_{28}$N$_4$O$_4$ [M+H]+: 449.2, found: 449.3.

Step 4: (E)-2-(2-(4-(bis(tert-butoxycarbonyl)amino)but-2-en-1-yl)-5-oxopyrrolidin-2-yl)-5-(2-methoxyquinolin-3-yl)-1H-imidazole-1-carboxylate To a 50 mL one-necked round bottom flask was added toluene (2 ml) along with tert-butyl 2-(2-allyl-5-oxopyrrolidin-2-yl)-5-(2-methoxyquinolin-3-yl)-1H-imidazole-1-carboxylate (200 mg, 0.446 mmol), N,N-DiBoc-allylamine (230 mg, 0.894 mmol) and M71-S1PR (20 mg, 0.024 mmol). The system was degassed and refilled with nitrogen. The reaction mixture was then stirred for 2 hours under nitrogen at 60° C. The reaction mixture was loaded directly to a MPLC column and purified, eluting with 1/1 EtOAc/Hexanes to provide the desired product (E)-2-(2-(4-(bis(tert-butoxycarbonyl)amino)but-2-en-1-yl)-5-oxopyrrolidin-2-yl)-5-(2-methoxyquinolin-3-yl)-1H-imidazole-1-carboxylate. LCMS (ESI) calc'd for $C_{36}H_{47}N_5O_8$ [M+H]$^+$: 678.2, found: 678.5.

Step 5: (E)-5-(4-aminobut-2-en-1-yl)-5-(5-(2-methoxyquinolin-3-yl)-1H-imidazol-2-yl) pyrrolidin-2-one A 50 mL one-necked round bottom flask was charged with a solution of (E)-2-(2-(4-(bis(tert-butoxycarbonyl)amino)but-2-en-1-yl)-5-oxopyrrolidin-2-yl)-5-(2-methoxyquinolin-3-yl)-1H-imidazole-1-carboxylate (200 mg, 0.21 mmol) along with TFA (2 mL) and methylenechloride (10 mL). The reaction mixture was stirred at room temperature for 30 min. The mixture was concentrated to afford product tert-butyl (E)-5-(4-aminobut-2-en-1-yl)-5-(5-(2-methoxyquinolin3-yl)-1H-imidazol-2-yl)pyrrolidin-2-one. LCMS (ESI) calc'd for $C_{21}H_{23}N_5O_2$ [M+H]$^+$: 378.2, found: 378.2.

Step 6: 5-(4-aminobutyl)-5-(5-(2-methoxyquinolin-3-yl)-1H-imidazol-2-yl)pyrrolidin-2-one (E)-5-(4-aminobut-2-en-1-yl)-5-(5-(2-methoxyquinolin-3-yl)-1H-imidazol-2-yl)pyrrolidin-2-one was disolved in in MeOH (5 ml), along with TFA (160 mg, 0.163 mmol) and 10% Pd/C (10 mg, 50% in H$_2$O) in a 50 mL round bottom flask. The solution was stirred overnight under an atomosphere of hydrogen. The mixture was diluted with MeOH (20 ml), filtered through celite, washed with MeOH (20 ml) and concentrated. The residue was discolved with methylenechloride (100 ml) and H$_2$O (30 ml), and basified with conc NH$_4$OH (2 ml). The organic layer was separated, dried over Na$_2$SO$_4$, the filtered and concentrated to provide 5-(4-aminobutyl)-5-(5-(2-methoxyquinolin-3-yl)-1H-imidazol-2-yl)pyrrolidin-2-one. LCMS (ESI) calc'd for $C_{21}H_{25}N_5O_2$ [M+H]+: 380.2, found: 380.2.

Step 7: N-(4-(2-(5-(2-methoxyquinolin-3-yl)-1H-imidazol-2-yl)-5-oxopyrrolidin-2-yl)butyl)-2-(methylthio)benzamide In a 25 mL round bottom flask, N$_1$-((ethylimino)methylene)-N$_3$,N$_3$-dimethylpropane-1,3-diamine, HCl (25 mg, 0.130 mmol) and 1H-benzo[d][1,2,3]triazol-1-ol hydrate (20 mg, 0.131 mmol) was added to a solution of 2-(methylthio)benzoic acid (20 mg, 0.119 mmol) in DMF (1 ml). The mixture was then stirred for 5 minutes, followed by addition of a solution of 5-(4-aminobutyl)-5-(5-(2-methoxyquinolin-3-yl)-1H-imidazol-2-yl)pyrrolidin-2-one (30 mg, 0.079 mmol) in DCM (1 ml). The reaction mixture was then stirred for 1 hr at room temperature. The reaction was worked up by extraction with EtOAc (50 ml) and H$_2$O (20 ml). The organic layer was separated, dried over Na$_2$SO$_4$, filtered and concentrated. The product was purified by reverse phase HPLC yielding N-(4-(2-(5-(2-methoxyquinolin-3-yl)-1H-imidazol-2-yl)-5-oxopyrrolidin-2-yl)butyl)-2-(methylthio)benzamide. LCMS (ESI) calc'd for $C_{29}H_{31}N_5O_3S$ [M+H]$^+$: 530.2, found: 530.5.

$^1$H NMR (500 MHz, CD$_3$OD) δ 8.71 (s, 1H), 7.80 (d, J=3.0 Hz, 2H), 7.68 (s, 1H), 7.61 (t, J=1.5 Hz, 1H), 7.42 (t, J=2.0 Hz, 1H), 7.21-7.36 (m, 3H), 7.04 (s, 1H), 4.11 (s, 3H), 3.25-3.40 (m, 2H), 3.31 (s, 3H), 2.55 (m, 1H), 2.50 (m, 2H), 2.40 (m, 1H), 2.21 (m, 1H), 2.10 (m, 1H), 1.68 (m, 2H), 1.55 (m, 2H) ppm.

Using similar methodology as described in Examples 61, the following examples were prepared using the appropriate acidic starting materials:

| Example | Structure | Name | Exact Mass [M + H]$^+$ |
|---|---|---|---|
| 63 | 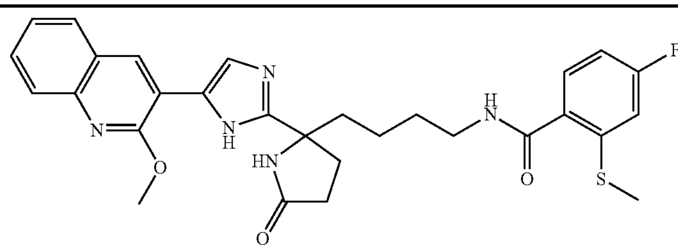 | (S)-N-(1-(5-(2-methoxyquinolin-3-yl)-1H-imidazol-2-yl)-5-(2-(methylthio)benzamido)pentyl)-1-methyl-1H-pyrazole-4-carboxamide | 548.3 |

Human HDAC Enzyme Inhibitor Fluor-De-Lys Assay
Materials

Recombinant human HDAC8 (BML-SE145-0100) and HDAC10 (BML-SE559-0050) enzymes, HDAC substrates BML-KI104 and BML-K1178, and HDAC developer solutions BML-KI105 and BML-KI176 were purchased from Enzo Life Sciences. Recombinant human HDAC5 and HDAC11 were purchased from BPS Bioscience (catalog numbers 50045 and 50021). Substrate Boc-Lys(TFA)-AMC was obtained from Bachem (catalog number I-1985). HDAC inhibitor suberoylanilide hydroxamic acid (SAHA) was obtained from Indofine and trichostatin A (TSA) was obtained from Sigma-Aldrich. D-myo inositol-1,4,5,6-tetraphosphate potassium salt (IP4) was obtained from Carbosynth (catalog MI 16761). HEPES pH 8.0 was obtained from Boston BioProducts, Tween-20 from Fisher Scientific (BP337), TCEP from Calbiochem and 7.5% bovine serum albumin (BSA) from Life Technologies (15260037). 384-well, black assay plates were obtained from Corning (3575).

Recombinant human HDAC1, HDAC2, and HDAC3/SMRT heterodimer were prepared by Merck Research Laboratories. Full length human HDAC1-FLAG was stably expressed in HEK-293F cells and purified using an anti-FLAG affinity chromatography with FLAG peptide (100 μg/ml) elution. The final concentration of HDAC1 was 1.98 uM by Western Blot analysis and 1.39 uM by active site titration. Full length human HDAC2-FLAG was expressed in baculovirus infected Sf9 cells and purified using an anti-FLAG affinity chromatography with FLAG peptide (100 μg/ml) elution. The eluted protein was then passed over an anti-HDAC1 immunoaffinity column to remove any complexes containing HDAC1. The final concentration of HDAC2 was 16.8 uM by Western Blot analysis and 7.6 uM by active site titration. Full length human HDAC3-FLAG was expressed in HEK-293F cells along with SMRT (amino acids 1-899)-6×His; plasmid APP-0024) and purified using an anti-FLAG affinity chromatography with FLAG peptide (100 μg/ml) elution. The eluted protein was then passed over an anti-HDAC1 immunoaffinity column to remove any complexes containing HDAC1. The final concentration of the HDAC3/SMRT complex was 2.03 uM by Western Blot analysis and 1.37 uM by active site titration.

HDAC Inhibition Assays

The histone deacetylase activities of HDAC1, HDAC2, HDAC3, HDAC6, and HDAC8 were measured in modified FLUOR DE LYS assays in 384-well format. In this assay, HDAC enzymes are initially incubated with an F-acetyl (or -trifluoroacetyl)-L-lysine-containing substrate with a C-terminal amide having aminomethylcoumarin as the amine component. HDACs cleave the F-acetyl group, rendering the resulting product susceptible to AMC cleavage by trypsin. The released AMC is then detected by its fluorescence.

The HDAC 1, 2 assays employed buffer A, which contained 20 mM HEPES, pH 8.0, 1 mM $MgCl_2$, 137 mM NaCl, 2.7 mM KCl, 0.05% BSA. The HDAC3/SMRT assay employed buffer B, consisting of 20 mM HEPES, pH 8.0, 1 mM $MgCl_2$, 50 mM NaCl, 2.7 mM KCl, 0.05% BSA, 0.005% Tween 20, and 10 μM IP4. The HDAC6 assay employed buffer C, consisting of 20 mM HEPES, pH 8.0, 1 mM $MgCl_2$, 137 mM NaCl, 2.7 mM KCl, 0.5 mM TCEP (Calbiochem) and 0.05% BSA. The HDAC8 assay employed buffer D, consisting of 20 mM HEPES, pH 8.0, 1 mM $MgCl_2$, 100 mM NaCl, 20 mM KCl, 0.1% n-octyl-β-D-glucoside (Anatrace) and 0.05% BSA. All steps were performed at room temperature (23° C.). The assay was performed by pre-incubating serial dilutions of test compounds with the target HDAC prior to initiation with substrate. Each compound was titrated in a 10-point dose response, using a 1:3 fold dilution scheme, with 0.15 ul of solution added by ECHO555 to the plate, followed by the addition of 20 μl of the appropriate HDAC isoform diluted in appropriate assay buffer. The incubation was allowed to proceed for 3 hours, then the appropriate substrate diluted in assay buffer (final substrate concentration ~$K_m$) was added and the reaction allowed to proceed for 60 min. Final conditions used for each assay were: 1. HDAC 1, 0.3 nM total enzyme, 20 μM substrate BML-KI104; 2. HDAC 2, 1.5 nM total enzyme, 40 μM substrate BML-KI104; 3. HDAC 3/SMRT, 0.3 nM total enzyme, 20 μM substrate BML-KI104; 4. HDAC 6, 1.3 nM total enzyme, 2.5 μM substrate BML-KI104; 5. HDAC 8, 1.3 nM total enzyme, 200 μM substrate BML-KI178; the final high dose of test compound was 30 μM. For potent compounds, 900 nM was used as the final high dose. The reactions were stopped and developed by addition of 30 ul of HDAC developer solution containing a saturating level of HDAC inhibitor as follows: 1. HDACs 1, 2, 3 and 6, developer BML-KI105 (stock diluted 1:125, containing 20 uM SAHA, 2. HDAC 8, developer BML-KI176 (1:100 plus 40 uM SAHA, and the plates were shaken to assure good mixing, briefly centrifuged, incubated for 30 minutes at room temperature and then the fluorescence intensity (excitation 380 nm, emission 460 nm) measured using a PHERAstar plate reader. For each assay plate, both minimal inhibition (100% DMSO; 0% inhibition) and maximal inhibition (either 10 uM SAHA or 100 uM TSA; 100% inhibition) controls were added. For data analysis, background subtracted product (fluorescence) vs. time data for each inhibitor concentration was fitted using a 4-parameter fit.

All compounds prepared were tested in the binding assays with HDAC1, 2, 3, 6 and 8.

| Ex. # | HDAC1 | HDAC2 | HDAC3 | HDAC6 | HDAC8 |
|---|---|---|---|---|---|
|   | 19820 | 31150 | 29 | 45000 | 10400 |
| 2 | 15000 | 45000 | 41 | 45000 | 45000 |
| 3 | 6645 | 7663 | 146 | 45000 | 45000 |
| 4 | 12830 | 16514 | 1200 |  |  |
| 5 | 24160 | 42330 | 60 | 45000 | 45000 |
| 6 | 45000 | 45000 | 110 |  |  |
| 7 | 24630 | 28530 | 170 |  |  |
| 8 | 45000 | 45000 | 470 |  |  |
| 9 | 7883 | 15680 | 100 | 45000 | 45000 |
| 10 | 8014 | 6100 | 110 |  |  |
| 11 | 29520 | 39780 | 420 | 45000 | 45000 |
| 12 | 45000 | 45000 | 670 |  |  |
| 13 | 45000 | 45000 | 700 |  |  |
| 14 | 45000 | 45000 | 760 |  |  |
| 15 | 45000 | 45000 | 1100 | 45000 | 45000 |
| 16 | 45000 | 45000 | 1200 |  |  |
| 17 | 45000 | 45000 | 1800 |  |  |
| 18 | 19150 | 38940 | 810 |  |  |
| 19 | 45000 | 45000 | 2600 |  |  |
| 20 | 45000 | 45000 | 3100 |  |  |
| 21 | 511.3 | 699.4 | 36 | 15000 | 45000 |
| 22 | 25790 | 45000 | 1900 |  |  |
| 23 | 45000 | 45000 | 3300 |  |  |
| 24 | 45000 | 45000 | 3300 |  |  |
| 25 | 45000 | 45000 | 3600 |  |  |
| 26 | 43730 | 45000 | 3600 |  |  |
| 27 | 560.8 | 761.7 | 47 | 45000 | 45000 |
| 28 | 2579 | 2983 | 220 |  |  |
| 29 | 45000 | 45000 | 3900 |  |  |
| 30 | 6425 | 16530 | 560 |  |  |
| 31 | 30640 | 45000 | 2700 |  |  |
| 32 | 411.9 | 500.4 | 41 | 15000 | 45000 |
| 33 | 45000 | 45000 | 4800 |  |  |
| 34 | 45000 | 45000 | 5100 |  |  |
| 35 | 38810 | 45000 | 4600 |  |  |
| 36 | 41880 | 45000 | 5000 |  |  |
| 37 | 45000 | 45000 | 5400 |  |  |
| 38 | 25920 | 44510 | 3500 |  |  |
| 39 | 45000 | 45000 | 6000 |  |  |
| 40 | 2191 | 4981 | 310 |  |  |
| 41 | 4362 | 7752 | 630 |  |  |
| 42 | 45000 | 45000 | 6500 |  |  |
| 43 | 45000 | 45000 | 7000 |  |  |
| 44 | 40810 | 45000 | 6400 |  |  |
| 45 | 45000 | 45000 | 7300 |  |  |
| 46 | 23940 | 45000 | 3900 |  |  |
| 47 | 26190 | 42890 | 4400 |  |  |
| 48 | 31150 | 38320 | 5600 |  |  |
| 49 | 25250 | 45000 | 5000 |  |  |
| 50 | 9.748 | 29.26 | 7.6 | 9019 | 45000 |
| 51 | 45000 | 45000 | 109.8 |  |  |
| 52 | 44270 | 45000 | 111.4 |  |  |
| 53 | 45000 | 45000 | 127.1 |  |  |
| 54 | 41770 | 45000 | 162.8 |  |  |
| 55 | 35110 | 45000 | 140.1 |  |  |
| 56 | 45000 | 45000 | 261.3 |  |  |
| 57 | 15380 | 45000 | 127.9 |  |  |
| 58 | 45000 | 45000 | 379.4 |  |  |
| 59 | 2412 | 22980 | 229.9 |  |  |

-continued

| Ex. # | HDAC1 | HDAC2 | HDAC3 | HDAC6 | HDAC8 |
|-------|-------|-------|-------|-------|-------|
| 60 | 540 | 1121 | 23 | 11560 | 45000 |
| 61 | 754.5 | 1076 | 86.26 | 45000 | 45000 |
| 62 | 45000 | 45000 | 670.6 | | |
| 63 | 45000 | 45000 | 958.2 | | |

Methods of Use

Compounds described herein having therapeutic applications, such as the compounds of general formula (I), the compounds of the Examples 1 through 63, and pharmaceutically acceptable salts of the foregoing, may be administered to a patient for the purpose of inhibiting HDAC3. The term "administration" and variants thereof (e.g., "administering" a compound) means providing the compound to the individual in need of treatment. When a compound is provided in combination with one or more additional active agents (e.g., anti-tumor agents for treating cancers), "administration" and its variants are each understood to include concurrent and sequential provision of the compound or salt and other agents.

The compounds disclosed herein may be HDAC3 inhibitors. These compounds are potentially useful in treating diseases or disorders including, but not limited to, cancer, inflammation, neurodegeneration diseases and/or diabetes in a subject.

In specific embodiments, the disease or disorder to be treated is cancer. In particular embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary (i.e., cancers in which a metastasized cancer is found but the original cancer site is not known). In particular embodiments, the cancer is present in an adult patient; in additional embodiments, the cancer is present in a pediatric patient. In particular embodiments, the cancer is AIDS-related.

In specific embodiments, the cancer is selected from brain and spinal cancers. In particular embodiments, the cancer is selected from the group consisting of anaplastic astrocytomas, glioblastomas, astrocytomas, and estheosioneuroblastomas (also known as olfactory blastomas). In particular embodiments, the brain cancer is selected from the group consisting of astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma), oligodendroglial tumor (e.g., oligodendroglioma, and anaplastic oligodendroglioma), oligoastrocytic tumor (e.g., oligoastrocytoma, and anaplastic oligoastrocytoma), ependymoma (e.g., myxopapillary ependymoma, and anaplastic ependymoma); medulloblastoma, primitive neuroectodermal tumor, schwannoma, meningioma, atypical meningioma, anaplastic meningioma, pituitary adenoma, brain stem glioma, cerebellar astrocytoma, cerebral astorcytoma/malignant glioma, visual pathway and hypothalmic glioma, and primary central nervous system lymphoma. In specific instances of these embodiments, the brain cancer is selected from the group consisting of glioma, glioblastoma multiforme, paraganglioma, and suprantentorial primordial neuroectodermal tumors (sPNET).

In specific embodiments, the cancer is selected from cancers of the head and neck, including nasopharyngeal cancers, nasal cavity and paranasal sinus cancers, hypopharyngeal cancers, oral cavity cancers (e.g., squamous cell carcinomas, lymphomas, and sarcomas), lip cancers, oropharyngeal cancers, salivary gland tumors, cancers of the larynx (e.g., laryngeal squamous cell carcinomas, rhabdomyosarcomas), and cancers of the eye or ocular cancers. In particular embodiments, the ocular cancer is selected from the group consisting of intraocular melanoma and retinoblastoma.

In specific embodiments, the cancer is selected from leukemia and cancers of the blood. In particular embodiments, the cancer is selected from the group consisting of myeloproliferative neoplasms, myelodysplastic syndromes, myelodysplastic/myeloproliferative neoplasms, acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blast-phase chronic myelogenous leukemia, angioimmunoblastic lymphoma, acute lymphoblastic leukemia, Langerans cell histiocytosis, hairy cell leukemia, and plasma cell neoplasms including plasmacytomas and multiple myelomas. Leukemias referenced herein may be acute or chronic.

In specific embodiments, the cancer is selected from skin cancers. In particular embodiments, the skin cancer is selected from the group consisting of melanoma, squamous cell cancers, and basal cell cancers.

In specific embodiments, the cancer is selected from cancers of the reproductive system. In particular embodiments, the cancer is selected from the group consisting of breast cancers, cervical cancers, vaginal cancers, ovarian cancers, prostate cancers, penile cancers, and testicular cancers. In specific instances of these embodiments, the cancer is a breast cancer selected from the group consisting of ductal carcinomas and phyllodes tumors. In specific instances of these embodiments, the breast cancer may be male breast cancer or female breast cancer. In specific instances of these embodiments, the cancer is a cervical cancer selected from the group consisting of squamous cell carcinomas and adenocarcinomas. In specific instances of these embodiments, the cancer is an ovarian cancer selected from the group consisting of epithelial cancers.

In specific embodiments, the cancer is selected from cancers of the gastrointestinal system. In particular embodiments, the cancer is selected from the group consisting of esophageal cancers, gastric cancers (also known as stomach cancers), gastrointestinal carcinoid tumors, pancreatic cancers, gallbladder cancers, colorectal cancers, and anal cancer. In instances of these embodiments, the cancer is selected from the group consisting of esophageal squamous cell carcinomas, esophageal adenocarcinomas, gastric adenocarcinomas, gastrointestinal carcinoid tumors, gastrointestinal stromal tumors, gastric lymphomas, gastrointestinal lymphomas, solid pseudopapillary tumors of the pancreas, pancreatoblastoma, islet cell tumors, pancreatic carcinomas including acinar cell carcinomas and ductal adenocarcinomas, gallbladder adenocarcinomas, colorectal adenocarcinomas, and anal squamous cell carcinomas.

In specific embodiments, the cancer is selected from liver and bile duct cancers. In particular embodiments, the cancer is liver cancer (also known as hepatocellular carcinoma). In particular embodiments, the cancer is bile duct cancer (also known as cholangiocarcinoma); in instances of these embodiments, the bile duct cancer is selected from the group consisting of intrahepatic cholangiocarcinoma and extrahepatic cholangiocarcinoma.

In specific embodiments, the cancer is selected from kidney and bladder cancers. In particular embodiments, the cancer is a kidney cancer selected from the group consisting of renal cell cancer, Wilms tumors, and transitional cell cancers. In particular embodiments, the cancer is a bladder cancer selected from the group consisting of urethelial carcinoma (a transitional cell carcinoma), squamous cell carcinomas, and adenocarcinomas.

In specific embodiments, the cancer is selected from bone cancers. In particular embodiments, the bone cancer is selected from the group consisting of osteosarcoma, malignant fibrous histiocytoma of bone, Ewing sarcoma, chordoma (cancer of the bone along the spine).

In specific embodiments, the cancer is selected from lung cancers. In particular embodiments, the lung cancer is selected from the group consisting of non-small cell lung cancer, small cell lung cancers, bronchial tumors, and pleuropulmonary blastomas.

In specific embodiments, the cancer is selected from malignant mesothelioma. In particular embodiments, the cancer is selected from the group consisting of epithelial mesothelioma and sarcomatoids.

In specific embodiments, the cancer is selected from sarcomas. In particular embodiments, the sarcoma is selected from the group consisting of central chondrosarcoma, central and periosteal chondroma, fibrosarcoma, clear cell sarcoma of tendon sheaths, and Kaposi's sarcoma.

In specific embodiments, the cancer is selected from lymphomas. In particular embodiments, the cancer is selected from the group consisting of Hodgkin lymphoma (e.g., Reed-Stemberg cells), non-Hodgkin lymphoma (e.g., diffuse large B-cell lymphoma, follicular lymphoma, mycosis fungoides, Sezary syndrome, primary central nervous system lymphoma), cutaneous T-cell lymphomas, primary central nervous system lymphomas.

In specific embodiments, the cancer is selected from glandular cancers. In particular embodiments, the cancer is selected from the group consisting of adrenocortical cancer (also known as adrenocortical carcinoma or adrenal cortical carcinoma), pheochromocytomas, paragangliomas, pituitary tumors, thymoma, and thymic carcinomas.

In specific embodiments, the cancer is selected from thyroid cancers. In particular embodiments, the thyroid cancer is selected from the group consisting of medullary thyroid carcinomas, papillary thyroid carcinomas, and follicular thyroid carcinomas.

In specific embodiments, the cancer is selected from germ cell tumors. In particular embodiments, the cancer is selected from the group consisting of malignant extracranial germ cell tumors and malignant extragonadal germ cell tumors. In specific instances of these embodiments, the malignant extragonadal germ cell tumors are selected from the group consisting of nonseminomas and seminomas.

In specific embodiments, the cancer is selected from heart tumors. In particular embodiments, the heart tumor is selected from the group consisting of malignant teratoma, lymphoma, rhabdomyosacroma, angiosarcoma, chondrosarcoma, infantile fibrosarcoma, and synovial sarcoma.

In specific embodiments, the disease or disorder to be treated is inflammation and diseases that are associated with inflammation; such conditions may include, without limitation: inflammatory or allergic diseases such as asthma, allergic rhinitis, hypersensitivity lung diseases, hypersensitivity pneumonitis, eosinophilic pneumonias, delayed-type hypersensitivity, atherosclerosis, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, multiple sclerosis, Guillain-Barre syndrome, systemic lupus erythematosus, myastenia gravis, glomerulonephritis, autoimmune thyroiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, eosiniphilic fasciitis; and cancers.

In specific embodiments, the disease or disorder to be treated is a neurodegeneration disease. Such diseases and disorders may include, but are not limited to, glaucoma, schizophrenia, tauopathies, Huntington's disease, Parkinson's disease, Amyotrophic lateral sclerosis, mild cognitive impairment (MCI), neuropathy, neurodegeneration disorders, such as Alzheimer's disease (AD), cardiovascular diseases, diseases associated with inflammation, diseases associated with immunosuppression.

In specific embodiments, the invention provides methods of providing neuroprotective effects; preventing damage to cardiac tissue; and treating diseases associated with inflammation or immunosuppression.

In specific embodiments, the invention provides methods of inhibiting phosphorylation of tau polypeptides, or inhibiting formation of NFTs, in animal subjects, such as, veterinary and human subjects. Accordingly, a compound of the invention may be used to study and treat AD and other tauopathies.

Tauopathies that may be treated with a compound of the invention may include, without limitation: Alzheimer's disease, Amyotrophic lateral sclerosis with cognitive impairment (ALSci), Argyrophilic grain dementia, Bluit disease, Corticobasal degeneration (CBD), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Multiple system atrophy, Myotonic dystrophy, Niemann-Pick disease (type C), Pallido-ponto-nigral degeneration, Parkinsonism-dementia complex of Guam, Pick's disease (PiD), Post-encephalitic parkinsonism (PEP), Prion diseases (including Creutzfeldt-Jakob Disease (CJD), Variant Creutzfeldt-Jakob Disease (vCJD), Fatal Familial Insomnia, and Kuru), Progressive supercortical gliosis, Progressive supranuclear palsy (PSP), Richardson's syndrome, Subacute sclerosing panencephalitis, Tangle-only dementia, and Glaucoma.

One or more of the compounds of this invention may also be useful in the treatment of conditions associated with tissue damage or stress, stimulating cells, or promoting differentiation of cells. Accordingly, in some embodiments, a compound of this invention may be used to provide therapeutic benefit in a variety of conditions or medical procedures involving stress in cardiac tissue; such conditions may include, without limitation: ischemia; hemorrhage; hypovolemic shock; myocardial infarction; an interventional cardiology procedure; cardiac bypass surgery; fibrinolytic therapy; angioplasty; and stent placement.

The effectiveness of a compound in treating pathology associated with cellular stress (including ischemia, hemorrhage, hypovolemic shock, myocardial infarction, and other cardiovascular disorders) may be confirmed by testing the ability of a compound to prevent cellular damage in established cellular stress assays, and to prevent tissue damage and promote functional recovery in animal models of ischemia-reperfusion, and trauma-hemorrhage.

In addition, compounds of the instant invention be used for the treatment of diseases associated with immunosuppression, such as, for example, in individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; or immunosuppression due to congenital deficiency in receptor function or other causes.

One or more of the compounds of the invention may be useful for treatment of neurodegeneration diseases; such conditions may include, without limitation, Parkinson's disease and Huntington's disease.

In specific embodiments, the disease or disorder to be treated is diabetes or related diseases, such as cardiometabolic diseases associated with elevated LDL, such as atherosclerosis, fatty liver and nonalcoholic steatohepatitis (NASH), and noninsulin-dependent diabetes (NIDDM), hyperglycemia, and other symptoms associated with NIDDM. The compounds of the invention can be useful as a preventive or a remedy for noninsulin-dependent diabetes (NIDDM), hyperglycemia, and other symptoms associated with NIDDM.

In specific embodiments, the invention relates to a method of treating hyperglycemia, diabetes or insulin resistance in a mammalian patient in need of such treatment which comprises administering to said patient a compound described herein or a pharmaceutically acceptable salt thereof or a pharmaceutical composition comprising the compound or pharmaceutically acceptable salt, in an amount that is effective to treat hyperglycemia, diabetes or insulin resistance.

In specific embodiments, the invention relate a to a method of treating type 2 diabetes in a mammalian patient in need of such treatment comprising administering to the patient a compound described herein or a pharmaceutically acceptable salt thereof or a pharmaceutical composition comprising the compound or pharmaceutically acceptable salt, in an amount that is effective to treat type 2 diabetes.

In specific embodiments, the invention relates to a method of treating non-insulin dependent diabetes mellitus in a mammalian patient in need of such treatment comprising administering to the patient a compound described herein or a pharmaceutically acceptable salt thereof or a pharmaceutical composition comprising the compound or pharmaceutically acceptable salt, in an amount that is effective to treat non-insulin dependent diabetes mellitus.

The present invention is also directed to the use of a compound described herein or a pharmaceutically acceptable salt thereof in the manufacture of a medicament for use in treating cardiometabolic diseases associated with elevated LDL, such as atherosclerosis, fatty liver and nonalcoholic steatohepatitis (NASH), and noninsulin-dependent diabetes (NIDDM), hyperglycemia, and other symptoms associated with NIDDM, metabolic diseases such as obesity, diabetes, hormone secretion disorder, hyperlipemia, gout, fatty liver, and the like; circulatory diseases such as angina pectoris, acute/congestive cardiac insufficiency, myocardial infarction, coronary arteriosclerosis, hypertension, nephropathy, electrolyte abnormality, and the like. The compounds described herein may be especially useful as a preventive or a remedy for noninsulin-dependent diabetes (NIDDM), hyperglycemia, and other symptoms associated with NIDDM.

The amount of a compound administered to a patient is an amount sufficient to inhibit HDAC3 in the patient. In an embodiment, the amount of a compound can be an "effective amount" or "therapeutically effective amount," such that the subject compound is administered in an amount that will elicit, respectively, a biological or medical (i.e., intended to treat) response of a tissue, system, animal, or human that is being sought by a researcher, veterinarian, medical doctor, or other clinician. An effective amount does not necessarily include considerations of toxicity and safety related to the administration of a compound.

An effective amount of a compound will vary with the particular compound chosen (e.g., considering the potency, efficacy, and/or half-life of the compound); the route of administration chosen; the condition being treated; the severity of the condition being treated; the age, size, weight, and physical condition of the patient being treated; the medical history of the patient being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen where a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life, which can be determined by a skilled artisan. In addition, suitable dosing regimens, including the duration such regimens are administered, for a compound disclosed herein depend on the disease or condition being treated, the severity of the disease or condition, the age and physical condition of the patient being treated, the medical history of the patient being treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as the individual patient needs change. Typical daily dosages may vary depending upon the particular route of administration chosen.

Combination Therapy

The compounds of the present invention are further useful in methods for the prevention or treatment of the aforementioned diseases, disorders and conditions in combination with other therapeutic agents.

The compounds of the present invention may be used in combination with one or more other drugs in the treatment, prevention, suppression or amelioration of diseases or conditions for which compounds described herein or the other drugs may have utility, where the combination of the drugs together are safer or more effective than either drug alone. Such other drug(s) may be administered in an amount commonly used therefore, contemporaneously or sequentially with a compound described herein or a pharmaceutically acceptable salt thereof. When a compound described herein is used contemporaneously with one or more other drugs, the pharmaceutical composition may in specific embodiments contain such other drugs and the compound described herein or its pharmaceutically acceptable salt in unit dosage form. However, the combination therapy may also include therapies in which the compound described herein or its pharmaceutically acceptable salt and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound described herein or a pharmaceutically acceptable salt thereof.

For the treatment of cancer, the additional active agent(s) may be one or more agents selected from the group consisting of STING agonist compounds, anti-viral compounds, antigens, adjuvants, anti-cancer agents, CTLA-4, LAG-3 and PD-1 pathway antagonists, lipids, liposomes, peptides, cytotoxic agents, chemotherapeutic agents, immunomodulatory cell lines, checkpoint inhibitors, vascular endothelial growth factor (VEGF) receptor inhibitors, topoisomerase II inhibitors, smoothen inhibitors, alkylating agents, anti-tumor antibiotics, anti-metabolites, retinoids, and immunomodulatory agents including but not limited to anti-cancer vaccines. It will be understood that such additional active agent(s) may be provided as a pharmaceutically acceptable salt. It will be understood the descriptions of the above additional active agents may be overlapping. It will also be understood that the treatment combinations are subject to optimization, and it is understood that the best combination to use of the compounds of general formula (I), or pharmaceutically acceptable salts of the foregoing, and one or more additional active agents will be determined based on the individual patient needs.

A compound disclosed herein may be used in combination with one or more other active agents, including but not limited to, other anti-cancer agents that are used in the prevention, treatment, control, amelioration, or reduction of risk of a particular disease or condition. In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present disclosure.

When a compound disclosed herein is used contemporaneously with one or more other active agents, a composition containing such other active agents in addition to the compound disclosed herein is contemplated. Accordingly, the compositions of the present disclosure include those that also contain one or more other active ingredients, in addition to a compound disclosed herein. A compound disclosed herein may be administered either simultaneously with, or before or after, one or more other active agent(s). A compound disclosed herein may be administered separately, by the same or different route of administration, or together in the same pharmaceutical composition as the other agent(s).

STING agonist compounds that may be used in combination with the compounds of formula (I), or pharmaceutically acceptable salts of the foregoing, disclosed herein include but are not limited to cyclic di-nucleotide compounds, such as those disclosed, for example, in International Patent Application Publication Nos. WO2014093936, WO2014189805, WO2014189806, WO2015185565, WO2016120305, WO2016096174, WO2016096577, WO2017027645, WO2017027646, WO2017075477, WO2017093933, and WO2018009466.

Anti-viral compounds that may be used in combination with the compounds of the invention or pharmaceutically acceptable salts of the foregoing, disclosed herein include hepatitis B virus (HBV) inhibitors, hepatitis C virus (HCV) protease inhibitors, HCV polymerase inhibitors, HCV NS4A inhibitors, HCV NS5A inhibitors, HCV NS5b inhibitors, and human immunodeficiency virus (HIV) inhibitors. Such anti-viral compounds may be provided as a pharmaceutically acceptable salt, where appropriate.

Antigens and adjuvants that may be used in combination with the compounds of the invention, or the pharmaceutically acceptable salts of the foregoing, include B7 costimulatory molecule, interleukin-2, interferon-y, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryllipid A, lipoteichoic acid, imiquimod, resiquimod, and in addition retinoic acid-inducible gene I (RIG-I) agonists such as poly I:C, used separately or in combination with the described compositions are also potential adjuvants. Such antigens and anjuvants may be provided as a pharmaceutically acceptable salt, where appropriate.

CLTA-4 and PD-1 pathways are important negative regulators of immune response. Activated T-cells up-regulate CTLA-4, which binds on antigen-presenting cells and inhibits T-cell stimulation, IL-2 gene expression, and T-cell proliferation; these anti-tumor effects have been observed in mouse models of colon carcinoma, metastatic prostate cancer, and metastatic melanoma. PD-1 binds to active T-cells and suppresses T-cell activation; PD-1 antagonists have demonstrated anti-tumor effects as well. CTLA-4 and PD-1 pathway antagonists that may be used in combination with the compounds of general formula (I), compounds of general formula (II), compounds of general formula (III), compounds of general formula (IV), compounds of general formula (V), compounds of general formula (VI), or the pharmaceutically acceptable salts of the foregoing, disclosed herein, include ipilimumab, tremelimumab, nivolumab, pembrolizumab, CT-011, AMP-224, and MDX-1106.

"PD-1 antagonist" or "PD-1 pathway antagonist" means any chemical compound or biological molecule that blocks binding of PD-L1 expressed on a cancer cell to PD-1 expressed on an immune cell (T-cell, B-cell, or NKT-cell) and preferably also blocks binding of PD-L2 expressed on a cancer cell to the immune-cell expressed PD-1. Alternative names or synonyms for PD-1 and its ligands include: PDCD1, PD1, CD279, and SLEB2 for PD-1; PDCD1L1, PDL1, B7H1, B7-4, CD274, and B7-H for PD-L1; and PDCD1L2, PDL2, B7-DC, Btdc, and CD273 for PD-L2. In any of the treatment method, medicaments and uses of the present disclosure in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present disclosure include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody, or a chimeric antibody and may include a human constant region. In some embodiments, the human constant region is selected from the group consisting of IgG1, IgG2, IgG3, and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv, and Fv fragments.

Examples of mAbs that bind to human PD-1, and useful in the treatment method, medicaments and uses of the present disclosure, are described in U.S. Pat. Nos. 7,488,802, 7,521,051, 8,008,449, 8,354,509, and 8,168,757, PCT International Patent Application Publication Nos. WO2004/004771, WO2004/072286, and WO2004/056875, and U.S. Patent Application Publication No. US2011/0271358.

Examples of mAbs that bind to human PD-L1, and useful in the treatment method, medicaments and uses of the present disclosure, are described in PCT International Patent Application Nos. WO2013/019906 and WO2010/077634 A1 and in U.S. Pat. No. 8,383,796. Specific anti-human PD-L1 mAbs useful as the PD-1 antagonist in the treatment method, medicaments and uses of the present disclosure include MPDL3280A, BMS-936559, MEDI4736, MSB0010718C, and an antibody that comprises the heavy chain and light chain variable regions of SEQ ID NO:24 and SEQ ID NO:21, respectively, of WO2013/019906.

Other PD-1 antagonists useful in any of the treatment method, medicaments, and uses of the present disclosure include an immune-adhesion that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immune-adhesion molecules that specifically bind to PD-1 are described in PCT International Patent Application Publication Nos. WO2010/027827 and WO2011/066342. Specific fusion proteins useful as the PD-1 antagonist in the treatment method, medicaments, and uses of the present disclosure include AMP-224 (also known as B7-DCIg), which is a PD-L2-FC fusion protein and binds to human PD-1.

The disclosure further relates to a method of treating cancer in a human patient comprising administration of a compound of the invention and a PD-1 antagonist to the patient. The compound of the disclosure and the PD-1 antagonist may be administered concurrently or sequentially.

In particular embodiments, the PD-1 antagonist is an anti-PD-1 antibody, or antigen binding fragment thereof. In alternative embodiments, the PD-1 antagonist is an anti-PD-L1 antibody, or antigen binding fragment thereof. In some embodiments, the PD-1 antagonist is pembrolizumab (KEYTRUDA™, Merck & Co., Inc., Kenilworth, N.J., USA), nivolumab (OPDIVO™, Bristol-Myers Squibb Company, Princeton, N.J., USA), cemiplimab (LIBTAYO™, Regeneron Pharmaceuticals, Inc., Tarrytown, N.Y., USA), atezolizumab (TECENTRIQ™, Genentech, San Francisco, Calif., USA), durvalumab (IMFINZI™, AstraZeneca Pharmaceuticals LP, Wilmington, Del.), or avelumab (BAVENCIO™, Merck KGaA, Darmstadt, Germany).

In some embodiments, the PD-1 antagonist is pembrolizumab. In particular sub-embodiments, the method comprises administering 200 mg of pembrolizumab to the patient about every three weeks. In other sub-embodiments, the method comprises administering 400 mg of pembrolizumab to the patient about every six weeks.

In further sub-embodiments, the method comprises administering 2 mg/kg of pembrolizumab to the patient about every three weeks. In particular sub-embodiments, the patient is a pediatric patient.

In some embodiments, the PD-1 antagonist is nivolumab. In particular sub-embodiments, the method comprises administering 240 mg of nivolumab to the patient about every two weeks. In other sub-embodiments, the method comprises administering 480 mg of nivolumab to the patient about every four weeks.

In some embodiments, the PD-1 antagonist is cemiplimab. In particular embodiments, the method comprises administering 350 mg of cemiplimab to the patient about every 3 weeks.

In some embodiments, the PD-1 antagonist is atezolizumab. In particular sub-embodiments, the method comprises administering 1200 mg of atezolizumab to the patient about every three weeks.

In some embodiments, the PD-1 antagonist is durvalumab. In particular sub-embodiments, the method comprises administering 10 mg/kg of durvalumab to the patient about every two weeks.

In some embodiments, the PD-1 antagonist is avelumab. In particular sub-embodiments, the method comprises administering 800 mg of avelumab to the patient about every two weeks.

Examples of cytotoxic agents that may be used in combination with the compounds of general formula (I), or pharmaceutically acceptable salts of the foregoing, include, but are not limited to, arsenic trioxide (sold under the tradename TRISENOX®), asparaginase (also known as L-asparaginase, and Erwinia L-asparaginase, sold under the tradenames ELSPAR® and KIDROLASE®).

Chemotherapeutic agents that may be used in combination with the compounds of the invention, or pharmaceutically acceptable salts of the foregoing, disclosed herein include abiraterone acetate, altretamine, anhydrovinblastine, auristatin, bexarotene, bicalutamide, BMS 184476, 2,3,4,5,6-pentafluoro-N-(3-fluoro-4-methoxyphenyl) benzene sulfonamide, bleomycin, N,N-dimethyl-L-valyl-L-valyl-N-methyl-L-valyl-L-prolyl-1-Lproline-t-butylamide, cachectin, cemadotin, chlorambucil, cyclophosphamide, 3',4'-didehydro-4'deoxy-8'-norvin-caleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyurea andtaxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, nivolumab, onapristone, paclitaxel, pembrolizumab, prednimustine, procarbazine, RPR109881, stramustine phosphate, tamoxifen, tasonermin, taxol, tretinoin, vinblastine, vincristine, vindesine sulfate, and vinflunine. Such chemotherapeutic agents may be provided as a pharmaceutically acceptable salt, where appropriate.

Examples of vascular endothelial growth factor (VEGF) receptor inhibitors include, but are not limited to, bevacizumab (sold under the trademark AVASTIN), axitinib (described in PCT International Patent Publication No. WO01/002369), Brivanib Alaninate ((S)-((R)-1-(4-(4-Fluoro-2-methyl-1H-indol-5-yloxy)-5-methylpyrrolo[2,1-f][1,2,4]triazin-6-yloxy) propan-2-yl)2-aminopropanoate, also known as BMS-582664), motesanib (N-(2,3-dihydro-3,3-dimethyl-1H-indol-6-yl)-2-[(4-pyridinylmethyl)amino]-3-pyridinecarboxamide. and described in PCT International Patent Application Publication No. WO02/068470), pasireotide (also known as SO 230, and described in PCT International Patent Publication No. WO02/010192), and sorafenib (sold under the tradename NEXAVAR). Such inhibitors may be provided as a pharmaceutically acceptable salt, where appropriate.

Examples of topoisomerase II inhibitors, include but are not limited to, etoposide (also known as VP-16 and Etoposide phosphate, sold under the tradenames TOPOSAR, VEPESID, and ETOPOPHOS), and teniposide (also known as VM-26, sold under the tradename VUMON). Such inhibitors may be provided as a pharmaceutically acceptable salt, where appropriate.

Examples of alkylating agents, include but are not limited to, 5-azacytidine (sold under the trade name VIDAZA), decitabine (sold under the trade name of DECOGEN), temozolomide (sold under the trade names TEMCAD, TEMODAR, and TEMODAL), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX® and MYLERAN®), carboplatin (sold under the tradename PARAPLATIN®), lomustine (also known as CCNU, sold under the tradename CEENU®), cisplatin (also known as CDDP, sold under the tradenames PLATINOL® and PLATINOL®-AQ), chlorambucil (sold under the tradename LEUKERAN®), cyclophosphamide (sold under the tradenames CYTOXAN® and NEOSAR®), dacarbazine (also known as DTIC, DIC and imidazole carboxamide, sold under the tradename DTIC-DOME®), altretamine (also known as hexamethylmelamine (HMM) sold under the tradename HEXALEN®), ifosfamide (sold under the tradename IFEX®), procarbazine (sold under the tradename MATULANE®), mechlorethamine (also known as nitrogen mustard, mustine and mechloroethamine hydrochloride, sold under the tradename MUSTARGEN®), streptozocin (sold under the tradename ZANOSAR®), thiotepa (also known as thiophosphoamide, TESPA and TSPA, and sold under the tradename THIOPLEX®). Such alkylating agents may be provided as a pharmaceutically acceptable salt, where appropriate.

Examples of anti-tumor antibiotics include, but are not limited to, doxorubicin (sold under the tradenames ADRIAMYCIN® and RUBEX®), bleomycin (sold under the tradename LENOXANE®), daunorubicin (also known as dauorubicin hydrochloride, daunomycin, and rubidomycin hydrochloride, sold under the tradename CERUBIDINE®), daunorubicin liposomal (daunorubicin citrate liposome, sold under the tradename DAUNOXOME®), mitoxantrone (also known as DHAD, sold under the tradename NOVANTRONE®), epirubicin (sold under the tradename ELLENCE™), idarubicin (sold under the tradenames IDAMYCIN®, IDAMYCIN PFS®), and mitomycin C (sold under the tradename MUTAMYCIN®). Such anti-tumor antibiotics may be provided as a pharmaceutically acceptable salt, where appropriate.

Examples of anti-metabolites include, but are not limited to, claribine (2-chlorodeoxyadenosine, sold under the tradename LEUSTATIN®), 5-fluorouracil (sold under the tradename ADRUCIL®), 6-thioguanine (sold under the tradename PURINETHOL®), pemetrexed (sold under the tradename ALIMTA®), cytarabine (also known as arabinosylcytosine (Ara-C), sold under the tradename CYTOSAR-U®), cytarabine liposomal (also known as Liposomal Ara-C, sold under the tradename DEPOCYT™), decitabine (sold under the tradename DACOGEN®), hydroxyurea and (sold under the tradenames HYDREA®, DROXIA™ and MYLOCEL™) fludarabine (sold under the tradename FLUDARA®), floxuridine (sold under the tradename FUDR®), cladribine (also known as 2-chlorodeoxyadenosine (2-CdA) sold under the tradename LEUSTATIN™), methotrexate (also known as amethopterin, methotrexate sodium (MTX), sold under the tradenames RHEUMATREX® and TREXALL™), and pentostatin (sold under the tradename NIPENT®). Such anti-metabolites may be provided as a pharmaceutically acceptable salt, where appropriate.

Examples of retinoids include, but are not limited to, alitretinoin (sold under the tradename PANRETIN®), tretinoin (all-trans retinoic acid, also known as ATRA, sold under the tradename VESANOID®), Isotretinoin (13-cis-retinoic acid, sold under the tradenames ACCUTANE®, AMNESTEEM®, CLARAVIS®, CLARUS®, DECUTAN®, ISOTANE®, IZOTECH®, ORATANE®, ISOTRET®, and SOTRET®), and bexarotene (sold under the tradename TARGRETIN®). Such compounds may be provided as a pharmaceutically acceptable salt, where appropriate.

Examples of other active ingredients useful for the treatment of diabetes and/or inflammation, that may be administered in combination with a compound of the invention or a pharmaceutically acceptable salt thereof and either administered separately or in the same pharmaceutical composition, include, but are not limited to:

(1) dipeptidyl peptidase-IV (DPP-4) inhibitors, such as, sitagliptin (disclosed in U.S. Pat. No. 6,699,871), vildagliptin, saxagliptin, alogliptin, denagliptin, carmegliptin, dutogliptin, melogliptin, linagliptin;

(2) insulin sensitizers, including (i) PPARγ agonists, such as the glitazones (e.g. pioglitazone, rosiglitazone, netoglitazone, rivoglitazone, and balaglitazone) and other PPAR ligands, including (1) PPARα/γ dual agonists, such as muraglitazar, aleglitazar, sodelglitazar, and naveglitazar, (2) PPARα agonists, such as fenofibric acid derivatives (gemfibrozil, clofibrate, ciprofibrate, fenofibrate and bezafibrate), (3) selective PPARγ modulators (SPPARγM's), such as those disclosed in WO 02/060388, WO 02/08188, WO 2004/019869, WO 2004/020409, WO 2004/020408, and WO 2004/066963, and (4) PPARγ partial agonists; (ii)

biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors;

(3) insulin or insulin analogs, such as insulin lispro, insulin detemir, insulin glargine, insulin glulisine, and inhalable formulations of each thereof;

(4) leptin and leptin derivatives and agonists;

(5) amylin and amylin analogs, such as pramlintide;

(6) sulfonylurea and non-sulfonylurea insulin secretagogues, such as tolbutamide, glyburide, glipizide, glimepiride, mitiglinide, and meglitinides, such as nateglinide and repaglinide;

(7) α-glucosidase inhibitors (such as acarbose, voglibose and miglitol);

(8) glucagon receptor antagonists, such as those disclosed in WO 98/04528, WO 99/01423, WO 00/39088, and WO 00/69810;

(9) incretin mimetics, such as GLP-1, GLP-1 analogs, derivatives, and mimetics; and GLP-1 receptor agonists, such as exenatide, liraglutide, taspoglutide, AVE0010, CJC-1131, and BIM-51077, including intranasal, transdermal, and once-weekly formulations thereof;

(10) LDL cholesterol lowering agents such as (i) HMG-CoA reductase inhibitors (lovastatin, simvastatin, pravastatin, cerivastatin, fluvastatin, atorvastatin, pitavastatin, and rosuvastatin), (ii) bile acid sequestering agents (such as cholestyramine, colestimide, colesevelam hydrochloride, colestipol, and dialkylaminoalkyl derivatives of a cross-linked dextran, (iii) inhibitors of cholesterol absorption, such as ezetimibe, and (iv) acyl CoA:cholesterol acyltransferase inhibitors, such as avasimibe;

(11) HDL-raising drugs, such as niacin or a salt thereof and extended-release versions thereof;

(12) antiobesity compounds such as topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists (such as MK-0557); CBT receptor inverse agonists and antagonists (such as rimonabant and taranabant); $β_3$ adrenergic receptor agonists; ghrelin antagonists; bombesin receptor agonists (such as bombesin receptor subtype-3 agonists); and 5-hydroxytryptamine-2c (5-HT2c) agonists, such as lorcaserin;

(13) agents intended for use in inflammatory conditions, such as aspirin, non-steroidal anti-inflammatory drugs (NSAIDs), glucocorticoids, and selective cyclooxygenase-2 (COX-2) inhibitors;

(14) antihypertensive agents, such as ACE inhibitors (such as enalapril, lisinopril, ramipril, captopril, quinapril, and tandolapril), A-II receptor blockers (such as losartan, candesartan, irbesartan, olmesartan medoxomil, valsartan, telmisartan, and eprosartan), renin inhibitors (such as aliskiren), beta blockers (such as and calcium channel blockers (such as;

(15) glucokinase activators (GKAs), such as LY2599506;

(16) inhibitors of 11β-hydroxysteroid dehydrogenase type 1, such as those disclosed in U.S. Pat. No. 6,730,690; WO 03/104207; and WO 04/058741;

(17) inhibitors of cholesteryl ester transfer protein (CETP), such as torcetrapib and MK-0859;

(18) inhibitors of fructose 1,6-bisphosphatase, such as those disclosed in U.S. Pat. Nos. 6,054,587; 6,110,903; 6,284,748; 6,399,782; and 6,489,476;

(19) inhibitors of acetyl CoA carboxylase-1 or 2 (ACC1 or ACC2);

(20) AMP-activated Protein Kinase (AMPK) activators;

(21) agonists of the G-protein-coupled receptors: GPR-109, GPR-119, and GPR-40;

(22) SSTR3 antagonists, such as those disclosed in WO 2009/011836;

(23) neuromedin U receptor agonists, such as those disclosed in WO2009/042053, including, but not limited to, neuromedin S (NMS);

(24) inhibitors of stearoyl-coenzyme A delta-9 desaturase (SCD);

(25) GPR-105 antagonists, such as those disclosed in WO 2009/000087;

(26) inhibitors of glucose uptake, such as sodium-glucose transporter (SGLT) inhibitors and its various isoforms, such as SGLT-1; SGLT-2, such as dapagliflozin, canagliflozin, ertugliflozin, empagliflozin, ipragliflozin and remogliflozin; and SGLT-3;

(27) inhibitors of acyl coenzyme A:diacylglycerol acyltransferase 1 and 2 (DGAT-1 and DGAT-2);

(28) inhibitors of fatty acid synthase;

(29) inhibitors of acetyl-CoA carboxylase-1 and 2 (ACC-1 and ACC-2);

(30) inhibitors of acyl coenzyme A:monoacylglycerol acyltransferase 1 and 2 (MGAT-1 and MGAT-2);

(31) agonists of the TGR5 receptor (also known as GPBAR1, BG37, GPCR19, GPR131, and M-BAR); and

(32) bromocriptine mesylate and rapid-release formulations thereof.

In another aspect of the invention, a pharmaceutical composition is disclosed which comprises:

(a) a compound described herein or a pharmaceutically acceptable salt thereof;

(b) one or more compounds selected from the group consisting of:

(1) dipeptidyl peptidase-IV (DPP-4) inhibitors;

(2) insulin sensitizers, including (i) PPARγ agonists, such as the glitazones (e.g. pioglitazone, rosiglitazone, netoglitazone, rivoglitazone, and balaglitazone) and other PPAR ligands, including (1) PPARα/γ dual agonists, such as muraglitazar, aleglitazar, sodelglitazar, and naveglitazar, (2) PPARα agonists, such as fenofibric acid derivatives (gemfibrozil, clofibrate, ciprofibrate, fenofibrate and bezafibrate), (3) selective PPARγ modulators (SPPARγM's), and (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors;

(3) sulfonylurea and non-sulfonylurea insulin secretagogues, such as tolbutamide, glyburide, glipizide, glimepiride, mitiglinide, and meglitinides, such as nateglinide and repaglinide;

(4) α-glucosidase inhibitors (such as acarbose, voglibose and miglitol);

(5) glucagon receptor antagonists;

(6) LDL cholesterol lowering agents such as (i) HMG-CoA reductase inhibitors (lovastatin, simvastatin, pravastatin, cerivastatin, fluvastatin, atorvastatin, pitavastatin, and rosuvastatin), (ii) bile acid sequestering agents (such as cholestyramine, colestimide, colesevelam hydrochloride, colestipol, and dialkylaminoalkyl derivatives of a cross-linked dextran, (iii) inhibitors of cholesterol absorption, such as ezetimibe, and (iv) acyl CoA:cholesterol acyltransferase inhibitors, such as avasimibe;
(7) HDL-raising drugs, such as niacin or a salt thereof and extended-release versions thereof;
(8) antiobesity compounds;
(9) agents intended for use in inflammatory conditions, such as aspirin, non-steroidal anti-inflammatory drugs (NSAIDs), glucocorticoids, and selective cyclooxygenase-2 (COX-2) inhibitors;
(10) antihypertensive agents, such as ACE inhibitors (such as enalapril, lisinopril, ramipril, captopril, quinapril, and tandolapril), A-II receptor blockers (such as losartan, candesartan, irbesartan, olmesartan medoxomil, valsartan, telmisartan, and eprosartan), renin inhibitors (such as aliskiren), beta blockers and calcium channel blockers;
(11) glucokinase activators (GKAs), such as LY2599506;
(12) inhibitors of 11β-hydroxysteroid dehydrogenase type 1;
(13) inhibitors of cholesteryl ester transfer protein (CETP), such as torcetrapib and MK-0859;
(14) inhibitors of fructose 1,6-bisphosphatase;
(15) inhibitors of acetyl CoA carboxylase-1 or 2 (ACC1 or ACC2);
(16) AMP-activated Protein Kinase (AMPK) activators;
(17) agonists of the G-protein-coupled receptors: GPR-109, GPR-119, and GPR-40;
(18) SSTR3 antagonists;
(19) neuromedin U receptor agonists, including, but not limited to, neuromedin S (NMS);
(20) inhibitors of stearoyl-coenzyme A delta-9 desaturase (SCD);
(21) GPR-105 antagonists;
(22) inhibitors of glucose uptake, such as sodium-glucose transporter (SGLT) inhibitors and its various isoforms, such as SGLT-1; SGLT-2, such as dapagliflozin, canagliflozin, ertugliflozin, empagliflozin, ipragliflozin and remogliflozin; and SGLT-3;
(23) inhibitors of acyl coenzyme A:diacylglycerol acyltransferase 1 and 2 (DGAT-1 and DGAT-2);
(24) inhibitors of fatty acid synthase;
(25) inhibitors of acetyl-CoA carboxylase-1 and 2 (ACC-1 and ACC-2);
(26) inhibitors of acyl coenzyme A:monoacylglycerol acyltransferase 1 and 2 (MGAT-1 and MGAT-2);
(27) agonists of the TGR5 receptor (also known as GPBAR1, BG37, GPCR19, GPR131, and M-BAR); and
(28) bromocriptine mesylate and rapid-release formulations thereof; and
(c) a pharmaceutically acceptable carrier.

The pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, in particular embodiments from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Compositions and Administration

When administered to a subject, the Compounds of Formula I may be administered as a component of a composition that comprises a pharmaceutically acceptable carrier or vehicle. The present invention provides pharmaceutical compositions comprising an effective amount of at least one Compound of Formula I and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules may be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Compounds of Formula I are administered orally.

In another embodiment, the one or more Compounds of Formula I are administered intravenously.

In one embodiment, a pharmaceutical preparation comprising at least one Compound of Formula I is in unit dosage form. In such form, the preparation is subdivided into unit doses containing effective amounts of the active components.

Compositions may be prepared according to conventional mixing, granulating or coating methods, respectively, and the present compositions can contain, in one embodiment, from about 0.1% to about 99% of the Compound(s) of Formula I by weight or volume. In various embodiments, the present compositions can contain, in one embodiment, from about 1% to about 70% or from about 5% to about 60% of the Compound(s) of Formula I by weight or volume.

The compounds of Formula I may be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions may be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The unit dosages of the Compounds of Formula I may be administered at varying frequencies. In one embodiment, a unit dosage of a Compound of Formula I may be administered once daily. In another embodiment, a unit dosage of a Compound of Formula I may be administered twice weekly. In another embodiment, a unit dosage of a Compound of Formula I may be administered once weekly. In still another embodiment, a unit dosage of a Compound of Formula I may be administered once biweekly. In another embodiment, a unit dosage of a Compound of Formula I may be administered once monthly. In yet another embodiment, a unit dosage of a Compound of Formula I may be administered once bimonthly. In another embodiment, a unit dosage of a Compound of Formula I may be administered once every 3 months. In a further embodiment, a unit dosage of a Compound of Formula I may be administered once every 6 months. In another embodiment, a unit dosage of a Compound of Formula I may be administered once yearly.

The amount and frequency of administration of the Compounds of Formula I will be regulated according to the judgment of the attending clinician considering such factors as age, condition and size of the subject as well as severity of the symptoms being treated. The compositions of the invention can further comprise one or more additional therapeutic agents, selected from those listed above herein.

Kits

In one aspect, the present invention provides a kit comprising a therapeutically effective amount of at least one Compound of Formula I, or a pharmaceutically acceptable salt or prodrug of said compound and a pharmaceutically acceptable carrier, vehicle or diluent.

In another aspect the present invention provides a kit comprising an amount of at least one Compound of Formula I, or a pharmaceutically acceptable salt or prodrug of said compound and an amount of at least one additional therapeutic agent listed above, wherein the amounts of the two or more active ingredients result in a desired therapeutic effect. In one embodiment, the one or more Compounds of Formula I and the one or more additional therapeutic agents are provided in the same container. In one embodiment, the one or more Compounds of Formula I and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound of the formula:

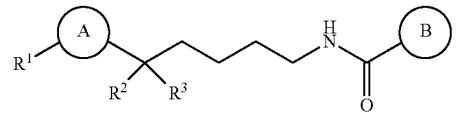

wherein

is a five-membered heteroaryl ring which is optionally substituted with halo, cyano or $C_{1-3}$ alkyl;

is phenyl or heteroaryl, which may be monocyclic or bicyclic, wherein said phenyl and heteroaryl groups are optionally substituted with one to three substituents independently selected from the group consisting of halo, oxo, cyano, $R^4$, $R^6$, $OR^4$, $NHR^4$, $NR^4R^5$, $NO_2$ and $SR^4$;

$R^1$ is naphthalenyl or quinolinyl wherein said naphthalenyl and quinolinyl groups are optionally substituted with one to two groups independently selected from the group consisting of halo, oxo, cyano, $R^4$ and $OR^4$;

$R^2$ is selected from the group consisting of $NH(C=O)R^6$, $NH(C=O)CH(CH_3)R^6$ and $NH(C=O)R^4$;

$R^3$ is hydrogen or $C_{1-6}$ alkyl;

or $R^2$ and $R^3$ can be taken together with the atoms to which they are attached to form a 5-membered heterocyclyl group which is optionally substituted with oxo;

each $R^4$ is independently hydrogen or $C_{1-6}$ alkyl, which is optionally substituted with one to three groups independently selected from the group consisting of halo, cyano and $OR^5$;

each $R^5$ is independently hydrogen or $C_{1-6}$ alkyl;

$R^6$ is (a) heterocyclyl, which may be monocyclic or bicyclic, (b) $C_{3-6}$ cycloalkyl, (c) phenyl, or (d) heteroaryl, which may be monocyclic or bicyclic, wherein said heterocyclyl, cycloalkyl, phenyl and heteroaryl groups are optionally substituted with one to two groups independently selected from the group consisting of oxo, $R^4$ and $OR^4$;

or a pharmaceutically acceptable salt thereof.

2. The compound of claim 1 wherein (A)

is imidazolyl, or a pharmaceutically acceptable salt thereof.

3. The compound of claim 1 wherein (B)

is selected from phenyl, pyridinyl, pyrazolyl, pyrazolopyrimidinyl, oxadiazolyl, thiadiazolyl, isothiazolyl, or dihydroindenyl, wherein said groups are optionally substituted with one to three substituents independently selected from the group consisting of halo, oxo, cyano, $R^4$, $R^6$, $OR^4$, $NHR^4$, $NR^4R^5$, $NO_2$ and $SR^4$; or a pharmaceutically acceptable salt thereof.

4. The compound of claim 1 wherein $R^1$ is naphthalenyl or quinolinyl wherein said quinolinyl group is optionally substituted with $OR^4$; or a pharmaceutically acceptable salt thereof.

5. The compound of claim 1 wherein $R^2$ is $NH(C=O)R^6$ or $NH(C=O)C(CH_3)R^6$, and $R^6$ is selected from the group consisting of azetidinyl, piperidinyl, pyrazolyl, tetrahydropyranyl and thiazolyl; or a pharmaceutically acceptable salt thereof.

6. The compound of claim 1 wherein $R^2$ is $NH(C=O)$ thiazolyl, or a pharmaceutically acceptable salt thereof.

7. A compound selected from

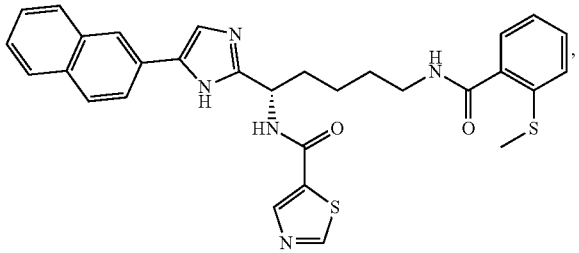

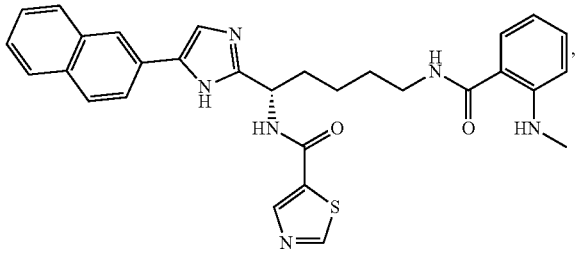

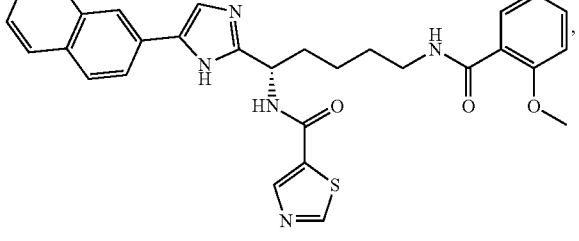

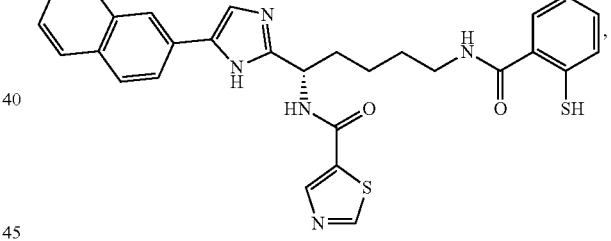

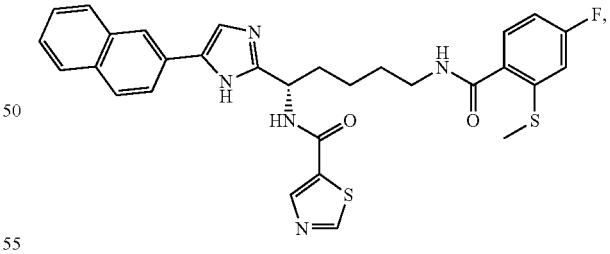

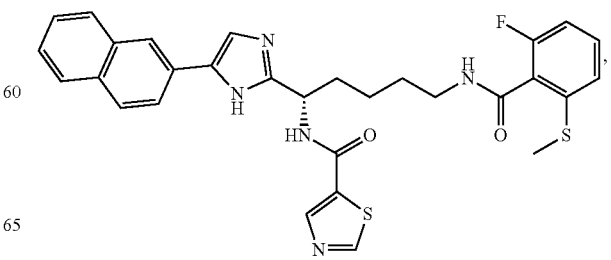

75
-continued
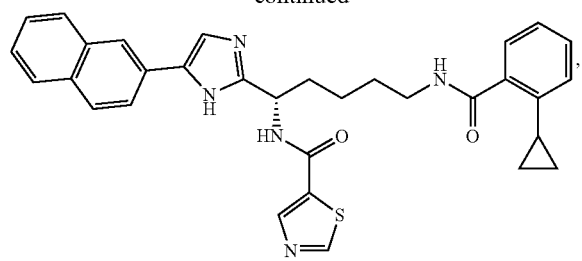
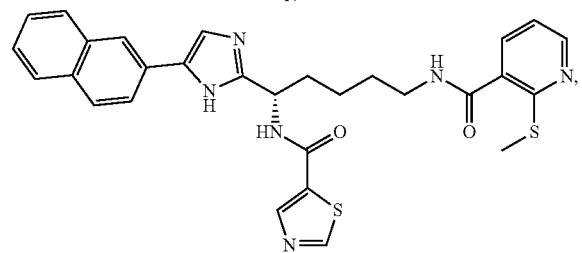
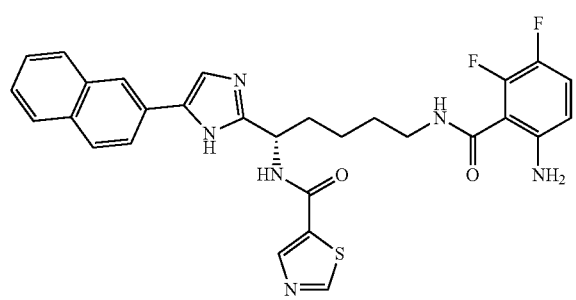
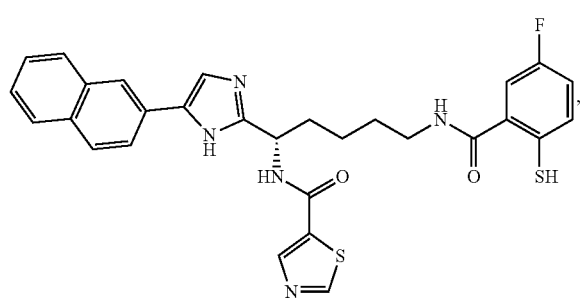
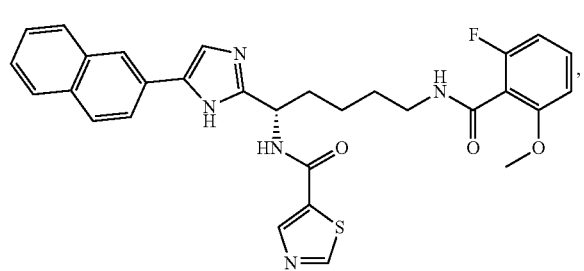
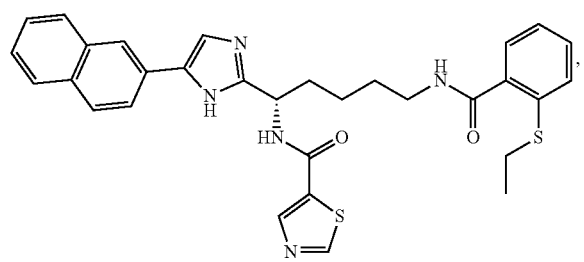
76
-continued
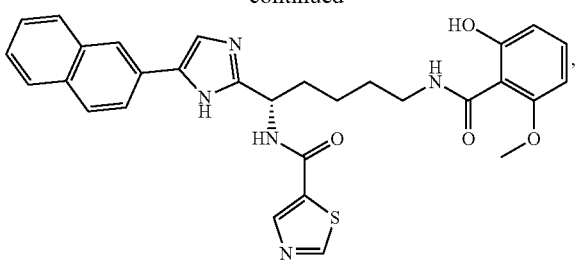
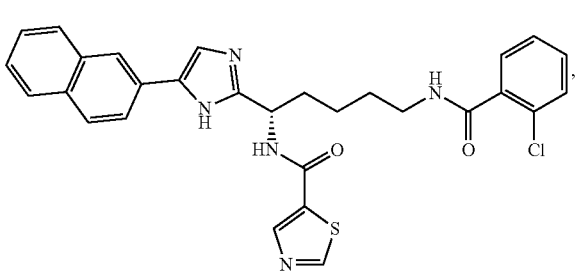
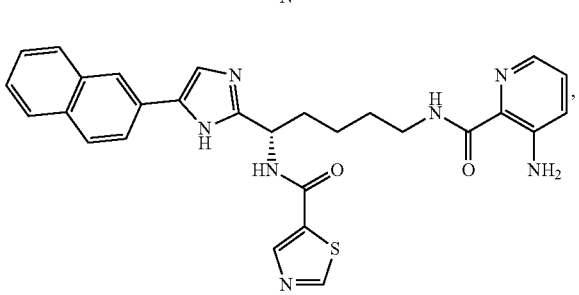
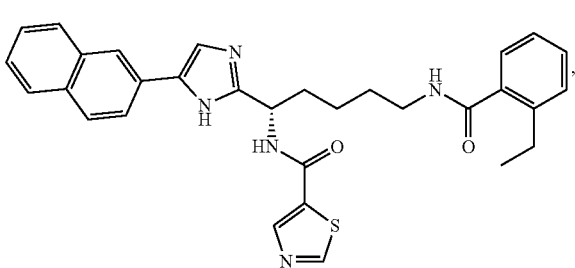
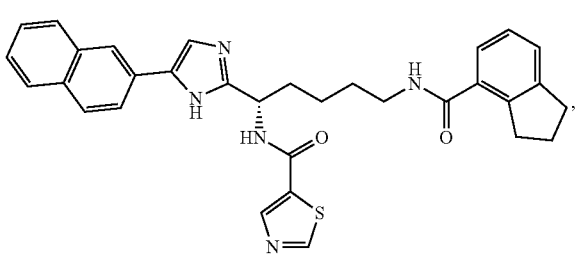
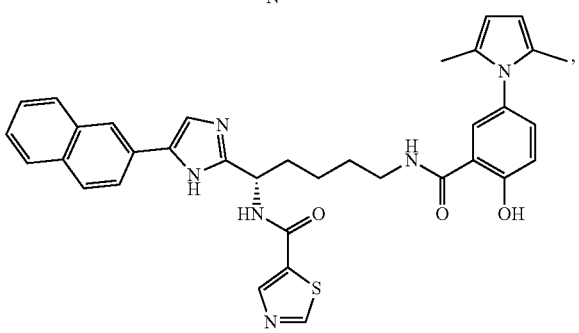

77
-continued
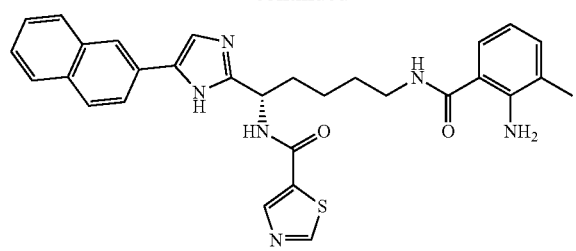
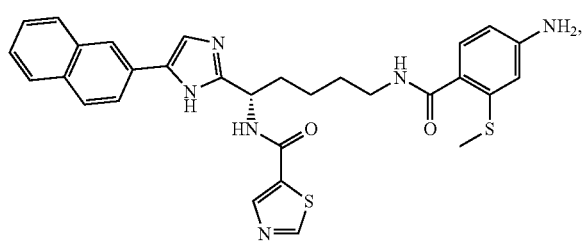
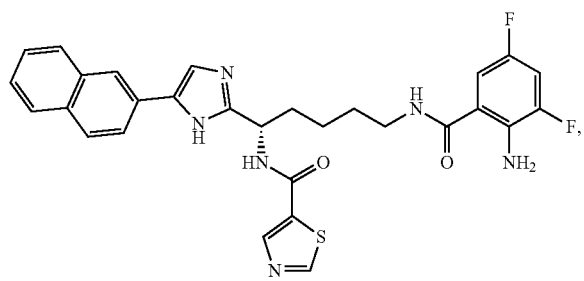
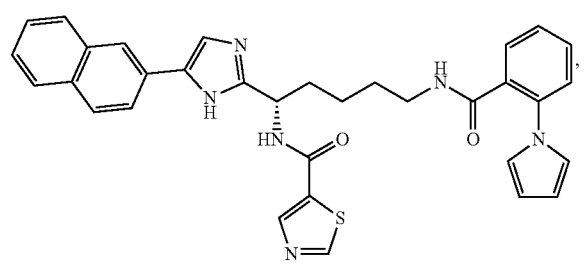
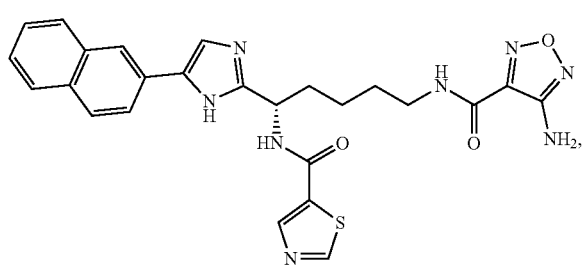
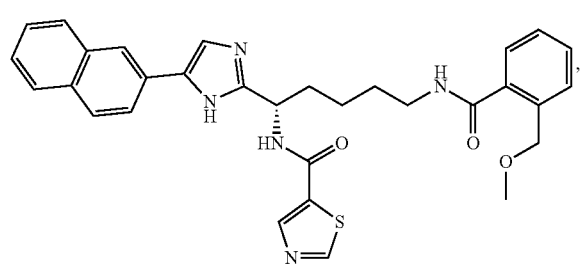
78
-continued
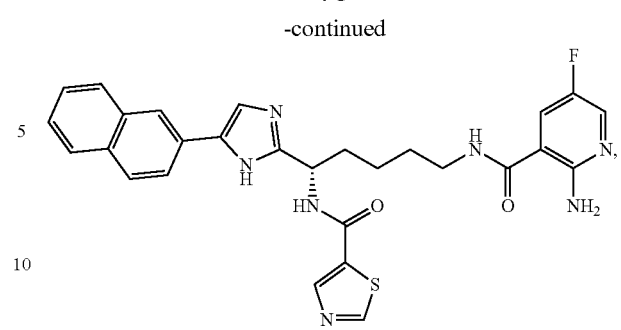
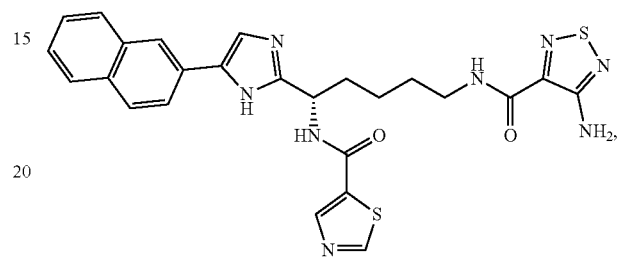
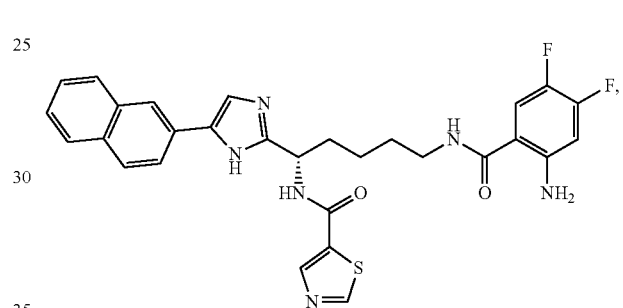
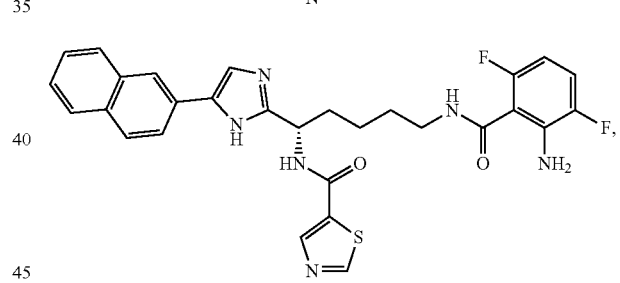
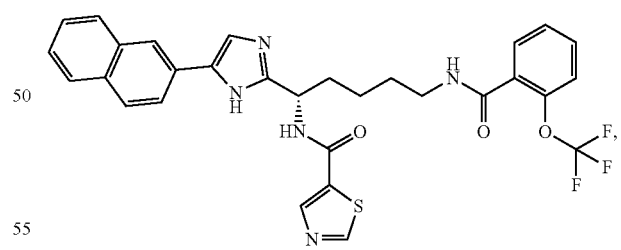
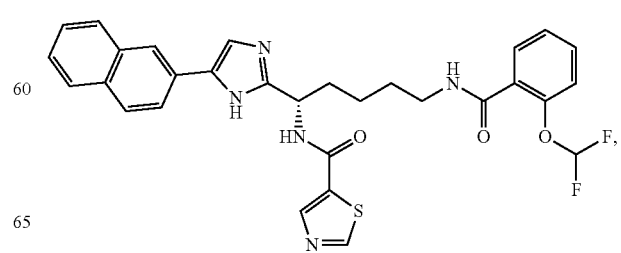

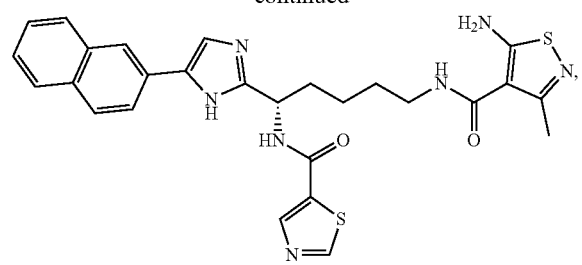
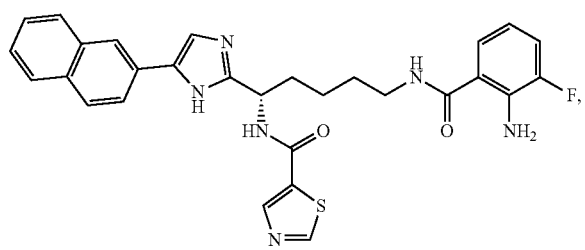
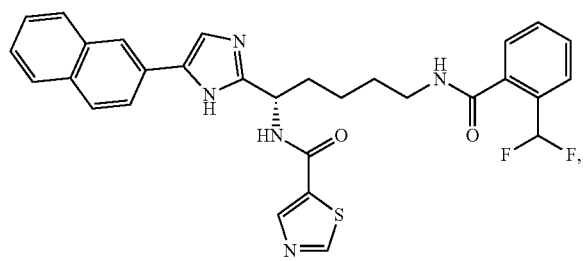
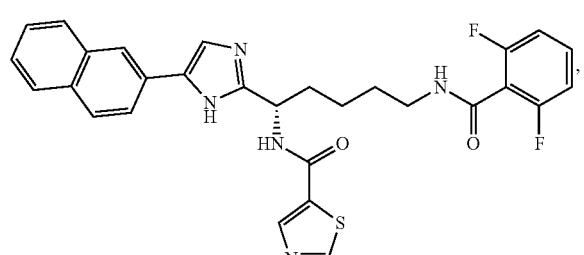
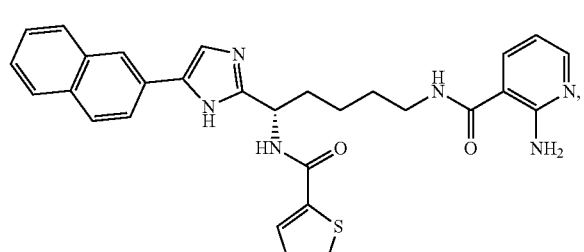
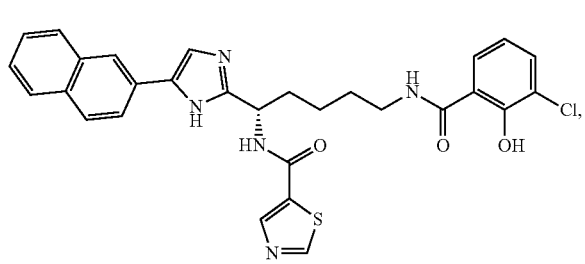
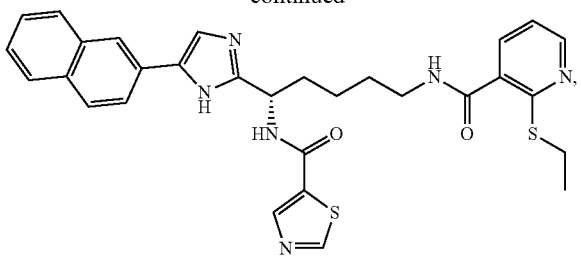
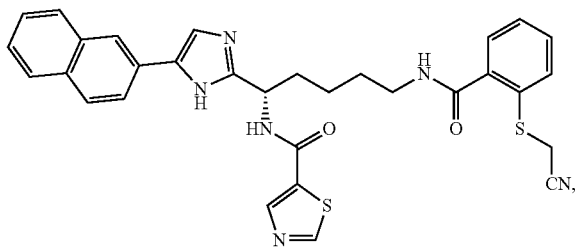
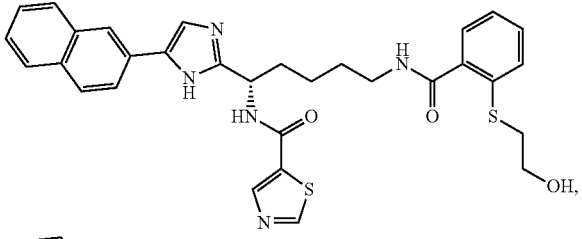
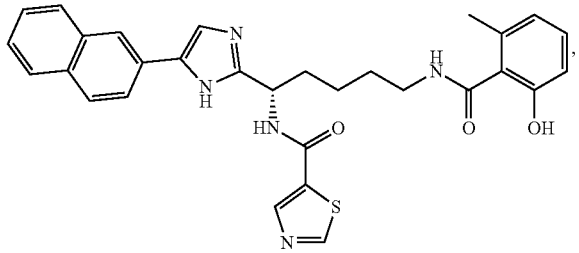
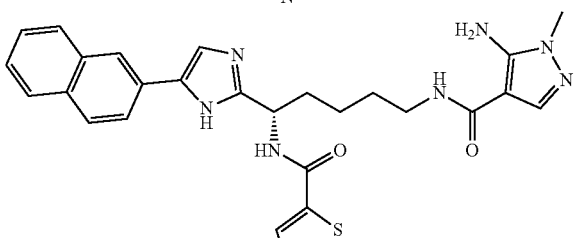
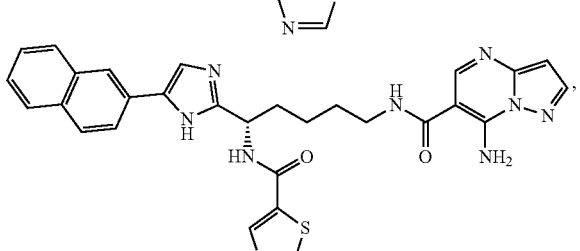
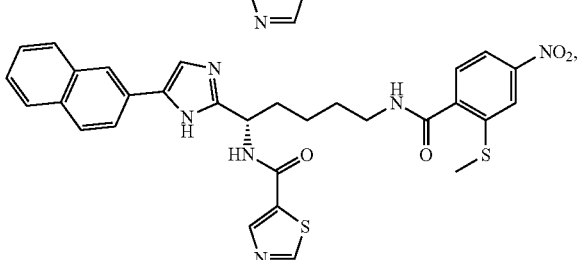

-continued
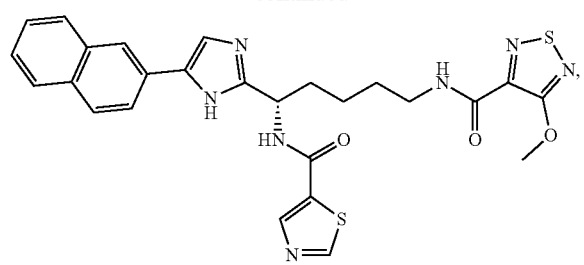
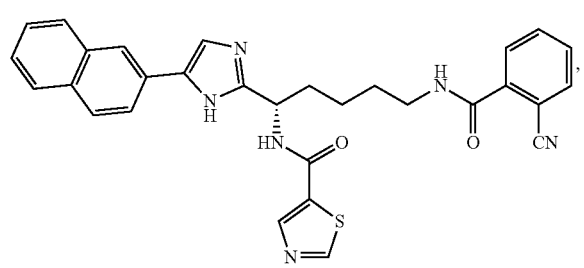
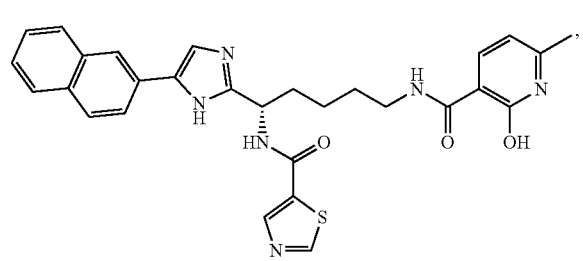
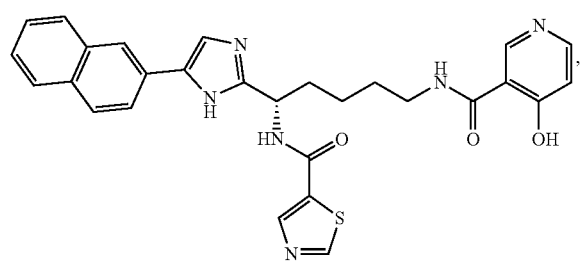
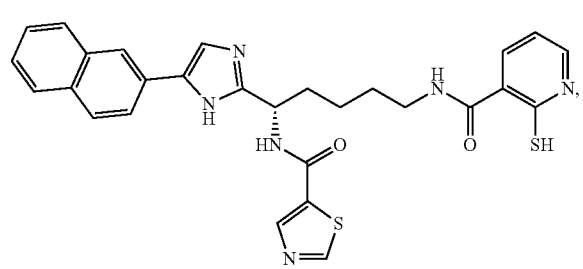
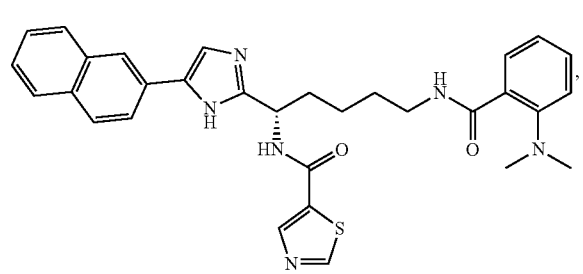
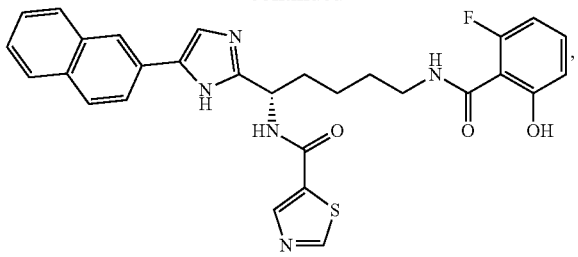
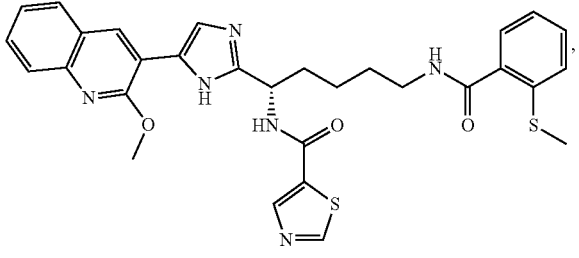
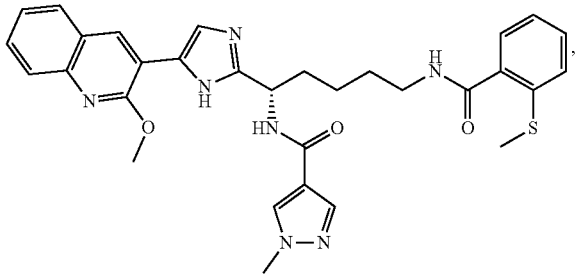
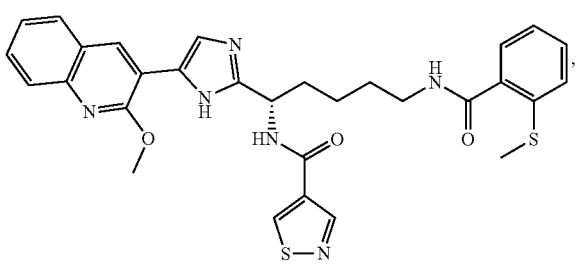
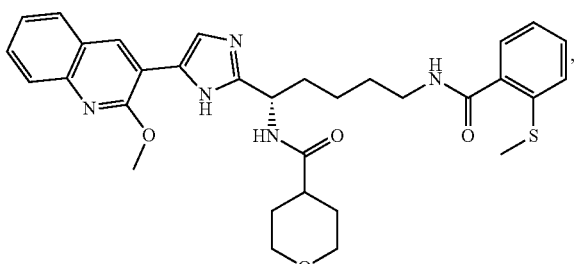
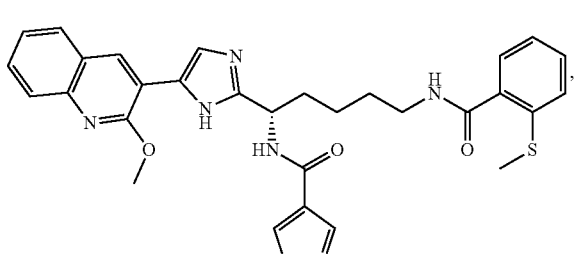

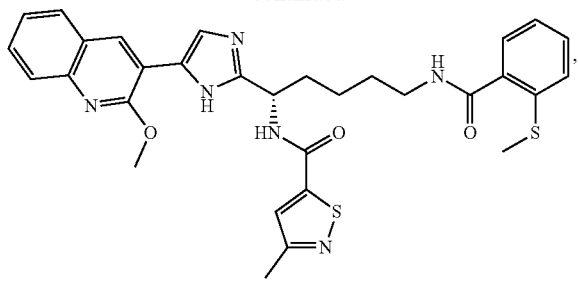

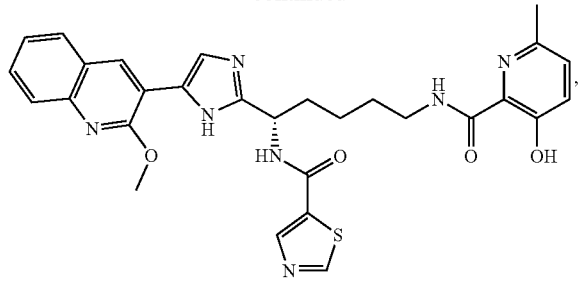

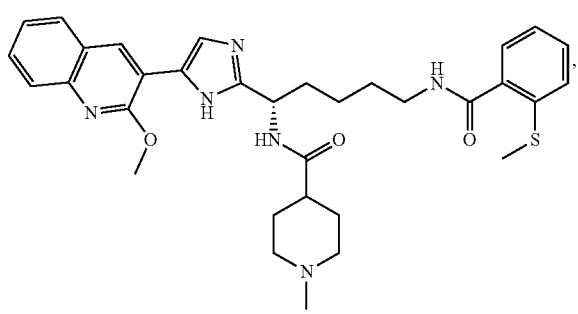

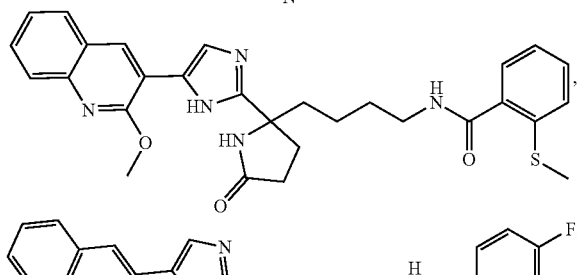

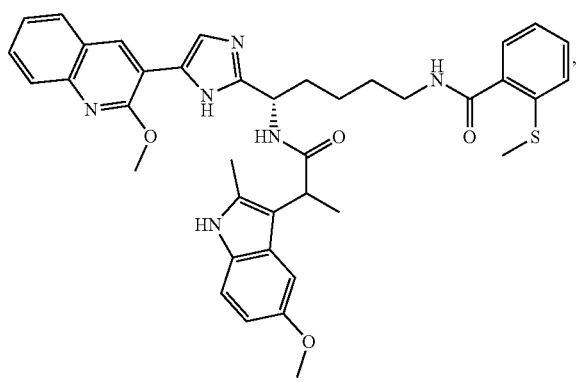

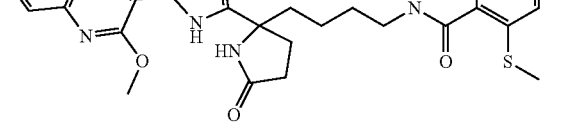

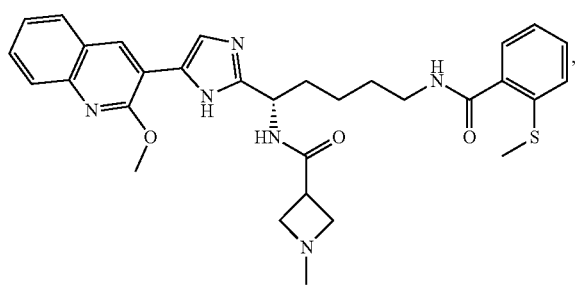

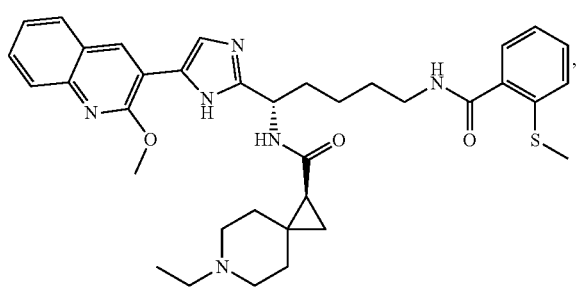

or a pharmaceutically acceptable salt thereof.

8. A pharmaceutical composition comprising an effective amount of a compound of claim 1, or a pharmaceutically acceptable salt thereof, and a pharmaceutically acceptable carrier.

9. A method for the inhibition of HDAC in a subject in need thereof which comprises administering to the subject an effective amount of a compound of claim 1, or a pharmaceutically acceptable salt thereof.

10. A method for the treatment of infection by HIV or for the treatment, prophylaxis, or delay in the onset or progression of AIDS in a subject in need thereof, which comprises administering to the subject an effective amount of a compound of claim 1, or a pharmaceutically acceptable salt thereof.

11. A compound of claim 1, or a pharmaceutically acceptable salt thereof, for use in the preparation of a medicament for the inhibition of HDAC, for the treatment or prophylaxis of infection by HIV, or for the treatment, prophylaxis, or delay in the onset or progression of AIDS in a subject in need thereof.

12. The pharmaceutical composition of claim 8, further comprising one or more additional therapeutic agents selected from raltegravir, lamivudine, abacavir, ritonavir, darunavir, atazanavir, emtricitabine, tenofovir, rilpivirine, doravirine, EFdA and lopinavir.

13. The method of claim 10, further comprising administering to the subject one or more additional therapeutic agents selected from raltegravir, lamivudine, abacavir, ritonavir, darunavir, atazanavir, emtricitabine, tenofovir, rilpivirine, doravirine, EFdA and lopinavir, wherein the amounts administered of the compound of claim 1 and the one or more additional therapeutic agents, are together effective to treat infection by HIV or to treat, prevent or delay the onset or progression of AIDS.

\* \* \* \* \*